(12) United States Patent
Smit et al.

(10) Patent No.: US 10,975,360 B2
(45) Date of Patent: Apr. 13, 2021

(54) PROCESS FOR THE MODIFICATION OF ALKANES, FATTY ACIDS AND FATTY ALCOHOLS

(71) Applicant: UNIVERSITY OF THE FREE STATE, Bloemfontein (ZA)

(72) Inventors: Martha Sophia Smit, Bloemfontein (ZA); Diederik Johannes Opperman, Bloemfontein (ZA); Alizé Pennec, Saint Quay Portrieux (FR); Jacqueline Van Marwijk, Vanderbijlpark (ZA); Mpeyake Jacob Maseme, Virginia (ZA); Alberto Perojil Jimenez, Granada (ES)

(73) Assignee: UNIVERSITY OF THE FREE STATE, Bloemfontein (ZA)

( * ) Notice: Subject to any disclaimer, the term of this patent is extended or adjusted under 35 U.S.C. 154(b) by 194 days.

(21) Appl. No.: 15/757,754

(22) PCT Filed: Feb. 10, 2017

(86) PCT No.: PCT/IB2017/050732
§ 371 (c)(1),
(2) Date: Mar. 6, 2018

(87) PCT Pub. No.: WO2017/137935
PCT Pub. Date: Aug. 17, 2017

(65) Prior Publication Data
US 2020/0248213 A1    Aug. 6, 2020

(30) Foreign Application Priority Data
Feb. 12, 2016  (GB) ................................ 1602574

(51) Int. Cl.
*C12N 9/02* (2006.01)
*C12P 7/62* (2006.01)
(Continued)

(52) U.S. Cl.
CPC .............. *C12N 9/0071* (2013.01); *C12P 7/02* (2013.01); *C12P 7/62* (2013.01); *C12P 17/06* (2013.01); *C12R 1/66* (2013.01)

(58) Field of Classification Search
CPC ........ C12N 9/0071; C12P 7/62; C12P 7/6409; C12P 7/02
See application file for complete search history.

(56) References Cited

U.S. PATENT DOCUMENTS

| | | |
|---|---|---|
| 2001/0053839 A1 | 12/2001 | Noishiki et al. |
| 2007/0010831 A1 | 1/2007 | Romero-Ortega et al. |
| 2012/0020933 A1 | 1/2012 | Young et al. |

OTHER PUBLICATIONS

Maseme. CYP505E3: A Novel Self-Sufficient w-7 In-Chain Hydroxylase. Angew. Chem. Int. Ed. 2020, 59, 10359-10362.*
(Continued)

*Primary Examiner* — Yong D Pak
(74) *Attorney, Agent, or Firm* — Saliwanchik, Lloyd & Eisenschenk

(57) ABSTRACT

The present invention relates to a process for the microbial in-chain hydroxylation of C12 to C16 fatty acids, alcohols and alkanes at position ω-7, the process including the use of a microorganism expressing a cytochrome P450 monooxygenase CYP505E3 or related fungal cytochrome P450 monooxygenases sharing at least 70% amino acid identity in the production of a hydroxylated product or secondary product. The present invention further relates to a process for the preparation of lactones, esters and polymers by hydroxylation of the corresponding fatty acids, fatty alcohols and alkane precursors by a recombinant cytochrome P450 monooxygenase CYP505E3 or related fungal cytochrome P450 monooxygenases sharing at least 70% amino acid identity.

13 Claims, 24 Drawing Sheets
Specification includes a Sequence Listing.

R = $(CH_2)_n COOH$; $(CH_2)_n COH$ or $(CH_2)_n CH_3$
n = 2 to 6

(51) Int. Cl.
   C12P 17/06    (2006.01)
   C12P 7/02     (2006.01)
   C12P 7/04     (2006.01)
   C12P 7/08     (2006.01)
   C12P 7/46     (2006.01)
   C12R 1/66     (2006.01)

(56) References Cited

OTHER PUBLICATIONS

Studer. Residue mutations and their impact on protein structure and function: detecting beneficial and pathogenic changes. Biochem. J. (2013) 449, 581-594.*
Vatsyayan. Broad substrate Cytochrome P450 monooxygenase activity in the cells of Aspergillus terreus MTCC 6324. Bioresource Technology 99 (2008) 68-75.*
Choi, S. et al., "Microplate Assay Measurement of Cytochrome P450-Carbon Monoxide Complexes." Journal of Biochemistry and Molecular Biology, May 2003, 36 (3): 332-335.
Crešnar, B. Petrič, S., "Cytochrome P450 Enzymes in the Fungal Kingdom." Biochim. Biophys. Acta., Jan. 2011, 1814 (1): Abstract.
Durairaj, P. et al., "Versatile biocatalysis of fungal cytochrome P450 monooxygenases." Microbial Cell Factories, 2016, 15 (125): 1-16.
Fairbanks, G. et al., "Electrophoretic Analysis of the Major Polypeptides of the Human Erythrocyte Membrane." Biochemistry, 1971, 10 (13): 2606-2617.
Gillam, E. M., "Engineering cytochrome p450 enzymes." Chem. Res. Toxicol., Jan. 2008, 21 (1): Abstract.
Gudiminchi, R. K., Smit, M. S., "Identification and characterization of 4-hexylbenzoic acid an 4-nonyloxybenzoic acid as substrates of CYP102A1." Appl. Microbiol. Biotehnol., 2011, 90: 117-126.
Inoue, H. et al., "High efficiency transformation of *Escherichia coli* with plasmids." Gene, Nov. 1990, 96 (1): Abstract.
Johnston, W. A. et al., "Quantitative Whole-Cell Cytochrome p450 Measurement Suitable for High-Throughput Application." Journal of Biomolecular Screening, 2008, 13 (2): 135-141.

Kara, S. et al., "Access to Lactone Building Blocks via Horse Liver Alcohol Dehydrogenase-Catalyzed Oxidative Lactonization." ACS Catal., 2013, 3 (11): Abstract.
Khow, O., Suntrarachun, S., "Strategies for production of active eukaryotic proteins in bacterial expression system." Asian Pacific Journal of Tropical Biomedicine, 2012, 2 (2): 159-162.
Kitazume, T. et al., "Fusarium ozysporum fatty-acid subterminal hydroxylase (CYP505) is a membrane-bound eukaryotic counterpart of Bacillus megaterium cytochrome P450BM3." J. Biol. Chem., Dec. 2000, 275 (50): 39734-39740.
Kitazume, T. et al., "Kinetic analysis of hydroxylation of saturated fatty acids by recombinant P450foxy produced by an *Escherichia coil* expression system." The FEBS Journal, 2002, 269 (8): 1-16.
Kuloyo, O., "Heterologous Expression of Cytochrome P450 Monooxygenases from Aspergillus terreus and Cryptococcus neoformans." University of the Free State, Department of Microbial, Biochemical and Food Biotechnology, Masters thesis, Jun. 2014, 1-103.
Laemmli, U. K., "Cleavage of Structural Proteins during the Assembly of the Head of Bacteriophage T4." Nature, Aug. 1970, 227: 680-685.
Li, S. et al., "Engineering and Analysis of a Self-Sufficient Biosynthetic Cytochrome (450 PikC Fused to the RhFRED Reductase Domain." J. Am. Chem. Soc., Oct. 2007, 129 (43): 12940-12941.
Moktali, V. et al., "Systematic and searchable classification of cytochrome P450 proteins encaded by fungal and oomycete genomes." BMC Genomics, 2012, 13(525): 1-13.
Nakayama, N. et al., "Cytochrome P450foxy, a catalytically self-sufficient fatty acid hydroxylase of the fungus *Fusarium oxysporum*." Journal of Biochemistry, Mar. 1996, 119 (3): 435-440.
Omura, T., Sato, R., "The Carbon Monoxide-binding Pigment of Liver Microsomes." The Journal of Biological Chemistry, Jul. 1964, 239 (7): 2370-2378.
Park, J. et al., "Fungal cytochrome P450 database." BMC Genomics, Aug. 2008, 9 (402): 1-11.
Plackett, R. L., Burman, J. P., "The Design of Optimum Multifactorial Experiments." Biometrika, Jun. 1946, 33 (4): Introduction.

* cited by examiner

HLADH - horseliver alcohol dehydrogenase

A

B

| | 1,3diol | 1,4diol | 1,5diol | 1,9diol | 1,10diol |
|---|---|---|---|---|---|
| x | 3 | 4 | 5 | 9 | 10 |
| $C_xH_{2x+1}O_2$ (m/z) | 75 | 89 | 103 | 159 | 173 |
| $C_xH_{2x+1}O_2-H_2O$ (m/z) | 57 | 71 | 85 | 141 | 155 |
| $C_xH_{2x+1}O_2-2H_2O$ (m/z) | 39 | 53 | 67 | 123 | 137 |
| $C_{13-x}H_{27-2x}O$ (m/z) | 157 | 143 | 129 | 73 | 59 |
| $C_{13-x}H_{27-2x}O-H_2O$ (m/z) | 139 | 125 | 111 | 55 | 41 |
| $M^+$ | 202 | 202 | 202 | 202 | 202 |
| $M^+-2H_2O$ | 166 | 166 | 166 | 166 | 166 |

| | CYP505A1 | CYP505Ao | CYP505Hv | CYP505Om | CYP505St | CYP505Pe | CYP505Pc | CYP505Pf | CYP505E3 | CYP505E1 | CYP505Ak | CYP505An |
|---|---|---|---|---|---|---|---|---|---|---|---|---|
| CYP505A1 | ✕ | 42.6% | 45.1% | 45.1% | 47.8% | 43.7% | 43.9% | 44.3% | 44.9% | 44.1% | 43.3% | 43.5% |
| CYP505Ao | 42.6% | ✕ | 45.4% | 42.6% | 47.6% | 46.4% | 46.0% | 45.5% | 46.6% | 46.9% | 47.3% | 47.5% |
| CYP505Hv | 45.1% | 45.4% | ✕ | 46.8% | 49.8% | 46.8% | 47.3% | 47.2% | 47.8% | 48.0% | 47.7% | 48.3% |
| CYP505Om | 45.1% | 42.6% | 46.8% | ✕ | 49.9% | 47.1% | 47.7% | 46.9% | 48.2% | 47.3% | 48.2% | 48.4% |
| CYP505St | 47.8% | 47.6% | 49.8% | 49.9% | ✕ | 49.0% | 49.1% | 48.4% | 50.4% | 50.7% | 49.7% | 49.8% |
| CYP505Pe | 43.7% | 46.4% | 46.8% | 47.1% | 49.0% | ✕ | 86.4% | 85.2% | 74.2% | 72.8% | 74.7% | 74.9% |
| CYP505Pc | 43.9% | 46.0% | 47.3% | 47.7% | 49.1% | 86.4% | ✕ | 92.8% | 76.2% | 73.7% | 74.0% | 74.6% |
| CYP505Pf | 44.3% | 45.5% | 47.2% | 46.9% | 48.4% | 85.2% | 92.8% | ✕ | 75.0% | 73.7% | 73.3% | 73.9% |
| CYP505E3 | 44.9% | 46.6% | 47.8% | 48.2% | 50.4% | 74.2% | 76.2% | 75.0% | ✕ | 75.1% | 76.2% | 76.7% |
| CYP505E1 | 44.1% | 46.9% | 48.0% | 47.3% | 50.7% | 72.8% | 73.7% | 73.7% | 75.1% | ✕ | 80.3% | 81.0% |
| CYP505Ak | 43.3% | 47.3% | 47.7% | 48.2% | 49.7% | 74.7% | 74.0% | 73.3% | 76.2% | 80.3% | ✕ | 96.7% |
| CYP505An | 43.5% | 47.5% | 48.3% | 48.4% | 49.8% | 74.9% | 74.6% | 73.9% | 76.7% | 81.0% | 96.7% | ✕ |

FIGURE 23

SEQUENCE LISTING

```
<160> NUMBER OF SEQ ID NOS: 19

<210> SEQ ID NO 1
<211> LENGTH: 1050
<212> TYPE: PRT
<213> ORGANISM: Aspergillus terreus

<400> SEQUENCE: 1

Met Ile Lys Glu Thr Glu Gln Ile Pro Gly Pro Arg Pro Leu Pro Val
1               5                   10                  15

Val Gly Asn Leu Phe Asp Met Asp Leu Glu His Gly Leu Glu Cys Leu
            20                  25                  30

Ile Arg Leu Ala Asp Asp Phe Gly Pro Leu Phe Gln Ile Thr Ile Asn
        35                  40                  45

Gly Glu Lys Gln Ile Phe Ala Thr Ser Gln Ala Leu Val Asp Glu Leu
    50                  55                  60

Cys Asp Glu Ser Arg Phe His Lys Ala Val Met Gly Gly Leu Glu Lys
65                  70                  75                  80

Leu Arg Met Leu Ala Ser Asp Gly Leu Phe Thr Ala Tyr His Gly Glu
                85                  90                  95

Arg Gly Trp Gly Ile Ala His Arg Ile Leu Val Pro Ala Phe Gly Pro
            100                 105                 110

Leu Arg Ile Arg Asn Met Phe Glu Glu Met Asn Asp Val Ala Gln Gln
        115                 120                 125

Leu Cys Leu Lys Trp Ala Arg Gln Gly Ser Ser Thr Ser Ile Asn Ile
    130                 135                 140

Thr Asp Asp Phe Thr Arg Leu Thr Leu Asp Thr Ile Ala Leu Cys Thr
145                 150                 155                 160
```

```
Met Asn Phe Arg Leu Asn Ser Phe Tyr Asn Asn Glu Thr Met His Pro
                165                 170                 175
Phe Val Lys Ser Met Leu Tyr Val Leu Arg Glu Ser Asp Ile Gln Ser
            180                 185                 190
Met Leu Pro Gly Ile Ala Asn Cys Ile Arg Val Lys Ala Arg Ser Arg
        195                 200                 205
Met Ser Lys His Ile Gln Leu Met Arg Asn Met Ala Arg Gly Ile Ile
    210                 215                 220
Gln Glu Arg Arg Asp Gln Ala Glu Pro Val Asp Leu Leu Asn Thr
225                 230                 235                 240
Leu Leu Asn Gly Arg Asp Pro Val Thr Gly Glu Gly Met Ser Asp Asp
                245                 250                 255
Leu Ile Ile Asn Asn Val Ile Thr Phe Leu Ile Ala Gly His Glu Thr
            260                 265                 270
Thr Ser Gly Leu Leu Ser Phe Thr Phe Tyr Tyr Leu Leu Gln Asn Pro
        275                 280                 285
His Ile Leu Glu Arg Ala Gln Asn Glu Val Asp Glu Val Thr Gly Gly
    290                 295                 300
Glu Arg Ile Thr Val Gln His Leu Gly Arg Leu Thr Tyr Ile Asp Ala
305                 310                 315                 320
Ile Leu Lys Glu Ser Leu Arg Leu Met Pro Thr Ala Pro Ala Phe Thr
                325                 330                 335
Val Thr Pro Lys Lys Pro Glu Val Leu Gly Gly Ala Trp Ala Ile Asp
            340                 345                 350
Ala Gly Gln Ala Val Asn Val Leu Leu Pro Val Cys Leu Arg Asp Arg
        355                 360                 365
Ser Val Phe Gly Pro Asp Ala Asp Glu Phe Arg Pro Glu Arg Met Leu
    370                 375                 380
Glu Glu Asn Phe Ser Lys Leu Pro Pro Asn Ser Trp Lys Pro Phe Gly
385                 390                 395                 400
Asn Gly Glu Arg Ser Cys Ile Gly Arg Ala Phe Ala Trp Gln Glu Ala
                405                 410                 415
Gln Leu Val Val Ala Met Val Leu Gln Thr Phe Asp Leu Val Pro Asp
            420                 425                 430
Asp Pro Ser Tyr Lys Leu Arg Ile Lys Glu Thr Leu Thr Ile Lys Pro
        435                 440                 445
Asp Gly Phe Arg Val Arg Ala Thr Leu Arg Arg Gly Gln Ser Ala Thr
    450                 455                 460
Gly Leu Ser Gln Gly Ser Met Ser Ala Ser Gly Ala Thr Ser Ser Val
465                 470                 475                 480
Ala Ser Pro Gly Pro Pro Ala Ala Thr Gly Ala Gln Ser Asn Pro Ala
                485                 490                 495
Gly Gly Gln Arg Ile Ser Phe Phe Tyr Gly Ser Asn Ser Gly Thr Cys
            500                 505                 510
Lys Ala Leu Ala His Arg Leu Ala Ser Ser Leu Met Gly Arg Gly Phe
        515                 520                 525
Thr Glu Gln Lys Leu Ala Ala Leu Asp Thr Val Val Gly Asn Leu Pro
    530                 535                 540
Thr Asp Gln Pro Val Ile Ile Val Thr Thr Ser Tyr Asp Gly Arg Pro
545                 550                 555                 560
Thr Asp Asp Ala Glu Glu Phe Val Arg Trp Leu Glu Ser Lys Arg Pro
                565                 570                 575
Val Leu Gln Gly Val Ser Tyr Ala Val Phe Gly Cys Gly His His Asp
```

```
                580             585             590
Trp Ala Lys Thr Phe Tyr Arg Ile Pro Ile Leu Ile Asp Asp Leu Met
            595             600             605

His Lys Ala Gly Ala Thr Arg Leu Thr Ala Leu Gly Thr Ala Asn Ala
610             615             620

Ala Val Ser Asp Leu Phe Ser Asp Leu Glu Leu Trp Glu Glu Thr Asn
625             630             635             640

Leu Leu Pro Ala Leu Arg Glu Ala Phe Pro Pro Ser Asn Ser Ser Asp
            645             650             655

Val Glu Ser Ser Glu Pro His Gln Leu Gln Ile Cys Val Ser Lys Pro
            660             665             670

Arg Arg Val Asp Met His Arg Gly Leu Val Glu Ala Lys Val Thr Ala
            675             680             685

Val Arg Thr Leu Thr Ser Pro Asp Ser Pro Glu Lys Arg His Val Glu
            690             695             700

Phe His Val Gln Gly Asp Thr Thr Trp Arg Pro Gly Asp His Val Asn
705             710             715             720

Ile Leu Pro Val Asn Pro Leu Ser Thr Val Ser Arg Val Leu Ala Tyr
            725             730             735

Phe Gln Leu Ala Pro Asp His Ser Ile Thr Val Asn Ser Phe Asn Thr
            740             745             750

Gln Gly Leu Pro Ser Ala Thr Pro Val Ser Ala Thr Glu Leu Phe Ser
            755             760             765

Ser Phe Val Glu Leu Ser Gln Pro Ala Thr Arg Lys Asn Leu Lys Ala
            770             775             780

Leu Ala Met Ala Ala Glu Ser Lys Thr Asp Glu Gln Glu Leu Ile Arg
785             790             795             800

Leu His Asp Ser Tyr Asp Ala Leu Val Arg Asp Lys Arg Val Ser Val
            805             810             815

Leu Asp Ile Leu Glu Arg Phe Pro Ser Ile Ser Leu Pro Ile Gly Ile
            820             825             830

Phe Ile Ser Met Leu Pro Pro Leu Arg Leu Arg Thr Tyr Ser Leu Ser
            835             840             845

Met Ala Pro Ser Phe Lys Pro Ser His Gly Ser Leu Thr Phe Ser Val
            850             855             860

Ile Asn Glu Pro Ala Trp Ser Asn Gly Gln Tyr Leu Gly Val Gly
865             870             875             880

Ser Asn Tyr Leu Ala Ser Leu Thr Pro Gly Ser Leu Leu Tyr Leu Ser
            885             890             895

Pro Arg Pro Ala Lys Asp Ala Phe His Leu Pro Ala Asp Gln Phe Asn
            900             905             910

Thr Pro Ile Ile Met Ile Cys Ala Gly Ser Gly Leu Ala Pro Phe Met
            915             920             925

Gly Phe Ile Gln Glu Arg Met Thr Trp Leu Lys Gln Gly Arg Pro Leu
            930             935             940

Ala Lys Gly Leu Leu Phe Phe Gly Cys Arg Gly Pro His Leu Asp Asp
945             950             955             960

Leu Tyr Tyr Glu Glu Leu Ser Glu Phe Glu Asp Ala Gly Val Val Glu
            965             970             975

Val His Arg Ala Tyr Ser Arg Ala Pro Asp Asp Val Arg Ala Lys Gly
            980             985             990

Cys Arg His Val Gln His Arg Leu  Val Thr Glu Ala Glu  Ala Val Arg
            995             1000            1005
```

Asp His Trp Gly Arg Asn Ala Ile Val Tyr Val Cys Gly Ser Ser
    1010                1015                1020

Asn Met Ala Arg Gly Val Gln Thr Val Leu Glu Glu Ile Leu Gly
    1025                1030                1035

Thr Leu Pro Pro Glu Arg Tyr Val Ala Glu Ile Phe
    1040                1045                1050

<210> SEQ ID NO 2
<211> LENGTH: 1063
<212> TYPE: PRT
<213> ORGANISM: Aspergillus niger

<400> SEQUENCE: 2

Met Arg Asp Ala Glu Arg Ile Pro Gly Pro Thr Pro Leu Pro Val Val
1               5                   10                  15

Gly Asn Leu Phe Asp Ile Asp Leu Glu His Val Leu Gln Ser Val Ile
                20                  25                  30

Gly Leu Ala Asn Lys Tyr Gly Pro Leu Phe Gln Ile Thr Ile Asn Gly
            35                  40                  45

Glu Lys Gln Ile Phe Ala Thr Ser Gln Ala Leu Val Asp Glu Leu Cys
50                  55                  60

Asp Glu Ser Arg Phe His Lys Ala Val Ala Ser Gly Leu Glu Asn Leu
65                  70                  75                  80

Arg Met Leu Ala His Asp Gly Leu Phe Thr Ala Tyr His Gly Glu Arg
                85                  90                  95

Gly Trp Gly Ile Ala His Arg Ile Leu Val Pro Ala Phe Gly Pro Leu
            100                 105                 110

Arg Ile Gln Ser Met Phe Asp Asp Met Gly Asp Leu Ala Gln Gln Leu
        115                 120                 125

Cys Leu Lys Trp Ala Arg Gln Gly Ala Ser Asn Ser Ile Asn Ile Thr
130                 135                 140

Asp Asp Phe Thr Arg Leu Thr Leu Asp Thr Ile Ala Leu Cys Thr Met
145                 150                 155                 160

Asp Phe Arg Leu Asn Ser Phe Tyr Asn Asn Asp Thr Met His Pro Phe
                165                 170                 175

Val Glu Ser Met Leu Tyr Val Leu Arg Glu Ala Asp Val Gln Ser Ala
            180                 185                 190

Leu Pro Gly Ile Ala Asn Ser Val Arg Ile Met Ala His Arg Arg Met
        195                 200                 205

Leu Lys Asn Ile Glu Ala Met Arg Thr Ile Ala Arg Asp Ile Ile His
    210                 215                 220

Asp Arg Arg Lys Lys Glu Asn Pro Ala Asp Asp Leu Leu Asn Thr Leu
225                 230                 235                 240

Leu Asn Gly Arg Asp Pro Val Thr Gly Glu Gly Met Ser Asp Glu Ser
                245                 250                 255

Ile Ile Asp Asn Val Ile Thr Phe Leu Val Ala Gly His Glu Thr Thr
            260                 265                 270

Ser Gly Leu Leu Ser Phe Thr Phe Tyr Tyr Leu Val Gln His Pro Asp
        275                 280                 285

Ile Leu Lys Lys Ala Gln Lys Glu Val Asp Glu Thr Val Gly Gln Ala
    290                 295                 300

Gln Ile Ser Val Gln His Leu Ala Glu Leu Pro Tyr Ile Asp Ala Ile
305                 310                 315                 320

Leu Lys Glu Ser Leu Arg Met Met Pro Thr Ala Pro Gly Phe Thr Val

```
            325                 330                 335
Thr Pro Lys Lys Ala Glu Thr Leu Gly Gly Lys Trp Leu Leu Asn Ala
            340                 345                 350
Gly Gln Pro Ile Asn Val Leu Leu Pro Ala Cys Leu Arg Asp Arg Ser
            355                 360                 365
Ile Phe Gly Pro Asn Ala Asp Glu Phe Ser Pro Gly Arg Met Leu Ala
            370                 375                 380
Glu Asn Phe Ser Lys Leu Pro Pro Asn Ser Trp Lys Pro Phe Gly Asn
385                 390                 395                 400
Gly Glu Arg Ser Cys Ile Gly Arg Ala Phe Ala Trp Gln Glu Ala Gln
                    405                 410                 415
Leu Val Val Ala Met Ile Leu Gln Asn Phe Asp Leu Val Pro Asp Asp
                    420                 425                 430
Pro Ser Tyr Thr Leu Arg Ile Lys Glu Thr Leu Thr Ile Lys Pro Asp
                    435                 440                 445
Gly Phe Arg Val Arg Ala Thr Leu Arg His Arg Gln Thr Ala Thr Gly
            450                 455                 460
Leu Phe Gln His Thr Leu Ser Ala Arg Asn Asp Thr Ser Leu Ala Ser
465                 470                 475                 480
Ser Ser Ala His Phe Ile Lys Lys Ser Glu Asp Gln Ala Pro Ala Gly
                    485                 490                 495
Gly Arg Pro Ile Cys Phe Phe Tyr Gly Ser Asn Ser Gly Thr Cys Lys
            500                 505                 510
Ala Leu Ala His Arg Leu Ala Ser Asp Leu Met Pro Tyr Gly Phe Thr
            515                 520                 525
Asp Gln Lys Leu Ala Val Leu Asp Thr Ala Val Asp Asn Leu Pro Arg
            530                 535                 540
Asp Gln Pro Val Ile Ile Leu Thr Thr Thr Tyr Asp Gly Gln Pro Thr
545                 550                 555                 560
Asp Asp Ala Lys Lys Phe Val Ala Trp Leu Glu Ser Gly Lys Val Pro
                    565                 570                 575
Ala Leu Gln Gly Ile Ser Tyr Ala Val Phe Gly Cys Gly His His Asp
                    580                 585                 590
Trp Thr Gln Thr Phe Tyr Arg Ile Pro Thr Leu Ile Asp Glu Leu Met
            595                 600                 605
His Lys Ala Gly Ala Thr Arg Leu Ala Pro Arg Gly Thr Ala Asn Ala
            610                 615                 620
Ala Val Ser Asp Leu Phe Ser Asp Leu Glu Ala Trp Glu Glu Thr Ser
625                 630                 635                 640
Leu Leu Pro Ala Leu Arg Glu Thr Phe Leu Leu Ser Ser Ser Ser Asp
                    645                 650                 655
Leu Glu Pro Leu Asn Leu His Gln Gln Ile Ser Leu Ser Lys Pro
                    660                 665                 670
Arg Arg Ile Asp Leu His Lys Asp Leu Met Glu Ala Arg Val Thr Thr
            675                 680                 685
Val Arg Ile Leu Thr Asn Pro Asp Thr Pro Glu Lys Arg His Ile Glu
            690                 695                 700
Phe Arg Phe Gln Gly Asp Thr Thr Leu Arg Pro Gly Asp His Val Asn
705                 710                 715                 720
Val Leu Pro Val Asn Pro Pro Ser Thr Val Leu Arg Val Leu Ala Gln
                    725                 730                 735
Phe Asn Leu Ala Pro Asp Tyr Ser Ile Thr Ile Asn Ser Phe Asn Thr
            740                 745                 750
```

```
Leu Gly Leu Pro Gln Ala Thr Pro Val Ser Ala Ser Glu Leu Phe Ser
        755                 760                 765

Ala Tyr Val Glu Leu Ser Gln Pro Ala Thr Arg Asn Asn Leu Arg Ile
770                 775                 780

Leu Ala Ala Thr Ala Gln Ser Asp Glu Asp Lys Gln Glu Leu Ile His
785                 790                 795                 800

Leu Gln Asp Ser Tyr Asp Ser Leu Val Arg Asp Lys Arg Val Ser Val
        805                 810                 815

Leu Asp Leu Leu Glu Gln Phe Pro Ser Val Ser Leu Pro Ile Ala Ala
        820                 825                 830

Phe Ile Ser Met Leu Pro Ala Leu Arg Leu Arg Thr Tyr Ser Leu Ser
        835                 840                 845

Leu Ala Pro Ser Phe Lys Pro Ser His Gly Ser Leu Thr Phe Ser Val
        850                 855                 860

Val Asn Glu Pro Ala Arg Asn Gly Asn Arg Arg Tyr Leu Gly Val Gly
865                 870                 875                 880

Ser Asn Tyr Leu Ala Ser Leu Thr Pro Gly Ser Ile Leu Tyr Leu Ser
        885                 890                 895

Pro Arg Pro Ala Lys Glu Ala Phe His Leu Pro Val Asp Gln Ser Arg
        900                 905                 910

Ile Pro Ile Ile Met Ile Cys Ala Gly Ser Gly Leu Ala Pro Phe Leu
        915                 920                 925

Ser Phe Ile Gln Asp Arg Met Ile Trp Gln Gln Asp Lys Pro Leu
        930                 935                 940

Ala Arg Ala Leu Leu Phe Phe Gly Cys Gly Arg Phe Leu Asp Asp
945                 950                 955                 960

Leu Tyr His Glu Glu Leu Ser Glu Phe Glu Ala Ala Gly Val Val Asp
        965                 970                 975

Val Arg Arg Ala Tyr Ser Lys Val Leu Asp Tyr Asp Met Ala Arg Gly
        980                 985                 990

Cys Lys Tyr Val Gln Asp Arg Leu Val Ala Glu Ala Asn Ala Ile Arg
        995                 1000                1005

His Leu Trp Ala Gln Asp Ala Thr Ile Tyr Val Cys Gly Ser Ala
        1010                1015                1020

Asp Met Ala Lys Gly Val Glu Gly Val Leu Glu Lys Leu Leu Gly
        1025                1030                1035

Met Leu Pro Arg Glu Arg Tyr Val Thr Glu Ile Tyr Gln Met Gln
        1040                1045                1050

Thr Arg Asp Asn Val Ser Glu Trp Leu Ile
        1055                1060

<210> SEQ ID NO 3
<211> LENGTH: 1050
<212> TYPE: PRT
<213> ORGANISM: Aspergillus kawachii

<400> SEQUENCE: 3

Met Lys Asp Ala Glu Arg Ile Pro Gly Pro Lys Pro Leu Pro Val Val
1               5                   10                  15

Gly Asn Leu Phe Asp Ile Asp Pro Glu His Ser Leu Glu Ser Ile Val
            20                  25                  30

Ala Phe Ala Glu Lys Phe Gly Pro Leu Phe Gln Ile Thr Ile Asn Gly
        35                  40                  45

Glu Lys Gln Ile Phe Ala Thr Ser Gln Ala Leu Val Asp Glu Leu Cys
```

```
            50                  55                  60
Asp Glu Leu Arg Phe His Lys Ala Val Val Thr Gly Leu Glu Ile Leu
 65                  70                  75                  80

Arg Leu Leu Ala His Asp Gly Leu Phe Thr Ala Tyr His Gly Glu Arg
                 85                  90                  95

Gly Trp Gly Ile Ala His Arg Ile Leu Val Pro Ala Phe Gly Pro Leu
                100                 105                 110

Arg Ile Arg Asn Met Leu Asp Asp Met Ser Asp Val Ala Gln Gln Leu
                115                 120                 125

Cys Leu Lys Trp Ala Arg Gln Gly Gly Ser Thr Ser Ile Asn Ile Thr
130                 135                 140

Glu Asp Phe Thr Arg Leu Thr Leu Asp Thr Ile Ala Leu Cys Thr Met
145                 150                 155                 160

Gly Phe Arg Leu Asn Ser Phe Tyr Asn Asn Glu Thr Met His Pro Phe
                165                 170                 175

Val Gln Ser Met Leu Tyr Val Leu Arg Glu Ala Asp Ile Gln Ala Asn
                180                 185                 190

Leu Pro Gly Ile Ala Asn Ser Ile Arg Val Ser Ala Gln Arg Arg Met
                195                 200                 205

His Lys Asn Ile Glu Ala Met Arg Thr Met Ala Arg Gly Ile Ile Gln
210                 215                 220

Glu Arg Arg Lys Asn Lys Asn Pro Val Asp Asp Ile Leu Asn Thr Leu
225                 230                 235                 240

Leu Asn Gly Arg Asp Pro Val Thr Gly Glu Gly Met Ser Asp Asp Ser
                245                 250                 255

Ile Ile Asp Asn Val Ile Thr Phe Leu Ile Ala Gly His Glu Thr Thr
                260                 265                 270

Ser Gly Leu Leu Ser Phe Thr Phe Tyr Phe Leu Ile Gln His Pro His
                275                 280                 285

Ile Leu Lys Lys Ala Gln Glu Glu Val Asp Glu Thr Val Gly Leu Ala
                290                 295                 300

Gln Ile Ser Ala Gln His Leu Ala Glu Leu Pro Tyr Ile Asp Ala Ile
305                 310                 315                 320

Leu Lys Glu Ser Leu Arg Leu Met Pro Thr Ala Pro Gly Phe Thr Val
                325                 330                 335

Thr Pro Lys Lys Thr Glu Val Leu Gly Gly Arg Trp Met Ile Asn Ala
                340                 345                 350

Gly Gln Pro Val Asn Val Leu Leu Pro Ala Cys Leu Arg Asp Gln Ser
                355                 360                 365

Val Phe Gly Pro Asp Ala Asp Glu Phe Arg Pro Glu Arg Met Leu Ala
370                 375                 380

Glu Asn Phe Ser Lys Leu Pro Pro Asn Ser Trp Lys Pro Phe Gly Asn
385                 390                 395                 400

Gly Glu Arg Gly Cys Ile Gly Arg Ala Phe Ala Trp Gln Glu Ala Gln
                405                 410                 415

Leu Val Val Ala Met Ile Leu Gln Thr Phe Asp Leu Val Pro Asp Asp
                420                 425                 430

Pro Ser Tyr Gln Leu Arg Ile Lys Glu Thr Leu Thr Ile Lys Pro Asp
                435                 440                 445

Gly Phe Arg Ile Arg Ala Thr Leu Arg Gly Gln Thr Ala Thr Gly
                450                 455                 460

Leu Ser Arg Arg Ser Met Leu Val Ala Arg Asp Gly Ser Ser Glu Glu
465                 470                 475                 480
```

```
Ser Ser Asn His Pro Ala Glu Ala Arg Gly Asp His Ala Pro Ala Arg
            485                 490                 495

Gly Gln Pro Val Ser Phe Phe Tyr Gly Ser Asn Ser Gly Thr Cys Lys
        500                 505                 510

Ala Leu Ala His Gln Leu Ala Ser Asn Met Met Ser Arg Gly Tyr Thr
            515                 520                 525

Thr Gln Lys Leu Ala Pro Leu Asp Asn Ala Val Asp Asn Leu Pro Arg
        530                 535                 540

Asp Gln Pro Val Ile Ile Leu Thr Thr Thr Tyr Asp Gly Gln Pro Thr
545                 550                 555                 560

Asp Asn Ala Lys Lys Phe Val Ala Trp Leu Glu Thr Gly Asn Val Leu
            565                 570                 575

Ser Leu Gln Gly Ile Ser Tyr Ala Val Phe Gly Cys Gly His His Asp
            580                 585                 590

Trp Thr Gln Thr Phe Tyr Arg Ile Pro Ile Leu Ile Asp Asp Leu Met
        595                 600                 605

Tyr Lys Ala Gly Ala Thr Arg Leu Ala Pro Arg Gly Ala Ala Asn Ala
        610                 615                 620

Ala Val Ser Asp Leu Phe Ser Asp Leu Glu Ala Trp Glu Glu Thr Ser
625                 630                 635                 640

Leu Leu Pro Ala Leu Arg Glu Asn Phe Leu Pro Ser Asn Ser Thr Asp
            645                 650                 655

Phe Asp Pro Leu Asn Pro His Gln Ile Gln Leu Ser Leu Ser Lys Pro
            660                 665                 670

Arg Arg Val Asp Leu His Lys Gly Leu Ile Glu Ala Lys Val Thr Ala
            675                 680                 685

Val Arg Val Leu Thr Ser Pro Asp Thr Pro Glu Lys Arg His Leu Glu
        690                 695                 700

Phe Cys Phe Gln Gly Asp Leu Ser Leu Arg Pro Gly Asp His Leu Asn
705                 710                 715                 720

Ile Leu Pro Val Asn Pro Ser Thr Val Ser Arg Val Leu Ala Gln
            725                 730                 735

Phe Asn Leu Ala Pro Asp Tyr Asn Ile Thr Val Asn Ser Phe Asn Thr
            740                 745                 750

Leu Gly Leu Pro Gln Ala Thr Pro Val Ser Ala Ser Glu Leu Phe Ser
        755                 760                 765

Ser Tyr Val Glu Leu Cys Gln Pro Ala Thr Arg Asn Asn Leu Lys Ser
        770                 775                 780

Leu Ile Ala Ala Thr Gln Ser Asp Thr Val Lys Gln Glu Leu Asn Arg
785                 790                 795                 800

Leu Tyr Asp Ser Tyr Glu Phe Ile Val Arg Asp Lys Arg Val Ser Val
            805                 810                 815

Leu Asp Leu Leu Glu Gln Phe Pro Ser Ile Ser Leu Pro Ile Ala Ala
            820                 825                 830

Phe Ile Ser Met Leu Pro Ala Leu Arg Val Arg Thr Tyr Ser Leu Ser
            835                 840                 845

Met Ala Pro Ala Phe Lys Pro Ser His Ser Ser Leu Thr Phe Ser Val
850                 855                 860

Ile Asn Glu Pro Ala Trp Arg Gly Ser Gly Gln His Leu Gly Val Ala
865                 870                 875                 880

Ser Asn Tyr Leu Ala Ser Leu Thr Ser Gly Ser Ile Pro Tyr Phe Ser
            885                 890                 895
```

```
Pro Arg Pro Ala Lys Glu Thr Phe His Leu Pro Lys Asp Pro Ser Arg
                900                 905                 910

Thr Pro Ile Ile Met Ile Cys Ala Gly Ser Gly Leu Ala Pro Phe Leu
            915                 920                 925

Ser Phe Ile Gln Asp Arg Met Val Leu Lys Gln Gln Asn Lys Pro Leu
        930                 935                 940

Ala Lys Ala Phe Leu Phe Phe Gly Cys Arg Gly Arg Ser Leu Asp Asp
945                 950                 955                 960

Leu Tyr His Glu Glu Leu Ser Glu Tyr Glu Ala Gly Val Val Glu
                965                 970                 975

Val Arg Arg Ala Tyr Ser Lys Thr Pro Glu Phe Asp Ile Ala Lys Gly
            980                 985                 990

Cys Arg Tyr Val Gln His Arg Leu Val Thr Glu Gly Gln Ala Ile Leu
        995                 1000                1005

Ser Leu Trp Ala Gln Asn Ala Ile Ile Tyr Val Cys Gly Ser Thr
        1010                1015                1020

Ser Met Ala Lys Gly Ala Glu Ala Val Leu Gln Asn Met Leu Gly
        1025                1030                1035

Pro Leu Pro Lys Glu Arg Tyr Val Thr Glu Ile Phe
        1040                1045                1050

<210> SEQ ID NO 4
<211> LENGTH: 1048
<212> TYPE: PRT
<213> ORGANISM: Penicillium expansum

<400> SEQUENCE: 4

Met Lys Asp Met Glu Ser Ile Pro Gly Pro Lys Pro Leu Pro Val Val
1               5                   10                  15

Gly Asn Leu Phe Asp Ile Asp Leu Glu Asn Gly Leu Gln Ser Ile Ile
            20                  25                  30

Lys Met Ala His Glu Phe Gly Pro Leu Phe Gln Ile Thr Ile Asn Gly
        35                  40                  45

Gln Lys Gln Ile Phe Ala Thr Ser Gln Ala Leu Val Asp Glu Leu Cys
    50                  55                  60

Asp Glu Thr Arg Phe His Lys Ala Val Met Gly Gly Ile Gln Lys Leu
65                  70                  75                  80

Arg Met Leu Ala Lys Asp Gly Leu Phe Thr Ala Tyr His Gly Glu Arg
                85                  90                  95

Gly Trp Gly Ile Ala His Arg Ile Leu Met Pro Ala Phe Gly Pro Leu
            100                 105                 110

Arg Ile Arg Asp Met Phe Glu Asp Met Ser Asp Val Ala Gln Gln Leu
        115                 120                 125

Cys Phe Lys Trp Ala Arg Gln Gly Ser Ser Thr Ser Ile Asn Ile Cys
    130                 135                 140

Asp Asp Phe Thr Arg Leu Thr Leu Asp Thr Ile Ala Leu Cys Thr Met
145                 150                 155                 160

Gly Phe Arg Leu Asn Ser Tyr Tyr Asn Ser Asn Ala Leu His Pro Phe
                165                 170                 175

Ile Glu Ser Met Leu Tyr Val Leu Lys Glu Ala Glu Leu Gln Ser Thr
            180                 185                 190

Leu Pro Gly Val Ala Asn Cys Met Arg Val Lys Ala Gln Arg Arg Met
        195                 200                 205

Ser Lys His Ile Asp Ala Met Arg Ser Met Ala Arg Asn Leu Ile Glu
    210                 215                 220
```

```
Glu Arg Arg Ala Lys Pro Glu Pro Val Asp Asp Leu Leu Asn Thr Leu
225                 230                 235                 240

Leu Asn Gly Arg Asp Pro Ile Thr Gly Glu Gly Met Ser Asp Asp Leu
            245                 250                 255

Ile Ile Ser Asn Ile Ile Thr Phe Leu Ile Ala Gly His Glu Thr Thr
                260                 265                 270

Ser Gly Leu Leu Ser Phe Thr Phe Tyr Tyr Leu Leu Gln Asn Gln Asp
        275                 280                 285

Val Leu Glu Arg Ala Arg Asn Glu Val Asp Glu Val Thr Gly Val Gly
        290                 295                 300

Pro Ile Thr Val Gln His Leu Ala Lys Leu Pro Tyr Ile Asp Ala Ile
305                 310                 315                 320

Met Lys Glu Ser Leu Arg Leu Met Pro Thr Ala Pro Ala Phe Thr Val
                325                 330                 335

Thr Pro Gln Lys Pro Glu Val Leu Gly Gly Lys Trp Met Ile Asn Thr
                340                 345                 350

Gly Asp Ser Val Asn Leu Leu Pro Val Cys Leu Arg Asp Glu Thr
        355                 360                 365

Val Phe Gly Pro Asp Ala Gly Glu Phe Arg Pro Asn Arg Met Leu Glu
370                 375                 380

Glu Asn Phe Ser Lys Leu Pro Pro Asn Ser Trp Lys Pro Phe Gly Asn
385                 390                 395                 400

Gly Glu Arg Gly Cys Ile Gly Arg Ala Phe Ala Trp Gln Glu Ala Gln
            405                 410                 415

Leu Val Val Ala Leu Val Leu Arg Thr Phe Asp Leu Ala Ala Glu Asp
            420                 425                 430

Pro Tyr Tyr Lys Leu Arg Ile Lys Glu Thr Leu Thr Ile Lys Pro Asp
        435                 440                 445

Gly Phe Arg Ile Arg Ala Thr Leu Arg His Gly Lys Ser Ala Thr Ala
    450                 455                 460

Leu Ser Gln Asn Asn Ile Ser Val Gly Ala Ala Ser Pro Ala Ser
465                 470                 475                 480

Ser Thr Tyr Leu Ala Gly Asn Glu Asn Gly Arg Asp Ala Ala Gly Gly
            485                 490                 495

Gln Pro Val Ser Phe Phe Tyr Gly Ser Asn Ser Gly Thr Cys Lys Ala
            500                 505                 510

Leu Thr His Arg Leu Ala Ser Thr Met Met Thr Arg Gly Phe Thr Asp
        515                 520                 525

Gln Asn Ile Ala Pro Leu Asp Ser Ala Val Asp Asn Leu Pro Arg Asp
        530                 535                 540

Gln Pro Thr Ile Ile Thr Thr Thr Tyr Asp Gly Gln Pro Thr Asp
545                 550                 555                 560

Asp Ala Lys Lys Phe Val Ala Trp Leu Glu Ser Gly Asn Ser Pro Ser
            565                 570                 575

Leu Gln Gly Val Ser Tyr Ala Val Phe Gly Cys Gly His Gln Asp Trp
            580                 585                 590

Thr Lys Thr Phe Tyr Arg Ile Pro Ile Leu Ile Asp Ala Leu Met Tyr
        595                 600                 605

Lys Ala Gly Ala Thr Arg Leu Ala Thr Arg Gly Ala Ala Asn Ala Ala
        610                 615                 620

Ile Ser Asp Leu Phe Ser Asp Leu Glu Val Trp Glu Glu Thr Asn Leu
625                 630                 635                 640
```

```
Leu Pro Gly Leu Arg Glu Ser Phe Asn Pro Pro Asn Asn Ser Asn Phe
                645                 650                 655

Val Pro Leu Glu Pro His Gln Leu Gln Ile Ser Ile Asn Lys Pro Thr
            660                 665                 670

Arg Val Gly Met His Arg Asp Leu Ile Glu Ala Lys Val Thr Ala Ile
        675                 680                 685

Arg Thr Leu Thr Ser Pro Gly Ala Pro Glu Lys Arg His Leu Glu Phe
    690                 695                 700

Cys Ile Pro Gly Glu Thr Thr Leu Arg Pro Gly Asp His Leu Asn Ile
705                 710                 715                 720

Leu Pro Val Asn Pro Ser Thr Val Ser Arg Ala Leu Ala Arg Phe
                725                 730                 735

Asn Leu Ala Pro Asp His Ser Ile Thr Phe Glu Ser Ser Asn Ala Leu
            740                 745                 750

Asp Leu Pro Gln Ala Thr Pro Val Ser Ala Ala Glu Leu Phe Ser Ser
        755                 760                 765

Tyr Leu Glu Leu Ser Gln Pro Ala Thr Arg Asn Asn Leu Lys Glu Leu
    770                 775                 780

Ala Ser Thr Thr Pro Ser Asp Gly Glu Lys Gln Glu Leu Leu His Leu
785                 790                 795                 800

Tyr Asp Ser Tyr Asp Ser Leu Ile Arg Ala Lys Arg Ala Ser Val Leu
                805                 810                 815

Asp Leu Leu Glu Gln Phe Thr Ser Val Thr Leu Pro Ile Thr Thr Phe
            820                 825                 830

Ile Ser Met Leu Pro Ala Leu Arg Val Arg Thr Tyr Ser Leu Ser Met
835                 840                 845

Ala Pro Ser Phe Lys Pro Leu His Tyr Ser Leu Thr Phe Ser Val Ile
850                 855                 860

Asn Glu Pro Ala Trp Asn Gly Asn Gly Arg Tyr Leu Gly Val Ala Ser
865                 870                 875                 880

Asn Tyr Leu Ala Ser Leu Asn Leu Gly Ser Ile Leu Tyr Ile Ser Pro
                885                 890                 895

Arg Pro Ala Lys Asp Ala Phe His Leu Pro Thr Asp Gln Ser Ser Lys
            900                 905                 910

Pro Ile Ile Met Ile Cys Ala Gly Ser Gly Leu Ala Pro Phe Arg Ser
        915                 920                 925

Phe Ile Gln Asp Arg Met Leu Trp Gln Gln Asp Lys Thr Leu Ala
    930                 935                 940

Lys Ala Leu Leu Phe Phe Gly Cys Arg Ser Pro Gln Leu Asp Asp Leu
945                 950                 955                 960

Tyr His Asp Glu Leu Ser Gln Phe Glu Ala Ala Gly Val Val Glu Val
                965                 970                 975

Arg Arg Ala Tyr Ser Lys Val Pro Asn His Tyr Leu Ala Lys Gly Cys
            980                 985                 990

Arg Tyr Val Gln His Arg Leu Leu Thr Glu Thr Gly Thr Ile Gln Asp
        995                 1000                1005

Met Trp Ala Gln Asp Ala Ile Ile Tyr Val Cys Gly Ser Gly Asn
    1010                1015                1020

Leu Ala Lys Gly Val Lys Ala Val Leu Glu Ser Met Leu Gly Thr
    1025                1030                1035

Leu Ser Glu Arg Tyr Ile Thr Glu Ile Phe
    1040                1045
```

<210> SEQ ID NO 5
<211> LENGTH: 1050
<212> TYPE: PRT
<213> ORGANISM: Aspergillus niger

<400> SEQUENCE: 5

```
Met Lys Asp Ala Glu Arg Ile Pro Gly Pro Lys Pro Leu Pro Val Val
1               5                   10                  15

Gly Asn Leu Leu Asp Ile Asp Pro Glu His Gly Leu Gln Ser Ile Ile
            20                  25                  30

Ala Phe Ala Asp Lys Tyr Gly Pro Leu Phe Gln Ile Thr Ile Asn Gly
        35                  40                  45

Glu Lys Gln Ile Phe Ala Thr Ser Gln Ala Leu Val Asp Glu Leu Cys
    50                  55                  60

Asp Glu Ser Arg Phe His Lys Ala Val Val Thr Gly Leu Glu Val Leu
65                  70                  75                  80

Arg Leu Leu Ala His Asp Gly Leu Phe Thr Ala Tyr His Gly Glu Arg
                85                  90                  95

Gly Trp Gly Ile Ala His Arg Ile Leu Val Pro Ala Phe Gly Pro Leu
            100                 105                 110

Arg Ile Arg Asn Met Leu Asp Asp Met Ser Asp Val Ala Gln Gln Leu
        115                 120                 125

Cys Leu Lys Trp Ala Arg Gln Gly Gly Ser Thr Ser Ile Asn Ile Thr
    130                 135                 140

Glu Asp Phe Thr Arg Leu Thr Leu Asp Thr Ile Ala Leu Cys Thr Met
145                 150                 155                 160

Gly Phe Arg Leu Asn Ser Phe Tyr Asn Asn Glu Thr Met His Pro Phe
                165                 170                 175

Val Gln Ser Met Leu Tyr Val Leu Lys Glu Ala Asp Val Gln Ala Asn
            180                 185                 190

Leu Pro Gly Ile Ala Asn Ser Ile Arg Val Ser Ala Gln Arg Arg Met
        195                 200                 205

His Lys Asn Ile Glu Ala Met Arg Thr Met Ala Arg Gly Ile Ile Gln
    210                 215                 220

Glu Arg Arg Lys Asn Lys Asn Pro Val Asp Asp Ile Leu Asn Thr Leu
225                 230                 235                 240

Leu Asn Gly Arg Asp Pro Val Thr Gly Glu Gly Met Ser Asp Asp Ser
                245                 250                 255

Ile Ile Asp Asn Val Ile Thr Phe Leu Ile Ala Gly His Glu Thr Thr
            260                 265                 270

Ser Gly Leu Leu Ser Phe Thr Phe Tyr Phe Leu Ile Gln His Pro His
        275                 280                 285

Ile Leu Lys Lys Ala Gln Glu Glu Val Asp Glu Thr Val Gly Leu Ala
    290                 295                 300

Gln Ile Ser Ala Gln His Leu Ala Glu Leu Pro Tyr Ile Asp Ala Ile
305                 310                 315                 320

Leu Lys Glu Ser Leu Arg Leu Met Pro Thr Ala Pro Gly Phe Ala Val
                325                 330                 335

Thr Pro Lys Lys Thr Glu Val Leu Gly Gly Lys Trp Met Ile Asn Ala
            340                 345                 350

Gly Gln Pro Val Asn Val Leu Leu Pro Ala Cys Leu Arg Asp Gln Ser
        355                 360                 365

Val Phe Gly Pro Asp Ala Asp Glu Phe His Pro Glu Arg Met Leu Ala
    370                 375                 380
```

-continued

```
Glu Asn Phe Ser Lys Leu Pro Pro Asn Ser Trp Lys Pro Phe Gly Asn
385                 390                 395                 400
Gly Glu Arg Gly Cys Ile Gly Arg Ala Phe Ala Trp Gln Glu Ala Gln
                405                 410                 415
Leu Val Val Ala Met Ile Leu Gln Thr Phe Asp Leu Val Pro Asp Asp
            420                 425                 430
Pro Ser Tyr Gln Leu Arg Ile Lys Glu Thr Leu Thr Ile Lys Pro Asp
        435                 440                 445
Gly Phe Arg Ile Arg Ala Leu Leu Arg Arg Gly Gln Thr Ala Thr Gly
    450                 455                 460
Leu Ser Arg Arg Ser Met Leu Val Ala Arg Asp Gly Ser Ser Gly Glu
465                 470                 475                 480
Ser Ser Asn His Leu Ala Glu Ala Arg Gly Asp His Ala Pro Ala Arg
                485                 490                 495
Gly Gln Pro Val Ser Phe Phe Tyr Gly Ser Asn Ser Gly Thr Cys Lys
            500                 505                 510
Ala Leu Ala His Gln Leu Ala Ser Asn Met Met Ser Arg Gly Tyr Thr
        515                 520                 525
Thr Gln Lys Leu Ala Pro Leu Asp Asn Ala Val Gly Asn Leu Pro Arg
    530                 535                 540
Asp Gln Pro Val Ile Ile Leu Thr Thr Thr Tyr Asp Gly Gln Pro Thr
545                 550                 555                 560
Asp Asp Ala Lys Lys Phe Val Ala Trp Leu Glu Gly Asn Val Pro
                565                 570                 575
Ser Leu Gln Gly Ile Ser Tyr Ala Val Phe Gly Cys Gly His His Asp
            580                 585                 590
Trp Thr Gln Thr Phe Tyr Arg Ile Pro Ile Leu Ile Asp Asp Leu Met
        595                 600                 605
His Lys Ala Gly Ala Thr Arg Leu Ala Pro Arg Gly Ala Ala Asn Ala
    610                 615                 620
Ala Val Ser Asp Leu Phe Ser Asp Leu Glu Ala Trp Glu Glu Thr Ser
625                 630                 635                 640
Leu Leu Pro Ala Leu Arg Glu Asn Phe Leu Pro Ser Asn Ser Thr Asp
                645                 650                 655
Phe Asp Pro Leu Asn Pro His Gln Ile Gln Leu Ser Leu Ser Lys Pro
            660                 665                 670
Arg Arg Val Asp Leu His Lys Gly Leu Ile Glu Ala Lys Val Thr Ala
        675                 680                 685
Val Arg Val Leu Thr Ser Pro Asp Thr Pro Glu Lys Arg His Leu Glu
    690                 695                 700
Phe Cys Phe Gln Gly Asp Thr Ser Leu Arg Pro Gly Asp His Leu Asn
705                 710                 715                 720
Ile Leu Pro Val Asn Pro Ser Thr Val Ser Arg Val Leu Ala Gln
                725                 730                 735
Phe Asn Leu Ala Pro Asp Tyr Asn Ile Thr Val Asn Ser Phe Asn Thr
            740                 745                 750
Leu Gly Leu Pro Gln Ala Thr Pro Val Ser Ala Ser Glu Leu Phe Ser
        755                 760                 765
Ser Tyr Val Glu Leu Cys Gln Pro Ala Thr Arg Asn Asn Leu Lys Ala
    770                 775                 780
Leu Ile Ala Ala Thr Gln Ser Asp Pro Asp Lys Gln Glu Leu Asn Arg
785                 790                 795                 800
Leu Tyr Asp Ser Tyr Glu Phe Ile Val Arg Asp Lys Arg Val Ser Val
```

```
        805                 810                 815
Leu Asp Leu Leu Glu Gln Phe Pro Ser Ile Ser Leu Pro Ile Ala Ala
        820                 825                 830

Phe Ile Ser Met Leu Pro Ala Leu Arg Val Arg Thr Tyr Ser Leu Ser
        835                 840                 845

Met Ala Pro Ser Phe Lys Pro Ser His Ser Ser Leu Thr Phe Ser Val
        850                 855                 860

Ile Asn Glu Pro Ala Trp Arg Gly Ser Gly Gln His Leu Gly Val Ala
865                 870                 875                 880

Ser Asn Tyr Leu Ala Ser Leu Thr Ser Gly Ser Ile Phe Tyr Phe Ser
                885                 890                 895

Pro Arg Pro Ala Lys Glu Ser Phe His Leu Pro Lys Asp Pro Ser Asn
                900                 905                 910

Thr Pro Ile Ile Met Ile Cys Ala Gly Ser Gly Leu Ala Pro Phe Leu
                915                 920                 925

Ser Phe Ile Gln Asp Arg Met Val Leu Lys Gln Gln Tyr Lys Pro Leu
        930                 935                 940

Ala Lys Ala Phe Leu Phe Phe Gly Cys Arg Gly Arg Ser Leu Asp Asp
945                 950                 955                 960

Leu Tyr His Glu Glu Leu Ser Glu Phe Glu Ala Ala Gly Val Val Glu
                965                 970                 975

Ile Arg Arg Ala Tyr Ser Lys Thr Pro Asp Phe Asp Ile Ala Lys Gly
        980                 985                 990

Cys Arg Tyr Val Gln His Arg Leu  Val Thr Glu Gly Gln  Ala Ile Leu
        995                 1000                1005

Ser Leu  Trp Ser Gln Asn Ala  Thr Ile Tyr Val Cys  Gly Ser Thr
        1010                1015                1020

Asn Met  Ala Lys Gly Val Glu  Ala Val Leu Gln Asn  Met Leu Gly
        1025                1030                1035

Pro Leu  Pro Lys Glu Arg Tyr  Val Thr Glu Ile Phe
        1040                1045                1050

<210> SEQ ID NO 6
<211> LENGTH: 1049
<212> TYPE: PRT
<213> ORGANISM: Penicillium camemberti

<400> SEQUENCE: 6

Met Lys Asp Met Asp Cys Ile Pro Gly Pro Lys Pro Leu Pro Val Val
1               5                   10                  15

Gly Asn Leu Phe Asp Leu Asp Leu Asn Ala Leu Gln Ser Ile Ile
                20                  25                  30

Arg Met Ala Asp Glu Phe Gly Pro Leu Phe Gln Ile Thr Ile Asn Gly
        35                  40                  45

Gln Lys Gln Ile Phe Ala Thr Ser Gln Ala Leu Val Asp Glu Leu Cys
    50                  55                  60

Asp Glu Thr Arg Phe His Lys Ala Val Met Gly Val Glu Lys Leu
65                  70                  75                  80

Arg Met Leu Ala Gln Asp Gly Leu Phe Thr Ala His His Gly Glu Arg
                85                  90                  95

Gly Trp Gly Ile Ala His Arg Ile Leu Met Pro Ala Phe Gly Pro Leu
                100                 105                 110

Arg Ile Arg Asp Met Phe Glu Asp Met Ser Asp Val Ala His Gln Leu
        115                 120                 125
```

```
Cys Phe Lys Trp Ala Arg Gln Gly Ser Ser Ala Ser Ile Asn Ile Ala
    130                 135                 140

Glu Asp Phe Thr Arg Leu Thr Leu Asp Thr Ile Ala Leu Cys Thr Met
145                 150                 155                 160

Ser Phe Arg Leu Asn Ser Tyr Tyr Asn Ser Glu Thr Met His Pro Phe
                165                 170                 175

Val Gln Ser Met Leu Tyr Val Leu Lys Glu Ala Asp Leu Gln Ala Thr
                180                 185                 190

Leu Pro Gly Val Ala Asn Cys Val Arg Val Lys Ala Gln Arg Arg Met
                195                 200                 205

Ser Lys His Ile Gln Ala Met Arg Asn Ile Ala Gly Asp Ile Ile Lys
    210                 215                 220

Gly Arg Arg Asp Lys Pro Glu Pro Val Asp Asp Leu Leu Asn Thr Leu
225                 230                 235                 240

Leu Asn Gly Arg Asp Pro Val Thr Gly Glu Gly Met Ser Asp Glu Leu
                245                 250                 255

Ile Ile Ser Asn Ile Ile Thr Phe Leu Val Ala Gly His Glu Thr Thr
                260                 265                 270

Ser Gly Leu Leu Ser Phe Thr Phe Tyr Tyr Leu Leu Gln His Pro His
    275                 280                 285

Val Leu Glu Gln Ala Arg Asn Glu Val Asp Glu Val Val Gly Val Gly
290                 295                 300

Pro Ile Thr Val Gln His Leu Ala Lys Leu Pro Tyr Ile Asp Ala Val
305                 310                 315                 320

Met Lys Glu Ser Leu Arg Leu Met Pro Thr Ala Pro Ala Phe Thr Val
                325                 330                 335

Thr Pro Lys Lys Pro Glu Val Val Gly Gly Lys Trp Met Val Asn Thr
                340                 345                 350

Gly Gln Ser Val His Val Leu Leu Pro Val Cys Leu Arg Asp Glu Ala
                355                 360                 365

Val Phe Gly Pro Asp Ala Gly Glu Phe Arg Pro Thr Arg Met Leu Glu
    370                 375                 380

Glu Asn Phe Ser Lys Leu Pro Pro Asn Ser Trp Lys Pro Phe Gly Asn
385                 390                 395                 400

Gly Glu Arg Gly Cys Ile Gly Arg Ala Phe Ala Trp Gln Glu Ala Gln
                405                 410                 415

Leu Val Val Ala Ser Val Leu Gln Thr Phe Asp Leu Val Ala Glu Asp
                420                 425                 430

Pro Tyr Tyr Lys Leu Arg Ile Lys Glu Thr Leu Thr Ile Lys Pro Asp
                435                 440                 445

Gly Phe Arg Val Arg Ala Thr Leu Arg Arg Gly Gln Ser Ala Thr Ala
    450                 455                 460

Leu Ser Gln His Asn Met Ser Ala Gly Ala Thr Ala Ser Pro Gly Ser
465                 470                 475                 480

Ser Thr His Leu Ala Gly Asp Glu Asn Gly Gln Asp Thr Ala Gly Gly
                485                 490                 495

Gln Pro Ile Ser Phe Phe Tyr Gly Ser Asn Ser Gly Thr Cys Lys Ala
                500                 505                 510

Leu Ala His Arg Leu Ala Ser Thr Met Met Thr Arg Gly Phe Thr Asp
                515                 520                 525

Gln His Leu Ala Gln Leu Asp Ser Ala Val Asp Asn Leu Pro Arg Asp
    530                 535                 540

Gln Pro Thr Ile Ile Val Thr Thr Thr Tyr Asp Gly Gln Pro Thr Asp
```

```
               545                 550                 555                 560
Asp Ala Lys Lys Phe Leu Ala Trp Leu Glu Ser Gly Asn Val Pro Ser
                565                 570                 575

Leu His Gly Val Ser Tyr Ala Val Phe Gly Cys Gly His Gln Asp Trp
                580                 585                 590

Thr Lys Thr Phe Tyr Arg Ile Pro Ile Leu Ile Asp Asp Leu Met His
                595                 600                 605

Lys Ala Gly Ala Thr Arg Leu Thr Thr Arg Gly Thr Ala Asn Ala Ala
                610                 615                 620

Val Ser Asp Leu Phe Ser Asp Leu Glu Val Trp Glu Glu Thr Asn Leu
625                 630                 635                 640

Leu Pro Ala Leu Arg Glu Lys Phe Tyr Leu Cys Asn Ser Ser Asp Phe
                645                 650                 655

Glu Pro Leu Asp Pro His Gln Leu Gln Ile Ser Ile Ser Lys Pro Ala
                660                 665                 670

Arg Val Gly Met His Arg Asp Leu Val Glu Gly Lys Val Thr Ala Ile
                675                 680                 685

Arg Thr Leu Thr Ser Pro Gly Val Pro Glu Lys Arg His Val Glu Phe
                690                 695                 700

Gln Ile Pro Ser Glu Met Ala Leu Arg Pro Gly Asp His Val Asn Ile
705                 710                 715                 720

Leu Pro Val Asn Pro Pro Cys Ser Val Leu Arg Ala Leu Ala Arg Phe
                725                 730                 735

Ser Leu Ala Ser Asp His Ser Ile Thr Phe Glu Ser Ser Asn Ala Leu
                740                 745                 750

Asp Leu Pro Gln Ala Thr Pro Val Ser Ala Ala Glu Leu Phe Ser Ser
                755                 760                 765

Tyr Leu Glu Leu Ser Gln Pro Ala Thr Arg Ile Asn Leu Lys Ser Leu
                770                 775                 780

Ala Ser Ala Thr Pro Ser Asp Asp Lys Lys Glu Leu Leu His Phe
785                 790                 795                 800

His Asp Ser Tyr Asp Ser Leu Ile Arg Asp Lys Arg Val Ser Val Leu
                805                 810                 815

Asp Leu Leu Glu His Phe Thr Ser Ile Thr Leu Pro Ile Ala Thr Phe
                820                 825                 830

Ile Ser Met Leu Pro Val Leu Arg Val Arg Thr Tyr Ser Leu Ser Met
                835                 840                 845

Ala Pro Ser Phe Lys Pro Leu His Cys Ser Leu Thr Phe Ser Val Val
                850                 855                 860

Asn Glu Pro Ala Trp Ser Gly Asn Gly Arg Tyr Leu Gly Val Gly Ser
865                 870                 875                 880

Asn Tyr Leu Ala Ser Leu Thr Pro Gly Ser Ile Leu Tyr Val Ser Pro
                885                 890                 895

Arg Pro Ala Lys Asp Ala Phe His Leu Pro Thr Asp Gln Ser Ser Asn
                900                 905                 910

Pro Ile Ile Met Ile Cys Ala Gly Ser Gly Leu Ala Pro Phe Arg Ser
                915                 920                 925

Phe Ile Gln Asp Arg Met Ala Trp Leu Gln Gln Gly Lys Pro Leu Ala
                930                 935                 940

Lys Ala Leu Leu Phe Phe Gly Cys Arg Gly Pro His Leu Asp Asp Leu
945                 950                 955                 960

Tyr His Asp Glu Leu Ser Glu Phe Glu Ser Ala Gly Val Val Glu Val
                965                 970                 975
```

```
Arg Arg Ala Tyr Ser Lys Val Pro Asn His Tyr Leu Ala Lys Gly Cys
            980                 985                 990

Arg Tyr Ala Gln His Arg Leu Leu  Thr Glu Thr Glu Thr  Ile Gln Asp
            995                 1000                1005

Met Trp  Ala His Asn Ala Thr  Leu Tyr Leu Cys Gly  Ser Ala Asn
    1010                 1015                 1020

Leu Ala  Lys Gly Val Lys Ala  Val Leu Glu Asn Met  Leu Gly Thr
    1025                 1030                 1035

Leu Ser  Glu Glu Arg Tyr Ile  Thr Glu Ile Phe
    1040                 1045

<210> SEQ ID NO 7
<211> LENGTH: 1049
<212> TYPE: PRT
<213> ORGANISM: Penicillium freii

<400> SEQUENCE: 7

Met Lys Asp Met Asp Cys Ile Pro Gly Pro Lys Pro Leu Pro Val Val
1               5                   10                  15

Gly Asn Leu Phe Asp Leu Asp Leu Asp Asn Ala Leu Gln Ser Ile Ile
            20                  25                  30

Lys Met Ala Asp Glu Phe Gly Pro Leu Phe Gln Ile Thr Val Asn Arg
        35                  40                  45

Gln Lys His Ile Phe Ala Thr Ser Gln Ala Leu Val Asp Glu Leu Cys
    50                  55                  60

Asp Glu Thr Arg Phe His Lys Ala Val Ile Gly Gly Val Glu Lys Leu
65                  70                  75                  80

Arg Met Leu Ala His Asp Gly Leu Phe Thr Ala His His Gly Glu Arg
                85                  90                  95

Gly Trp Gly Ile Ala His Arg Ile Leu Met Pro Ala Phe Gly Pro Leu
            100                 105                 110

Arg Ile Arg Asp Met Phe Glu Asp Met Ser Asp Val Ala His Gln Leu
        115                 120                 125

Cys Phe Lys Trp Ala Arg Gln Gly Ser Ser Thr Ser Ile Asn Ile Ser
    130                 135                 140

Glu Asp Phe Thr Arg Leu Thr Leu Asp Thr Ile Ala Leu Cys Thr Met
145                 150                 155                 160

Ser Phe Arg Leu Asn Ser Tyr Tyr Asn Ser Asp Thr Met His Pro Phe
                165                 170                 175

Val Gln Ser Met Leu Tyr Val Leu Lys Glu Ala Asp Leu Gln Ser Ser
            180                 185                 190

Leu Pro Glu Val Ala Asn Cys Val Arg Val Lys Ala Gln Arg Ser Met
        195                 200                 205

Ser Lys His Ile Glu Ala Met Arg Ser Ile Ala Gly Asp Ile Ile Lys
    210                 215                 220

Gly Arg Arg Asp Lys Pro Glu Pro Val Asn Asp Leu Leu Asn Thr Leu
225                 230                 235                 240

Leu Asn Gly Arg Asp Pro Val Thr Gly Glu Gly Met Ser Asp Glu Leu
                245                 250                 255

Ile Ile Ser Asn Ile Ile Thr Phe Leu Ile Ala Gly His Glu Thr Thr
            260                 265                 270

Ser Gly Leu Leu Ser Phe Thr Phe Tyr Tyr Leu Leu Gln His Pro Gln
        275                 280                 285

Val Leu Glu Gln Ala Arg Asn Glu Val Asp Glu Val Val Gly Val Gly
```

```
            290                 295                 300
Pro Ile Thr Val Gln His Leu Ala Lys Leu Pro Tyr Ile Asp Ala Ile
305                 310                 315                 320

Met Lys Glu Ser Leu Arg Leu Met Pro Thr Ala Pro Ser Phe Thr Val
                325                 330                 335

Thr Pro Lys Lys Pro Glu Val Leu Gly Gly Lys Trp Met Ile Asn Pro
                340                 345                 350

Gly Gln Ser Val His Val Leu Leu Pro Val Cys Leu Arg Asp Glu Ala
                355                 360                 365

Val Phe Gly Pro Asp Ala Gly Glu Phe Arg Pro Asn Arg Met Leu Glu
            370                 375                 380

Glu Asn Phe Ser Lys Leu Pro Pro Asn Ser Trp Lys Pro Phe Gly Asn
385                 390                 395                 400

Gly Glu Arg Gly Cys Ile Gly Arg Ala Phe Ala Trp Gln Glu Ala Gln
                405                 410                 415

Leu Val Val Ala Ser Val Leu Gln Thr Phe Asp Leu Val Ala Glu Asp
                420                 425                 430

Pro Asn Tyr Lys Leu Arg Val Lys Glu Thr Leu Thr Ile Lys Pro Asp
                435                 440                 445

Gly Phe Arg Val Arg Ala Thr Leu Arg His Gly Arg Ser Ala Thr Ala
            450                 455                 460

Leu Ser Gln His Asn Met Ser Ala Gly Ala Thr Ser Ser Pro Gly Ser
465                 470                 475                 480

Ser Ala His Pro Ala Gly Asn Lys Asn Ala Gln Asp Ala Ala Gly Gly
                485                 490                 495

Gln Ser Ile Ser Phe Phe Tyr Gly Ser Asn Ser Gly Thr Cys Lys Ala
                500                 505                 510

Leu Ala His Arg Leu Ala Ser Thr Met Met Thr Arg Gly Phe Thr Asp
                515                 520                 525

Gln His Leu Ala Pro Leu Asp Ser Ala Val Asp Asn Leu Pro Lys Asp
            530                 535                 540

Gln Pro Thr Ile Ile Val Thr Thr Tyr Glu Gly Gln Pro Thr Asp
545                 550                 555                 560

Asp Ala Lys Lys Phe Leu Ala Trp Leu Glu Ser Gly Ile Val Pro Ser
                565                 570                 575

Leu His Gly Val Ser Tyr Ala Val Phe Gly Cys Gly His Gln Asp Trp
                580                 585                 590

Thr Lys Thr Phe Tyr Arg Ile Pro Ile Leu Ile Asp Asp Leu Met His
                595                 600                 605

Lys Ala Gly Ala Thr Arg Leu Thr Thr Arg Gly Glu Ala Asn Ala Ala
            610                 615                 620

Val Ser Asp Leu Phe Ser Asp Leu Glu Val Trp Glu Glu Thr Asn Leu
625                 630                 635                 640

Leu Pro Ala Leu Arg Glu Lys Phe Asp Ala Ser Asn Ser Gly Glu Phe
                645                 650                 655

Glu Ser Leu Asp Leu Gln Gln Leu Gln Ile Ser Ile Ser Lys Pro Thr
                660                 665                 670

Arg Val Gly Met His Arg Asp Leu Ile Glu Gly Lys Val Thr Ala Ile
                675                 680                 685

Arg Thr Leu Thr Ser Pro Gly Val Pro Glu Lys Arg His Val Glu Phe
            690                 695                 700

Gln Ile Thr Ser Asp Thr Thr Leu Arg Pro Gly Asp His Val Asn Ile
705                 710                 715                 720
```

```
Leu Pro Val Asn Pro Ser Thr Val Leu Arg Ala Leu Ala Arg Phe
            725                 730                 735

Asn Leu Ala Ser Asp His Ile Ile Thr Phe Glu Ser Ser Asn Ala Leu
        740                 745                 750

Asp Leu Pro Gln Ala Thr Pro Val Ser Ala Ala Glu Leu Phe Gly Ser
    755                 760                 765

Tyr Leu Glu Leu Ser Gln Pro Ala Thr Arg Asn Asn Leu Lys Ser Leu
770                 775                 780

Ala Ser Thr Thr Pro Ser Asp Glu Asp Lys Gln Glu Leu Leu Arg Phe
785                 790                 795                 800

His Asp Ser Tyr Asp Ser Leu Ile Arg Asp Lys Arg Val Ser Val Leu
                805                 810                 815

Asp Leu Leu Glu His Phe Thr Ser Ile Thr Leu Pro Ile Ala Thr Phe
            820                 825                 830

Ile Ser Met Leu Pro Val Leu Arg Val Arg Thr Tyr Ser Leu Ser Met
        835                 840                 845

Ala Pro Ser Phe Lys Pro Leu His Cys Ser Leu Thr Phe Ser Val Val
    850                 855                 860

Asn Glu Pro Ala Trp Ser Gly Asn Gly Arg Tyr Leu Gly Val Gly Ser
865                 870                 875                 880

Asn Tyr Leu Ala Ser Leu Thr Pro Gly Ser Ile Leu Tyr Val Ser Pro
                885                 890                 895

Arg Pro Ala Lys Glu Ala Phe His Leu Pro Ala Asp Gln Ser Ser Lys
            900                 905                 910

Pro Ile Ile Met Ile Cys Ala Gly Ser Gly Leu Ala Pro Phe Arg Ser
        915                 920                 925

Phe Ile Gln Asp Arg Met Ala Trp Leu Gln Gln Gly Lys Pro Leu Ala
    930                 935                 940

Lys Ala Leu Leu Phe Phe Gly Cys Arg Gly Pro Gln Leu Asp Asp Leu
945                 950                 955                 960

Tyr His Asp Glu Leu Ser Glu Phe Glu Ser Ala Gly Val Val Glu Val
                965                 970                 975

Arg Arg Ala Tyr Ser Lys Val Pro Asn His Tyr Pro Gly Lys Gly Cys
            980                 985                 990

Arg Tyr Val Gln His Arg Leu Phe Ala Glu Thr Glu Thr Ile Gln Asp
        995                 1000                1005

Met Trp Ala His Asn Ala Thr Leu Tyr Leu Cys Gly Ser Ala Thr
    1010                1015                1020

Leu Ala Lys Gly Val Lys Ala Thr Leu Glu Asn Met Leu Gly Thr
    1025                1030                1035

Leu Ser Glu Glu Arg Tyr Ile Thr Glu Ile Phe
    1040                1045

<210> SEQ ID NO 8
<211> LENGTH: 1066
<212> TYPE: PRT
<213> ORGANISM: Fusarium oxysporum

<400> SEQUENCE: 8

Met Ala Glu Ser Val Pro Ile Pro Glu Pro Pro Gly Tyr Pro Leu Ile
1               5                   10                  15

Gly Asn Leu Gly Glu Phe Thr Ser Asn Pro Leu Ser Asp Leu Asn Arg
            20                  25                  30

Leu Ala Asp Thr Tyr Gly Pro Ile Phe Arg Leu Arg Leu Gly Ala Lys
```

```
                 35                  40                  45
Ala Pro Ile Phe Val Ser Ser Asn Ser Leu Ile Asn Glu Val Cys Asp
 50                  55                  60

Glu Lys Arg Phe Lys Lys Thr Leu Lys Ser Val Leu Ser Gln Val Arg
 65                  70                  75                  80

Glu Gly Val His Asp Gly Leu Phe Thr Ala Phe Glu Asp Glu Pro Asn
                 85                  90                  95

Trp Gly Lys Ala His Arg Ile Leu Val Pro Ala Phe Gly Pro Leu Ser
                100                 105                 110

Ile Arg Gly Met Phe Pro Glu Met His Asp Ile Ala Thr Gln Leu Cys
                115                 120                 125

Met Lys Phe Ala Arg His Gly Pro Arg Thr Pro Ile Asp Thr Ser Asp
130                 135                 140

Asn Phe Thr Arg Leu Ala Leu Asp Thr Leu Ala Leu Cys Ala Met Asp
145                 150                 155                 160

Phe Arg Phe Tyr Ser Tyr Tyr Lys Glu Glu Leu His Pro Phe Ile Glu
                165                 170                 175

Ala Met Gly Asp Phe Leu Thr Glu Ser Gly Asn Arg Asn Arg Arg Pro
                180                 185                 190

Pro Phe Ala Pro Asn Phe Leu Tyr Arg Ala Ala Asn Glu Lys Phe Tyr
                195                 200                 205

Gly Asp Ile Ala Leu Met Lys Ser Val Ala Asp Glu Val Val Ala Ala
210                 215                 220

Arg Lys Ala Ser Pro Ser Asp Arg Lys Asp Leu Leu Ala Ala Met Leu
225                 230                 235                 240

Asn Gly Val Asp Pro Gln Thr Gly Glu Lys Leu Ser Asp Glu Asn Ile
                245                 250                 255

Thr Asn Gln Leu Ile Thr Phe Leu Ile Ala Gly His Glu Thr Thr Ser
                260                 265                 270

Gly Thr Leu Ser Phe Ala Met Tyr Gln Leu Leu Lys Asn Pro Glu Ala
                275                 280                 285

Tyr Ser Lys Val Gln Lys Glu Val Asp Glu Val Val Gly Arg Gly Pro
290                 295                 300

Val Leu Val Glu His Leu Thr Lys Leu Pro Tyr Ile Ser Ala Val Leu
305                 310                 315                 320

Arg Glu Thr Leu Arg Leu Asn Ser Pro Ile Thr Ala Phe Gly Leu Glu
                325                 330                 335

Ala Ile Asp Asp Thr Phe Leu Gly Gly Lys Tyr Leu Val Lys Lys Gly
                340                 345                 350

Glu Ile Val Thr Ala Leu Leu Ser Arg Gly His Val Asp Pro Val Val
                355                 360                 365

Tyr Gly Asn Asp Ala Asp Lys Phe Ile Pro Glu Arg Met Leu Asp Asp
                370                 375                 380

Glu Phe Ala Arg Leu Asn Lys Glu Tyr Pro Asn Cys Trp Lys Pro Phe
385                 390                 395                 400

Gly Asn Gly Lys Arg Ala Cys Ile Gly Arg Pro Phe Ala Trp Gln Glu
                405                 410                 415

Ser Leu Leu Ala Met Val Val Leu Phe Gln Asn Phe Asn Phe Thr Met
                420                 425                 430

Thr Asp Pro Asn Tyr Ala Leu Glu Ile Lys Gln Thr Leu Thr Ile Lys
                435                 440                 445

Pro Asp His Phe Tyr Ile Asn Ala Thr Leu Arg His Gly Met Thr Pro
                450                 455                 460
```

```
Thr Glu Leu Glu His Val Leu Ala Gly Asn Gly Ala Thr Ser Ser Ser
465                 470                 475                 480

Thr His Asn Ile Lys Ala Ala Asn Leu Asp Ala Lys Ala Gly Ser
            485                 490                 495

Gly Lys Pro Met Ala Ile Phe Tyr Gly Ser Asn Ser Gly Thr Cys Glu
            500                 505                 510

Ala Leu Ala Asn Arg Leu Ala Ser Asp Ala Pro Ser His Gly Phe Ser
            515                 520                 525

Ala Thr Thr Val Gly Pro Leu Asp Gln Ala Lys Gln Asn Leu Pro Glu
530                 535                 540

Asp Arg Pro Val Val Ile Val Thr Ala Ser Tyr Glu Gly Gln Pro Pro
545                 550                 555                 560

Ser Asn Ala Ala His Phe Ile Lys Trp Met Glu Asp Leu Asp Gly Asn
                565                 570                 575

Asp Met Glu Lys Val Ser Tyr Ala Val Phe Ala Cys Gly His His Asp
            580                 585                 590

Trp Val Glu Thr Phe His Arg Ile Pro Lys Leu Val Asp Ser Thr Leu
            595                 600                 605

Glu Lys Arg Gly Gly Thr Arg Leu Val Pro Met Gly Ser Ala Asp Ala
610                 615                 620

Ala Thr Ser Asp Met Phe Ser Asp Phe Glu Ala Trp Glu Asp Ile Val
625                 630                 635                 640

Leu Trp Pro Gly Leu Lys Glu Lys Tyr Lys Ile Ser Asp Glu Glu Ser
                645                 650                 655

Gly Gly Gln Lys Gly Leu Leu Val Glu Val Ser Thr Pro Arg Lys Thr
            660                 665                 670

Ser Leu Arg Gln Asp Val Glu Glu Ala Leu Val Val Ala Glu Lys Thr
            675                 680                 685

Leu Thr Lys Ser Gly Pro Ala Lys Lys His Ile Glu Ile Gln Leu Pro
690                 695                 700

Ser Ala Met Thr Tyr Lys Ala Gly Asp Tyr Leu Ala Ile Leu Pro Leu
705                 710                 715                 720

Asn Pro Lys Ser Thr Val Ala Arg Val Phe Arg Arg Phe Ser Leu Ala
                725                 730                 735

Trp Asp Ser Phe Leu Lys Ile Gln Ser Glu Gly Pro Thr Thr Leu Pro
            740                 745                 750

Thr Asn Val Ala Ile Ser Ala Phe Asp Val Phe Ser Ala Tyr Val Glu
            755                 760                 765

Leu Ser Gln Pro Ala Thr Lys Arg Asn Ile Leu Ala Leu Ala Glu Ala
770                 775                 780

Thr Glu Asp Lys Asp Thr Ile Gln Glu Leu Glu Arg Leu Ala Gly Asp
785                 790                 795                 800

Ala Tyr Gln Ala Glu Ile Ser Pro Lys Arg Val Ser Val Leu Asp Leu
                805                 810                 815

Leu Glu Lys Phe Pro Ala Val Ala Leu Pro Ile Ser Ser Tyr Leu Ala
            820                 825                 830

Met Leu Pro Pro Met Arg Val Arg Gln Tyr Ser Ile Ser Ser Ser Pro
            835                 840                 845

Phe Ala Asp Pro Ser Lys Leu Thr Leu Thr Tyr Ser Leu Leu Asp Ala
850                 855                 860

Pro Ser Leu Ser Gly Gln Gly Arg His Val Gly Val Ala Thr Asn Phe
865                 870                 875                 880
```

```
Leu Ser His Leu Thr Ala Gly Asp Lys Leu His Val Ser Val Arg Ala
                885                 890                 895

Ser Ser Glu Ala Phe His Leu Pro Ser Asp Ala Glu Lys Thr Pro Ile
            900                 905                 910

Ile Cys Val Ala Ala Gly Thr Gly Leu Ala Pro Leu Arg Gly Phe Ile
            915                 920                 925

Gln Glu Arg Ala Ala Met Leu Ala Ala Gly Arg Thr Leu Ala Pro Ala
        930                 935                 940

Leu Leu Phe Phe Gly Cys Arg Asn Pro Glu Ile Asp Asp Leu Tyr Ala
945                 950                 955                 960

Glu Glu Phe Glu Arg Trp Glu Lys Met Gly Ala Val Asp Val Arg Arg
                965                 970                 975

Ala Tyr Ser Arg Ala Thr Asp Lys Ser Glu Gly Cys Lys Tyr Val Gln
            980                 985                 990

Asp Arg Val Tyr His Asp Arg Ala Asp Val Phe Lys Val Trp Asp Gln
            995                 1000                1005

Gly Ala Lys Val Phe Ile Cys Gly Ser Arg Glu Ile Gly Lys Ala
        1010                1015                1020

Val Glu Asp Val Cys Val Arg Leu Ala Ile Glu Lys Ala Gln Gln
        1025                1030                1035

Asn Gly Arg Asp Val Thr Glu Glu Met Ala Arg Ala Trp Phe Glu
        1040                1045                1050

Arg Ser Arg Asn Glu Arg Phe Ala Thr Asp Val Phe Asp
        1055                1060                1065

<210> SEQ ID NO 9
<211> LENGTH: 1054
<212> TYPE: PRT
<213> ORGANISM: Aspergillus oryzae

<400> SEQUENCE: 9

Met Arg Gln Asn Asp Asn Glu Lys Gln Ile Cys Pro Ile Pro Gly Pro
1               5                   10                  15

Gln Gly Leu Pro Phe Leu Gly Asn Ile Leu Asp Ile Asp Leu Asp Asn
                20                  25                  30

Gly Thr Met Ser Thr Leu Lys Ile Ala Lys Thr Tyr Tyr Pro Ile Phe
            35                  40                  45

Lys Phe Thr Phe Ala Gly Glu Thr Ser Ile Val Ile Asn Ser Val Ala
        50                  55                  60

Leu Leu Ser Glu Leu Cys Asp Glu Thr Arg Phe His Lys His Val Ser
65                  70                  75                  80

Phe Gly Leu Glu Leu Leu Arg Ser Gly Thr His Asp Gly Leu Phe Thr
                85                  90                  95

Ala Tyr Asp His Glu Lys Asn Trp Gly Leu Ala His Arg Leu Leu Val
            100                 105                 110

Pro Ala Phe Gly Pro Leu Arg Ile Arg Glu Met Phe Pro Gln Met His
        115                 120                 125

Asp Ile Ala Gln Gln Leu Cys Leu Lys Trp Gln Arg Tyr Gly Pro Arg
    130                 135                 140

Arg Pro Leu Asn Leu Val Asp Asp Phe Thr Arg Thr Thr Leu Asp Thr
145                 150                 155                 160

Ile Ala Leu Cys Ala Met Gly Tyr Arg Phe Asn Ser Phe Tyr Ser Glu
                165                 170                 175

Gly Asp Phe His Pro Phe Ile Lys Ser Met Val Arg Phe Leu Lys Glu
            180                 185                 190
```

```
Ala Glu Thr Gln Ala Thr Leu Pro Ser Phe Ile Ser Asn Leu Arg Val
            195                 200                 205

Arg Ala Lys Arg Arg Thr Gln Leu Asp Ile Asp Leu Met Arg Thr Val
    210                 215                 220

Cys Arg Glu Ile Val Thr Glu Arg Arg Gln Thr Asn Leu Asp His Lys
225                 230                 235                 240

Asn Asp Leu Leu Asp Thr Met Leu Thr Ser Arg Asp Ser Leu Ser Gly
                245                 250                 255

Asp Ala Leu Ser Asp Glu Ser Ile Ile Asp Asn Ile Leu Thr Phe Leu
            260                 265                 270

Val Ala Gly His Glu Thr Thr Ser Gly Leu Leu Ser Phe Ala Val Tyr
        275                 280                 285

Tyr Leu Leu Thr Thr Pro Asp Ala Met Ala Lys Ala Ala His Glu Val
    290                 295                 300

Asp Asp Val Val Gly Asp Gln Glu Leu Thr Ile Glu His Leu Ser Met
305                 310                 315                 320

Leu Lys Tyr Leu Asn Ala Ile Leu Arg Glu Thr Leu Arg Leu Met Pro
                325                 330                 335

Thr Ala Pro Gly Phe Ser Val Thr Pro Tyr Lys Pro Glu Ile Ile Gly
            340                 345                 350

Gly Lys Tyr Glu Val Lys Pro Gly Asp Ser Leu Asp Val Phe Leu Ala
        355                 360                 365

Ala Val His Arg Asp Pro Ala Val Tyr Gly Ser Asp Ala Asp Glu Phe
    370                 375                 380

Arg Pro Glu Arg Met Phe Asp Glu His Phe Gln Lys Leu Pro Ala Asn
385                 390                 395                 400

Ser Trp Lys Pro Phe Gly Asn Gly Lys Arg Ser Cys Ile Gly Arg Ala
                405                 410                 415

Phe Ala Trp Gln Glu Ala Leu Met Ile Leu Ala Leu Ile Leu Gln Ser
            420                 425                 430

Phe Ser Leu Asp Leu Val Asp Arg Gly Tyr Thr Leu Lys Leu Lys Glu
        435                 440                 445

Ser Leu Thr Ile Lys Pro Asp Asn Leu Trp Ala Tyr Ala Thr Pro Arg
    450                 455                 460

Pro Gly Arg Asn Val Leu His Ala Arg Leu Ala Leu Gln Thr Asn Ser
465                 470                 475                 480

Thr His Pro Glu Gly Leu Met Ser Leu Lys His Glu Thr Val Glu Ser
                485                 490                 495

Gln Pro Ala Thr Ile Leu Tyr Gly Ser Asn Thr Gly Thr Cys Glu Ala
            500                 505                 510

Leu Ala His Arg Leu Ala Ile Glu Met Ser Ser Lys Gly Arg Phe Val
        515                 520                 525

Cys Lys Val Gln Pro Met Asp Glu Ile Glu His Arg Arg Leu Pro Arg
    530                 535                 540

Gly Gln Pro Val Ile Ile Val Thr Gly Ser Tyr Asp Gly Arg Pro Pro
545                 550                 555                 560

Glu Asn Ala Arg His Phe Val Lys Trp Leu Gln Ser Leu Glu Gly Asn
                565                 570                 575

Asp Leu Glu Gly Ile Gln Tyr Ala Val Phe Gly Cys Gly Leu Pro Gly
            580                 585                 590

His His Asp Trp Ser Thr Thr Phe Tyr Lys Ile Pro Thr Leu Ile Asp
        595                 600                 605
```

```
Thr Ile Met Ala Glu His Gly Gly Ala Arg Leu Ala Pro Arg Gly Ser
    610             615                 620

Ala Asp Thr Ala Glu Asp Pro Phe Val Glu Leu Glu Ser Trp Ser
625             630                 635                 640

Glu Arg Arg Val Trp Pro Gly Leu Glu Ala Ala Phe Asp Leu Val Arg
                645                 650                 655

His Asn Ser Ser Asp Gly Thr Gly Lys Ser Thr Arg Ile Thr Ile Arg
            660                 665                 670

Ser Pro Tyr Thr Leu Arg Ala Ala His Glu Thr Ala Val Val His Gln
        675                 680                 685

Val Arg Val Leu Thr Ser Ala Glu Thr Thr Lys Lys Val His Val Glu
690                 695                 700

Leu Ala Leu Pro Asp Thr Ile Asn Tyr Arg Pro Gly Asp His Leu Ala
705             710                 715                 720

Ile Leu Pro Leu Asn Ser Arg Gln Ser Val Gln Arg Val Leu Ser Leu
                725                 730                 735

Phe Gln Ile Gly Ser Asp Thr Ile Leu Tyr Ile Thr Ser Ser Ser Ala
            740                 745                 750

Thr Ser Leu Pro Thr Asp Thr Pro Ile Ser Ala His Asp Leu Leu Ser
        755                 760                 765

Gly Tyr Val Glu Leu Asn Gln Val Ala Thr Pro Thr Ser Leu Arg Ser
770                 775                 780

Leu Ala Ala Lys Ala Thr Asp Glu Lys Thr Ala Glu Tyr Leu Glu Ala
785             790                 795                 800

Leu Ala Thr Asp Arg Tyr Thr Thr Glu Val Arg Gly Asn His Leu Ser
                805                 810                 815

Leu Leu Asp Ile Leu Glu Ser Tyr Ser Val Pro Ser Ile Glu Ile Gln
            820                 825                 830

His Tyr Ile Gln Met Leu Pro Pro Leu Arg Pro Arg Gln Tyr Thr Ile
        835                 840                 845

Ser Ser Ser Pro Arg Leu Asn Arg Gly Gln Ala Ser Leu Thr Val Ser
850                 855                 860

Val Met Glu Arg Ala Asp Ile Gly Gly Pro Arg Asn Cys Ala Gly Val
865                 870                 875                 880

Ala Ser Asn Tyr Leu Ala Ser Cys Thr Pro Gly Ser Ile Leu Arg Val
            885                 890                 895

Ser Leu Arg His Ala Asn Pro Asp Phe Arg Leu Pro Asp Glu Ser Cys
        900                 905                 910

Ser His Pro Ile Ile Met Val Ala Ala Gly Ser Gly Ile Ala Pro Phe
        915                 920                 925

Arg Ala Phe Val Gln Glu Arg Ser Val Arg Gln Lys Glu Gly Ile Ile
930                 935                 940

Leu Pro Pro Ala Phe Leu Phe Phe Gly Cys Arg Arg Ala Asp Leu Asp
945             950                 955                 960

Asp Leu Tyr Arg Glu Glu Leu Asp Ala Phe Glu Gln Gly Val Val
                965                 970                 975

Thr Leu Phe Arg Ala Phe Ser Arg Ala Gln Ser Glu Ser His Gly Cys
            980                 985                 990

Lys Tyr Val Gln Asp Leu Leu Trp Met Glu Arg Val Arg Val Lys Thr
        995                 1000                1005

Leu Trp Gly Gln Asp Ala Lys Val Phe Val Cys Gly Ser Val Arg
    1010                1015                1020

Met Asn Glu Gly Val Lys Ala Ile Ile Ser Lys Ile Val Ser Pro
```

```
                1025                1030                1035
Thr Pro Thr Glu Glu Leu Ala Arg Arg Tyr Ile Ala Glu Thr Phe
    1040                1045                1050
Ile
```

<210> SEQ ID NO 10
<211> LENGTH: 1076
<212> TYPE: PRT
<213> ORGANISM: Hypocrea virens

<400> SEQUENCE: 10

```
Met Lys Pro Ala Lys Asn Pro Asn Leu Val Glu Ile Pro Lys Pro Lys
1               5                   10                  15

Gly Leu Pro Val Ile Gly Ser Leu His His Ile Asp Leu Glu Ser Pro
                20                  25                  30

Leu Phe Ser Leu Ile Glu Leu Ile Gln Pro Leu Gly Pro Ile Cys Gln
            35                  40                  45

Leu Thr Phe Gly Ser Glu Leu Asn Ile Phe Val Ser Ser Ile Glu Leu
        50                  55                  60

Leu Asn Glu Leu Cys Asp Glu Ser Arg Phe Gln Lys Ile Val Thr Ala
65                  70                  75                  80

Glu Leu Glu Lys Leu Arg His Val Val His Asp Gly Leu Phe Thr Ala
                85                  90                  95

Arg Asn Glu Glu Arg Asn Trp Glu Ile Ala His Arg Ile Leu Met Pro
            100                 105                 110

Val Phe Gly Thr Ile Lys Ile Arg Glu Met Phe Pro Glu Met Lys Asp
        115                 120                 125

Leu Ala Gln Gln Leu Cys Leu Lys Trp Ala Arg Tyr Gly Glu Glu Tyr
    130                 135                 140

Val Ile Asp Val Thr Ala Asp Phe Thr Arg Leu Thr Leu Asp Thr Leu
145                 150                 155                 160

Ala Leu Cys Thr Met Gly Phe Arg Phe Asn Ser Phe His Asn Gly Thr
                165                 170                 175

Val Leu His Pro Phe Val Asp Ser Met Val Arg Thr Leu Lys Glu Ala
            180                 185                 190

Ser Val Gln Ala Ala Leu Pro Asn Phe Ile Asn Ser Leu Arg Lys Lys
        195                 200                 205

Ser Trp Arg Arg Tyr Glu Lys Asp Thr Ala Phe Met Arg Lys Leu Cys
    210                 215                 220

Gln Asp Ile Ile Asp Lys Arg Lys Ser Gln Thr Asp Thr Asp Ser His
225                 230                 235                 240

Asp Leu Leu Ala Ala Leu Leu Arg Gly Arg Asp Pro Lys Thr Gly Glu
                245                 250                 255

Gly Leu Ser Asp Asp Ser Ile Ile Asp Asn Met Leu Thr Phe Leu Ile
            260                 265                 270

Ala Gly His Glu Thr Thr Ser Gly Leu Leu Ser Phe Ala Met Tyr Tyr
        275                 280                 285

Leu Leu Ala Asn Pro Gln Thr Met Glu Lys Ala Arg Gln Glu Val Asp
    290                 295                 300

Glu Val Ser Gln Gly Ser Pro Ile Ala Val His Leu Ser Lys Leu
305                 310                 315                 320

Pro Tyr Leu Asn Ala Val Leu Lys Glu Thr Leu Arg Leu Gln Pro Thr
                325                 330                 335

Ala Pro Gly Phe Ile Leu Ser Ser Pro Lys Asp Glu Ile Ile Gly Gly
```

-continued

```
            340                 345                 350
Lys Tyr Leu Ile Pro Ala Asn Ile Pro Ile Gly Val Leu Leu His Met
            355                 360                 365

Val His Leu Asp Lys Ala Val Tyr Gly Glu Asp Ala Ala Glu Phe Lys
            370                 375                 380

Pro Glu Arg Met Leu Asp Glu Asn Phe Asn Lys Leu Pro Pro Asn Ser
385                 390                 395                 400

Trp Lys Pro Phe Gly Asn Gly Met Arg Gly Cys Ile Gly Arg Ala Phe
                    405                 410                 415

Ala Thr Gln Glu Ala Leu Leu Ile Val Ala Met Leu Leu Gln Ser Phe
                    420                 425                 430

Thr Phe Glu Met Ala Asp Pro Gly Tyr Lys Leu Lys Ile Lys Glu Thr
            435                 440                 445

Leu Thr Val Lys Pro Asp Asn Phe Arg Met Lys Ala Lys Leu Arg Arg
        450                 455                 460

Gly Gly Thr Ala Thr Asp Phe Gln Arg Glu Leu Gln Ser Leu Gly Ser
465                 470                 475                 480

Val Gly Ala Lys Leu Ser Ser Thr Pro Ser Val Thr Ser Ala Gln Thr
                    485                 490                 495

Gly Gly Gly Asp Lys Lys Pro Leu Thr Ile Leu Tyr Gly Ser Asn Ser
                    500                 505                 510

Gly Thr Cys Glu Ala Leu Ala Tyr Arg Leu Ala Ser Asp Ala Thr Leu
            515                 520                 525

His Gly Phe Tyr Ala Arg Lys Ile Ala Pro Leu Asn Ala Ala Arg Asn
            530                 535                 540

Ser Leu Pro Lys Ser Glu Pro Val Ile Ile Leu Ala Ala Ser Tyr Asp
545                 550                 555                 560

Gly Leu Pro Ser Asp Asn Ala Glu Glu Phe Phe Asp Trp Leu Asn Thr
                    565                 570                 575

Ala Glu Lys Asp Ser Leu Lys Gly Val Ser Tyr Ser Val Phe Gly Cys
                    580                 585                 590

Gly His Arg Asp Trp Val Ala Thr Phe Gln Arg Val Pro Ile Leu Ile
            595                 600                 605

Asp Asp Leu Leu Gln Arg Ala Gly Ala Glu Arg Phe Ala Asn Arg Gly
        610                 615                 620

Leu Ala Asp Ser Ala Val Met Asp Leu Phe Val Glu Leu Glu Lys Trp
625                 630                 635                 640

Thr Thr Asp Ser Val Trp Pro Ala Ile Ser Gln Thr Asp Gly Lys Gln
                    645                 650                 655

Asp Asn Asp Gly Glu Gly Lys Leu Ile Ser Ser Leu Leu Lys Val Glu
                    660                 665                 670

Phe Ser Gln Pro Arg Gln Leu Gln Gln Tyr Ser His Leu Val Glu Ala
            675                 680                 685

Thr Val Met Glu Ser Arg Ser Leu Thr Thr Pro Ser Ala Ile Gly Lys
            690                 695                 700

Lys Met His Val Asp Ile Gln Leu Pro Ser Gly Val Ser Tyr His Pro
705                 710                 715                 720

Gly Asp His Leu Leu Val Leu Pro Val Asn Pro Ile Arg Asn Val Lys
                    725                 730                 735

Arg Val Leu Ser Arg Phe His Leu Thr Trp Asp Thr Ile Val Arg Ala
                    740                 745                 750

Ser Gly Asn Glu Ser Val Arg Ile Pro Ile Glu Thr Ala Met Thr Val
            755                 760                 765
```

```
His Glu Leu Leu Ser Ser Tyr Phe Glu Leu Ala Gln Pro Ala Thr Pro
    770                 775                 780

Arg Asp Ile Arg Val Leu Ala Ala Ala Glu Asp Glu Ala Thr Lys
785                 790                 795                 800

Gln Val Leu Asn Asn Leu Ala Thr Thr Ser Tyr Leu Glu Asp Ile Gln
                805                 810                 815

Glu Lys Lys Thr Ser Leu Leu Asp Leu Leu Glu Lys Phe Pro Glu Ile
            820                 825                 830

Ser Ile Ala Phe Gly Thr Tyr Leu Thr Leu Leu Pro Ser Leu Arg Leu
        835                 840                 845

Arg Thr Tyr Ser Ile Ser Ser Pro Ser Trp Asn Ser Ser Arg Ala
    850                 855                 860

Thr Leu Thr Leu Ser Val Leu Asp Glu Pro Ala Thr Thr Pro Gly Ser
865                 870                 875                 880

Lys Arg Tyr Leu Gly Val Ala Ser Asn His Leu Ala Gly Leu Thr Pro
                885                 890                 895

Gly Asp Leu Ile His Val Ala Thr Arg Pro Val Lys Gly Ile Phe Gln
            900                 905                 910

Met Pro Ala Asp Leu Ser Lys Ala Pro Thr Ile Met Ile Ala Ala Gly
        915                 920                 925

Ala Gly Leu Ala Pro Phe Arg Gly Phe Ile Gln Glu Arg Ala Tyr Gln
    930                 935                 940

Gln Gln Asn Gly Val Gln Leu Ala Pro Ala Ala Leu Phe Phe Gly Cys
945                 950                 955                 960

Arg Ser Ser His Asp Asp Leu Tyr Arg Ser Leu Glu Asp Ala Phe Glu
                965                 970                 975

Ser Ser Gly Val Ile Arg Val Phe Arg Ala Tyr Ser Arg Glu Asp Val
            980                 985                 990

Gly Ser Lys Ser Asn Thr Arg Lys Gly Tyr Val Gln Asp Ser Leu Gln
        995                 1000                1005

Ala Glu Lys Asp Val Phe Val Gln Leu Trp Asn Ala Gly Ala Lys
    1010                1015                1020

Val Tyr Val Cys Gly Ser Val Lys Met Ala Ser Gln Val Lys Asp
    1025                1030                1035

Leu Val Ala Asn Leu Val Tyr Thr Ala Glu Pro Met Asp Ala Gln
    1040                1045                1050

Lys Glu Phe Thr Pro Gln Glu Trp Phe Lys Arg Phe Glu Lys Thr
    1055                1060                1065

Arg Tyr Ala Ala Glu Ile Phe Thr
    1070                1075

<210> SEQ ID NO 11
<211> LENGTH: 1073
<212> TYPE: PRT
<213> ORGANISM: Oidiodendron maius

<400> SEQUENCE: 11

Met Thr Lys Lys Asn His Ala Leu Ile Pro Ile Pro Gly Pro Ser Val
1               5                   10                  15

Trp Pro Leu Leu Gly Asn Leu Phe Asp Ile Asp Thr Glu His Gly Leu
                20                  25                  30

Ala Ser Val Leu Glu Met Gly Arg Ser Tyr Gly Asp Ile Phe Gln Leu
            35                  40                  45

Val Leu Gly Gly Asn Lys Leu Val Phe Leu Gln Thr His Ala Leu Phe
```

-continued

```
                50                  55                  60
Asp Glu Val Cys Asp Glu Ser Arg Phe Cys Lys Val Val Ser Gly
 65                  70                  75                  80

Leu Gly Asn Leu Arg Ala Gly Val Asn Asp Gly Leu Phe Thr Ala His
                     85                  90                  95

Asp Gly Glu His Asn Trp Gly Val Ala His Arg Ile Ile Met Pro Ile
                100                 105                 110

Phe Gly Pro Ile Lys Ile Arg Glu Thr Leu Gly Gly Met Lys Asp Val
            115                 120                 125

Cys Gln Glu Leu Ser Leu Lys Trp Ala Arg Tyr Gly Pro Asp His Arg
        130                 135                 140

Ile Asp Ile Ala Gly Asp Leu Thr Arg Leu Thr Leu Asp Thr Ile Ala
145                 150                 155                 160

Phe Cys Thr Met Gly Tyr Arg Phe Asn Ser Phe Tyr Arg Asn Ser Asp
                165                 170                 175

Val His Pro Phe Val Lys Ser Met Val Gly Phe Leu Arg Glu Ala Asp
            180                 185                 190

Lys Ser Ser Met Ile Pro Glu Tyr Leu Asn Ala Phe Arg Trp Lys Ala
        195                 200                 205

Arg Arg Ser Phe Leu Gly Asp Ile Ala Ser Met Arg Glu Met Ser Met
210                 215                 220

Met Ile Leu Asn Leu Arg Arg Gly Asn Pro Ser Asp Arg Asp Asp Leu
225                 230                 235                 240

Leu Asn Ala Leu Leu His Gly Arg Asp Pro Lys Thr Gly Glu Gly Met
                245                 250                 255

Ser Asp Glu Ser Ile Ile Asn Asn Leu Ile Thr Phe Leu Val Ala Gly
            260                 265                 270

His Glu Thr Thr Ser Gly Ala Leu Ser Phe Val Phe Tyr Tyr Leu Leu
        275                 280                 285

Thr Asn Pro Glu Ser Leu Lys Asn Ala Arg Glu Glu Val Asp Arg Val
290                 295                 300

Ile Gly Ala Gly Asn Ile Thr Ala Asp His Leu Ser Lys Leu Pro Tyr
305                 310                 315                 320

Ile Asp Ala Val Leu Arg Glu Ala Leu Arg Leu Asn Pro Thr Gly Pro
                325                 330                 335

Ala Ile Thr Leu Gly Ala Arg Glu Asp Thr Thr Leu Gly Gly Lys Tyr
            340                 345                 350

Ala Val Lys Lys Gly Glu Pro Val Leu Cys Met Phe His Asn Ile His
        355                 360                 365

Arg Asp Lys Lys Val Tyr Gly Glu Asp Ala Asp Glu Trp Lys Pro Glu
370                 375                 380

Arg Met Met Asp Glu Asn Phe Asn Lys Leu Pro Lys Asn Ala Trp Lys
385                 390                 395                 400

Pro Phe Gly Asn Gly Thr Arg Gly Cys Ile Gly Arg Ala Phe Ala Trp
                405                 410                 415

Gln Glu Ser Gln Leu Val Ile Ala Ser Ile Leu Gln Asn Phe Asp Leu
            420                 425                 430

Thr Leu Asp Asn Pro Asp Tyr Lys Leu Glu Ile Val Glu Thr Leu Thr
        435                 440                 445

Ile Lys Pro Gly Asn Phe Tyr Val Arg Ala Lys Leu Arg Ser Gly Arg
450                 455                 460

Thr Pro Arg Glu Leu Cys Gly Phe Ser Asn Pro Ile Ser Thr Asn Ile
465                 470                 475                 480
```

```
Gln Ile Lys Asn Gly Thr Ile Ala Pro Ala Asn Asp Gly Gln Val Gly
                485                 490                 495

Asn Ser Thr Pro Val Thr Ile Leu Tyr Gly Ser Asn Ser Gly Thr Cys
            500                 505                 510

Glu Ala Leu Ala His Arg Leu Ala Arg Asp Ala Pro Ser Tyr Gly Tyr
        515                 520                 525

Ser Val Thr Thr Val Ala Thr Leu Asp Ser Val Ile Gly Ile Leu Pro
    530                 535                 540

Arg Ala Lys Asp Glu Leu Val Val Ile Ile Thr Cys Ser Tyr Asp Gly
545                 550                 555                 560

Leu Pro Ala Asp Asn Ala Val Arg Phe Cys Asn Trp Leu Lys Thr Leu
                565                 570                 575

Asp Glu Asp Ala Leu Gly Gly Met Pro Phe Ala Val Phe Ala Cys Gly
            580                 585                 590

His His Asp Trp Ala Lys Thr Phe Tyr Lys Val Pro Ile Met Ile Asp
        595                 600                 605

Glu Leu Leu Ala Arg Ala Gly Ala His Arg Val Ala Gln Met Gly Lys
    610                 615                 620

Ala Asn Ser Ala Val Ser Asp Met Phe Ser Asp Leu Glu Asn Trp Glu
625                 630                 635                 640

Asp Glu His Leu Trp Ser Ser Ser Ala Ala Gly Asn Glu Thr Val
                645                 650                 655

Asp Asn Val Ala Arg Thr Glu Val Lys Gln Asp Ile Thr Ile Thr Asn
            660                 665                 670

Pro Arg Ala Arg Ala Leu His His Asn Ala Val Glu Cys Ile Val Ser
        675                 680                 685

Glu Thr His Lys Leu Ser Glu Ser Gly Ser Ala Leu Lys Tyr His Val
    690                 695                 700

Glu Ile Gln Leu Pro Ala Asn Met Lys Tyr Ala Pro Gly Asp His Leu
705                 710                 715                 720

Ser Val Leu Pro Ile Asn Pro Arg Gln Asn Val Arg Arg Ala Leu Ala
                725                 730                 735

Arg Phe His Leu Ala Gly Asp Ser Val Leu Ser Val Ala Arg Ile Gly
            740                 745                 750

His Met Gly Thr Leu Gly Gln Glu Thr Leu Ser Ala Phe Asp Val Phe
        755                 760                 765

Ala Ser Tyr Val Glu Leu Ser Gln Pro Ala Thr Arg Arg Asn Ile Ala
    770                 775                 780

Thr Leu Leu Ser Val Thr Pro Glu Gly Glu Gly Arg Tyr Glu Leu Ala
785                 790                 795                 800

Glu Leu Gly Gly Ala Ala Phe Glu Ser Gln Ile Arg Asp Met Arg Val
                805                 810                 815

Ser Val Leu Asp Leu Leu Glu Arg Tyr Lys Ala Ile Lys Leu Cys Val
            820                 825                 830

Gly Ala Phe Ile Asp Met Leu Pro Pro Leu Arg Val Arg Thr Tyr Ser
        835                 840                 845

Ile Ser Ser Ser Ala Leu Trp Lys Pro Ser His Ala Ser Leu Thr Ile
    850                 855                 860

Ser Val Leu Ala Gln Pro Ala Leu Ser Gly Gln Gly Ser Phe Leu Gly
865                 870                 875                 880

Val Ala Ser Asn Phe Leu Ala Asp Leu Val Pro Gly Asp Ala Val His
                885                 890                 895
```

```
Phe Thr Ile Arg Pro Cys Lys Lys Gln Phe His Leu Pro Asp Asp Ala
            900                 905                 910

Ser Ala His Pro Ile Ile Met Val Ala Ala Gly Ser Gly Ile Ala Pro
        915                 920                 925

Phe Arg Gly Phe Ile Gln Asp Arg Ala Leu Gln Arg Arg Asn Gly Val
    930                 935                 940

Gln Leu Gln Pro Ala Ile Leu Phe Phe Gly Cys Arg Gly Ser Lys Gln
945                 950                 955                 960

Asp Asp Leu Tyr Arg Gln Glu Leu Asp Glu Phe Glu Ala Glu Gly Val
                965                 970                 975

Val Ser Val Arg Arg Ala Phe Ser Gly Glu Glu Thr Val Ser Ile Ser
            980                 985                 990

Glu Ser Arg Met Tyr Val Gln Asp Arg Met Trp Ala Asp Arg Ala Glu
        995                1000                1005

Val Ile Gln Leu Trp Asn Leu Gly Ala Lys Ile Tyr Val Cys Gly
    1010                1015                1020

Gly Ile Asn Met Ala Asp Gly Val Arg Glu Ile Phe Asn Glu Ile
    1025                1030                1035

Val Gly Pro Thr Glu Val Asp Gly Lys Arg Gly Ala Glu Ser Leu
    1040                1045                1050

Asn Lys Leu Ser Glu Glu Thr Met Ser Ala Arg Tyr Val Ala Glu
    1055                1060                1065

Ile Phe Ser Gln Thr
    1070

<210> SEQ ID NO 12
<211> LENGTH: 1068
<212> TYPE: PRT
<213> ORGANISM: Setosphaeria turcica

<400> SEQUENCE: 12

Met Ser Ala Pro Asn Arg Gln Leu Val Pro Ile Pro Gly Pro Ser Ala
1               5                   10                  15

Leu Pro Ile Val Gly Asn Thr Phe Asp Leu Asp Leu Asp Ala Ser Ile
            20                  25                  30

Gln Ser Leu Val Asn Met Phe Glu Glu Tyr Gly Pro Val Phe Gln Leu
        35                  40                  45

Thr Ile Ala Gly His Lys Gln Ile Phe Val Gly Asn Val Gln Leu Thr
    50                  55                  60

Asn Glu Val Cys Asp Glu Ser Arg Phe Cys Lys Ile Val Phe Ser Gly
65                  70                  75                  80

Leu Glu Leu Leu Arg Ser Ala Val His Asp Gly Leu Phe Thr Ala His
                85                  90                  95

Glu Gly Glu Arg Asn Trp Asp Ile Ala His Arg Ile Leu Met Pro Val
            100                 105                 110

Phe Gly Pro Thr Lys Ile Arg Gly Met Phe Asp Gln Met Asn Asp Ile
        115                 120                 125

Ala Gln Gln Leu Cys Leu Lys Trp Gly Arg Tyr Gly Pro Thr Phe Pro
    130                 135                 140

Ile Glu Val Thr Glu Asp Phe Arg Leu Thr Leu Asp Thr Ile Ala
145                 150                 155                 160

Leu Cys Ala Met Gly Tyr Arg Phe Asn Ser Phe Tyr Arg Asp Asn Met
                165                 170                 175

His Pro Phe Val Asp Arg Met Asn Arg Phe Leu Lys Asp Thr Asn Thr
            180                 185                 190
```

```
Gln Ser Gly Leu Pro Asp Leu Phe Asn Ser Leu Trp Leu His Ala Lys
        195                 200                 205

Lys Arg Asn Lys Glu Asp Ile Lys Ala Met Arg Glu Phe Ser Gln Glu
    210                 215                 220

Val Val Asp Gln Arg Arg Gln Asn Pro Val Asp Ala Asp Asp Leu Leu
225                 230                 235                 240

Asn Ala Leu Leu His Gln Thr Asp Pro Lys Thr Gly Glu Gly Leu Ser
                245                 250                 255

Asp Ser Ser Ile Ile Asp Asn Met Ile Thr Phe Leu Val Ala Gly His
                260                 265                 270

Glu Thr Thr Ser Gly Leu Leu Ser Phe Ala Phe Tyr Tyr Met Leu Lys
        275                 280                 285

Asn Pro Trp Ala Met Glu Lys Ala Gln Gln Glu Val Asp Asn Val Ile
    290                 295                 300

Gly Thr Glu Arg Val Thr Val Asn His Leu Ser Lys Leu Glu Tyr Leu
305                 310                 315                 320

Asn Ala Ile Leu Arg Glu Thr Leu Arg Leu Met Pro Thr Ala Pro Ala
                325                 330                 335

Phe Thr Val Gly Ala Leu Lys Asp Asp Val Ile Gly Gly Lys Tyr Ala
                340                 345                 350

Val Lys Lys Gly Glu Pro Ile Asn Pro Ile Leu Gln Ala Val His Cys
        355                 360                 365

Asp Lys Glu Val Tyr Gly Pro Asp Ala Thr Glu Trp Lys Pro Glu Arg
    370                 375                 380

Met Leu Glu Glu Gly Phe His Lys Leu Pro Ala Asn Ser Trp Lys Pro
385                 390                 395                 400

Phe Gly Asn Gly Lys Arg Gly Cys Ile Gly Arg Ala Phe Ala Trp Gln
                405                 410                 415

Glu Ala Leu Leu Val Val Ala Val Leu Leu Gln Ser Phe Thr Phe Thr
        420                 425                 430

Glu Asp Asp Pro Ser Tyr Gln Leu Arg Ile Arg Glu Ala Leu Thr Ile
    435                 440                 445

Lys Pro Asp Gly Phe Lys Ile Arg Ala Thr Leu Arg Glu His Lys Thr
    450                 455                 460

Thr Ala Gly Met Val Pro Glu Ser Val Gln Ser Leu Arg Gln Ala Gln
465                 470                 475                 480

Lys Ser Gly Lys Pro Gly Asn Ser Lys Ser Ser Ala Asn Glu Ser Met
                485                 490                 495

Val Gly Gln Gly Asn Gly Arg Ser Val Ser Ile Phe Tyr Gly Ser Asn
                500                 505                 510

Ser Gly Ser Cys Glu Ser Leu Ala Asn Leu Leu Ala Ser Asp Cys Ala
        515                 520                 525

Lys Tyr Gly Phe Ser Val Gln Thr Thr Asp Ala Leu Asp Ala Ala Arg
    530                 535                 540

Glu Asn Phe Thr Ser Asn Gln Ile Val Leu Ile Val Ala Ser Thr Tyr
545                 550                 555                 560

Asp Gly Lys Pro Ala Asp Asn Ala Thr Glu Phe Val Asn Trp Leu Lys
                565                 570                 575

Ser Leu Thr Gly Glu Pro Leu Lys Gly Val Ser Tyr Ala Val Phe Gly
                580                 585                 590

Cys Gly His His Asp Trp Ala Thr Thr Phe Tyr Lys Ile Pro Ile Leu
        595                 600                 605
```

```
Ile Asp Glu Leu Leu Glu Gln Arg Gly Ala Gln Arg Val Ala Pro Arg
610                 615                 620

Gly Ala Ala Asn Ala Ala Val Ser Asp Leu Phe Ser Asp Leu Glu Lys
625                 630                 635                 640

Trp Glu Glu Ser Ile Leu Trp Pro Ala Leu Gly Leu Thr Pro Ala Leu
            645                 650                 655

Leu Glu Ser Gln Gly Asp Thr Gln Pro Arg Leu Thr Ile Ser Phe Gln
            660                 665                 670

Arg Pro Tyr Thr Gln Arg Lys Glu Phe Leu Glu Ala Thr Val Thr Ser
        675                 680                 685

Ala Ser Glu Leu Thr Thr Ser Ala Ser Pro Ser Arg Lys Cys His Met
690                 695                 700

Glu Leu Gln Leu Pro Gln Asp Met Thr Tyr Asn Thr Gly Asp Tyr Leu
705                 710                 715                 720

Ala Val Leu Pro Leu Asn Pro Leu Ser Asn Val Gln Arg Ala Leu Ser
                725                 730                 735

Arg Phe His Leu Ala Trp Asp Ser Val Leu Val Ile Glu Ala Thr Gly
            740                 745                 750

Pro Thr Gln Leu Pro Thr Ala Thr Pro Ile Ser Val Ala Asp Leu Phe
        755                 760                 765

Gly Ala Tyr Val Glu Leu Ser Gln Pro Ala Thr Pro Arg Asn Ile Arg
770                 775                 780

Ala Leu Ala Gly Ala Ala Ser Asp Glu Pro Thr Lys Gln Ala Leu Leu
785                 790                 795                 800

Lys Leu Ala Glu Asp Asp Phe Ala Thr Gln Val Arg Asp Lys Arg Leu
                805                 810                 815

Ser Val Leu Asp Leu Leu Gly Gln Tyr Glu Ser Val Ala Leu Pro Val
            820                 825                 830

Glu Ala Phe Ile Glu Met Leu Leu Pro Leu Arg Pro Arg Thr Tyr Ser
        835                 840                 845

Ile Ser Ser Ala Pro Gln Trp Asn Pro Ser His Ala Ser Ile Thr Trp
850                 855                 860

Ser Ile Ile Asp Thr Val Ser Trp Ser Gly His Gly Arg Phe Leu Gly
865                 870                 875                 880

Val Ala Ser Asn His Leu Tyr Asp Leu Ser Pro Gly Ala Val Val Arg
                885                 890                 895

Val Ser Val Arg Arg Ser Asn Pro Ala Phe His Pro Gln Asp Pro
            900                 905                 910

Asn Ser Tyr Pro Ile Ile Met Ile Ala Ser Gly Ser Gly Leu Ala Pro
        915                 920                 925

Phe Arg Gly Phe Ile Gln Glu Arg Ala Leu Gln Gln Lys Ala Gly Met
930                 935                 940

Thr Leu Ala Pro Ala Leu Leu Phe Phe Gly Cys Arg Gly Arg Asp Asp
945                 950                 955                 960

Asp Leu His Arg Ala Glu Met Asp Asp Phe Glu Lys Ser Gly Val Val
                965                 970                 975

Arg Val Met Arg Ala Tyr Ser Lys Ala Pro Asn Glu Pro Asp Ala Phe
            980                 985                 990

Gly Cys Ala Tyr Ile Gln Glu Arg  Val Trp Ser Glu Arg  Lys Glu Phe
        995                  1000                 1005

Arg Glu  Leu Trp Asn Arg Gly  Ala Thr Val Phe  Cys Gly Gly
        1010                 1015                 1020

Thr Lys Met Ser Glu Ala Ile  Lys Asp Val Phe Ile  Lys Ile Ala
```

Tyr Gly Asn Ala Gly Gln Asp Asp Asn Lys Ser Ser Arg Asp Trp
1040                     1045                    1050

Phe Ala Ser Leu Asp Pro His Arg Tyr Val Ala Glu Val Phe Asn
        1055                1060                1065

<210> SEQ ID NO 13
<211> LENGTH: 3153
<212> TYPE: DNA
<213> ORGANISM: Artificial Sequence
<220> FEATURE:
<223> OTHER INFORMATION: Codon-optimised sequence for expression in E.
      coli

<400> SEQUENCE: 13

| | | | | | |
|---|---|---|---|---|---|
| atgattaaag | aaacggaaca | atcccgggt | ccgcgtccgc | tgccggtggt | gggtaacctg | 60 |
| tttgacatgg | atctggaaca | cggtctggaa | tgcctgattc | gtctggccga | tgactttggc | 120 |
| ccgctgttcc | agattacgat | caatggtgaa | aaacagatct | tgcgacctc | tcaagccctg | 180 |
| gttgatgaac | tgtgtgacga | aagtcgtttc | cataaagcag | tcatgggcgg | tctggaaaaa | 240 |
| ctgcgcatgc | tggcgtctga | tggcctgttt | accgcctatc | atggtgaacg | cggctggggt | 300 |
| attgcacacc | gtatcctggt | gccggctttt | ggcccgctgc | gtattcgcaa | catgttcgaa | 360 |
| gaaatgaatg | atgttgcaca | gcaactgtgt | ttaaagtggg | ctcgccaggg | tagctctacg | 420 |
| agcattaaca | tcaccgatga | ctttacccgt | ctgacgctgg | ataccatcgc | gctgtgtacg | 480 |
| atgaactttc | gcctgaacag | cttctataac | aatgaaacca | tgcatccgtt | cgtcaaaagc | 540 |
| atgctgtacg | tgctgcgtga | atctgatatt | cagagtatgc | tgccgggcat | tgcgaattgc | 600 |
| atccgcgtga | agcccgttc | gcgcatgagc | aaacacatcc | aactgatgcg | taacatggcg | 660 |
| cgtggcatta | tccaggaacg | tcgcgatcaa | gccgaaccgg | tggatgacct | gctgaacacg | 720 |
| ctgctgaatg | tcgtgacccc | ggttaccggc | gagggtatga | gcgatgacct | gattatcaac | 780 |
| aatgtcatta | cgtttctgat | cgcaggccat | gaaaccacgt | ccggtctgct | gtcatttacc | 840 |
| ttctattacc | tgctgcagaa | tccgcacatt | ctggaacgtg | cgcaaaacga | agtggatgaa | 900 |
| gttacgggcg | gtgaacgcat | caccgtgcag | catctgggtc | gtctgacgta | tattgacgcc | 960 |
| atcctgaaag | aaagcctgcg | cctgatgccg | accgccccgg | catttaccgt | gacgccgaaa | 1020 |
| aaaccggaag | ttctgggcgg | tgcatgggct | attgatgcag | gccaggctgt | gaatgttctg | 1080 |
| ctgccggtct | gcctgcgtga | ccgcagcgtg | tttggtccgg | atgcggacga | atttcgtccg | 1140 |
| gaacgcatgc | tggaagaaaa | cttttcgaaa | ctgccgccga | atagctggaa | accgttcggc | 1200 |
| aacggtgaac | gttcttgtat | cggccgcgcg | tttgcctggc | aggaagcaca | actggtggtt | 1260 |
| gctatggttc | tgcagacctt | cgatctggtc | ccggatgacc | cgagttacaa | actgcgcatt | 1320 |
| aaagaaaccc | tgacgatcaa | accggatggt | ttccgtgtgc | gtgccaccct | gcgtcgcggc | 1380 |
| cagtctgcaa | ccggtctgag | tcaaggtagt | atgtccgcgt | caggtgccac | gagttccgtt | 1440 |
| gccagcccgg | gtccgccggc | cgcaaccggt | gcccagtcca | tccggccgg | cggtcaacgt | 1500 |
| atttcatttt | tctatggctc | gaacagcggc | acgtgcaaag | cactggctca | tcgcctggcg | 1560 |
| tcatcgctga | tgggccgtgg | ttttaccgaa | cagaaactgg | cagctctgga | tacggtcgtg | 1620 |
| ggcaatctgc | cgaccgacca | accggtcatt | atcgtgacca | cgagctacga | tggtcgcccg | 1680 |
| accgatgacg | cggaagaatt | tgtgcgctgg | ctggaatcga | acgtccggt | cctgcagggc | 1740 |
| gtgagctatg | cagttttggg | ctgtggtcat | cacgattggg | ctaaaacctt | ctaccgtatt | 1800 |

```
ccgatcctga ttgatgacct gatgcacaaa gccggtgcaa cccgtctgac cgcactgggt    1860
acggctaacg cggccgtttc ggacctgttt agcgacctgg aactgtggga agaaaccaat    1920
ctgctgccgg ccctgcgtga agccttcccg ccgagtaaca gctctgatgt ggaaagttcc    1980
gaaccgcatc agctgcaaat tgtgtttcc aaaccgcgtc gcgttgacat gcaccgcggc     2040
ctggttgaag caaaagttac cgctgtccgt accctgacgt ctccggatag tccggaaaaa    2100
cgccatgtcg aatttcatgt gcagggtgat accacctggc gtccgggtga ccatgttaac    2160
attctgccgg tcaatccgct gtccaccgtg tcacgcgttc tggcatattt tcagctggct    2220
ccggatcact ccatcacggt gaactcattc aatacccaag gtctgccgag cgccacgccg    2280
gttagcgcaa ccgaactgtt ttcatcgttc gttgaactgt cccagccggc aacgcgtaaa    2340
aacctgaaag cactggctat ggcagctgaa tcaaaaaccg atgaacaaga actgattcgc    2400
ctgcatgatt cctatgacgc gctggtgcgt gataaacgcg tctcagtgct ggacattctg    2460
gaacgctttc cgtctatcag tctgccgatc ggcatttttca ttagcatgct gccgccgctg    2520
cgtctgcgta cctactccct gtcaatggcg ccgtctttca aaccgtcgca tggtagcctg    2580
accttctctg tgattaatga accggcctgg agcggcaacg ccagtatct gggcgttggt     2640
tctaattacc tggcaagtct gaccccgggc tccctgctgt atctgtcacc gcgtccggca    2700
aaagatgctt tcacctgcc ggccgaccag ttcaacaccc cgattatcat gatttgcgca     2760
ggcagcggtc tggctccgtt tatgggtttc atccaggaac gcatgacctg gctgaaacaa    2820
ggccgtccgc tggcgaaagg tctgctgttt ttcggctgtc gcggtccgca tctggatgac    2880
ctgtattacg aagaactgtc tgaatttgaa gatgcgggcg ttgtcgaagt ccaccgtgcg    2940
tatagtcgcg ccccggatga cgtgcgtgcc aaaggttgcc gccatgtgca gcaccgtctg    3000
gttaccgaag ccgaagcggt gcgtgatcac tggggtcgta atgcaattgt ttacgtctgt    3060
ggcagctcta acatggctcg tggtgttcag accgtgctgg aagaaatcct gggtacgctg    3120
ccgccggaac gctatgtcgc tgaaatcttt taa                                 3153
```

<210> SEQ ID NO 14  
<211> LENGTH: 3153  
<212> TYPE: DNA  
<213> ORGANISM: Artificial Sequence  
<220> FEATURE:  
<223> OTHER INFORMATION: codon optimized for expression in P. pastoris

<400> SEQUENCE: 14

```
atgattaaag aaactgagca gattcctgga cctagaccac ttcctgtcgt cggtaacttg      60
ttcgatatgg atttggaaca tggtttggag tgtttgatta gattggctga tgatttcggt    120
ccattgttcc aaatcactat taatggtgaa aagcaaattt ttgctacttc tcaagctttg    180
gttgatgaat tgtgtgatga gtctagattc cacaaggctg ttatgggtgg tttggaaaaa    240
ttgagaatgt tggcttctga tggttttgttt actgcttacc atggagagag aggttggggt    300
attgctcaca gaattttggt tccagctttt ggtcctttga gaattagaaa catgttcgaa    360
gagatgaatg atgttgctca acaattgtgt ttgaagtggg ctagacaagg ttcttctact    420
tctattaaca tcactgatga tttcactaga ttgactttgg atactatcgc tttgtgtact    480
atgaacttca gattgaactc tttctacaac aacgaaacta tgcatccatt cgttaagtct    540
atgttgtacg ttttgagaga gtctgatatt caatctatgt tgcctggtat tgctaattgt    600
attagagtta aggctagatc cagaatgtct aagcacatcc aattgatgag aaacatggct    660
agaggtatta ttcaagaaag aagagatcaa gctgagccag ttgatgattt gttgaacact    720
```

```
ttgttgaatg gtagagatcc tgttactggt gaaggaatgt ctgatgattt gattattaac    780
aacgttatca ctttcttgat tgctggtcat gagactactt ctggtttgtt gtcttttact    840
ttctactatt tgttgcaaaa cccacacatt ttggaaagag ctcaaaacga agttgatgag    900
gttactggtg gtgagagaat tactgttcaa catttgggta gattgactta catcgatgct    960
atcttgaagg aatctttgag attgatgcca actgctcctg ctttcactgt tactccaaag   1020
aaacctgagg ttttgggtgg tgcttgggct attgatgctg gtcaagctgt taatgttttg   1080
ttgccagttt gtttgagaga tagatccgtt tttggtccag atgctgatga gtttagacct   1140
gagagaatgt tggaagagaa cttttctaag ttgccaccta attcttggaa acctttcggt   1200
aacggtgaaa gatcctgtat tggtagagct tttgcttggc aagaggctca attggttgtt   1260
gctatggttt tgcaaacttt cgatttggtt ccagatgatc cttcttacaa gttgagaatt   1320
aaagaaactt tgactattaa accagatggt tttagagtta gagctacttt gagaagaggt   1380
caatctgcta ctggtttgtc tcaaggttct atgtctgctt ctggtgctac ttcttctgtt   1440
gcttctccag gtccacctgc tgctactggt gctcaatcta atcctgctgg tggtcaaaga   1500 atctcttttct tttacggttc taactctggt acttgtaagg ctttggctca tagattggct   1560
tcttctttga tgggtagagg ttttactgaa caaaaattgg ctgctttgga tactgttgtt   1620
ggtaatttgc caactgatca acctgttatt atcgttacta cttcttatga tggtagacca   1680
actgatgatg ctgaagagtt cgttagatgg ttggagtcta agagacctgt tttgcaaggt   1740
gtttcttacg ctgttttggg ttgtggtcat cacgattggg ctaagacttt ctacagaatc   1800
ccaatcttga tcgatgattt gatgcacaaa gctggtgcta ctagattgac tgctttgggt   1860
actgctaacg ctgctgtttc tgatttgttt tctgatttgg aattgtggga agagactaat   1920
ttgttgcctg ctttgagaga ggctttccca ccttctaact cttctgatgt tgaatcttct   1980
gagccacatc aattgcaaat ttgtgtttct aagcctagaa gagttgatat gcacagaggt   2040
ttggttgaag ctaaagttac tgctgttaga actttgactt ctccagattc tcctgaaaag   2100
agacatgttg agttccacgt tcaaggagat actacttgga gaccaggaga tcatgttaac   2160
attttgccag ttaatccttt gtctactgtt tctagagttt tggcttactt tcaattggct   2220
cctgatcact ctatcactgt taactctttc aatactcaag gtttgccatc tgctactcct   2280
gtttctgcta ctgaattgtt ttcttctttc gttgagttgt ctcaaccagc tactagaaag   2340
aacttgaaag ctttggctat ggctgctgaa tctaagactg atgaacaaga gttgattaga   2400
ttgcatgatt cttacgatgc tttggttaga gataagagag tttctgtttt ggatatcttg   2460
gagagattcc catctatctc tttgcctatc ggtattttca tttctatgtt gccacctttg   2520
agattgagaa cttactcttt gtctatggct ccatctttta agccttctca tggttctttg   2580
actttctctg ttattaatga accagcttgg tctggtaacg tcaatactt gggtgttggt    2640 tctaattatt tggcttcttt gactcctggt tctttgttgt atttgtctcc aagacctgct   2700
aaagatgctt ttcacttgcc agctgatcaa ttcaacactc ctatcatcat gatctgtgct   2760
ggttctggtt tggctccatt catgggtttc attcaagaaa gaatgacttg gttgaagcaa   2820
ggtagaccat tggctaaagg tttgttgttt tcgttgtga gaggtcctca tttgatgat    2880 ttgtactatg aagagttgtc tgaatttgag gatgctggtg ttgttgaagt tcacagagct   2940
tactctagag ctcctgatga tgttagagct aaaggttgta gacatgttca acacagattg   3000
gttactgaag ctgaggctgt tagagatcat tgggtagaa atgctatcgt ttacgtttgt   3060
```

```
ggttcttcta acatggctag aggtgttcaa actgttttgg aggagattct tggaactttg    3120
ccacctgaga gatacgtcgc cgagattttc taa                                 3153

<210> SEQ ID NO 15
<211> LENGTH: 3192
<212> TYPE: DNA
<213> ORGANISM: Artificial Sequence
<220> FEATURE:
<223> OTHER INFORMATION: codon optimized for expression in E. coli

<400> SEQUENCE: 15
atgcgtgacg cggagcgtat cccgggtccg accccgctgc cggtggttgg taacctgttc     60
gacatcgatc tggaacacgt gctgcagagc gttattggtc tggcgaacaa gtacggcccg    120
ctgttccaaa tcaccattaa cggcgagaaa caaatctttg cgaccagcca ggcgctggtt    180
gacgagctgt gcgatgaaag ccgttttcac aaagcggtgg cgagcggcct ggagaacctg    240
cgtatgctgg cgcacgacgg tctgtttacc gcgtatcatg gtgaacgtgg ttggggtatt    300
gcgcaccgta ttctggttcc ggcgttcggt ccgctgcgta ccagagcat gtttgacgat    360 atgggcgatc tggcgcagca actgtgcctg aaatgggcgc gtcaaggtgc gagcaacagc    420
atcaacatta ccgacgattt cacccgtctg accctggaca ccattgcgct gtgcaccatg    480
gatttccgtc tgaacagctt ttacaacaac gacaccatgc acccgtttgt ggagagcatg    540
ctgtatgttc tgcgtgaagc ggatgtgcag agcgcgctgc cggtatcgc gaacagcgtt    600 cgtattatgg cgcaccgtcg tatgctgaag aacatcgagg cgatgcgtac cattgcgcgt    660
gacatcattc acgatcgtcg taagaaagaa acccggcgg acgatctgct gaacaccctg    720
ctgaacggtc gtgacccggt gaccggcgag ggcatgagcg acgaaagcat cattgataac    780
gtgatcacct tcctggttgc gggtcatgag accaccagcg tctgctgag cttcacctttt    840 tactatctgg ttcagcaccc ggacatcctg aagaaagcgc aaaaagaggt ggatgaaacc    900
gttggtcaag cgcagattag cgtgcagcac ctggcggagc tgccgtacat cgatgcgatt    960
ctgaaggaaa gcctgcgtat gatgccgacc cgcgccgggtt ttaccgttac cccgaagaaa   1020
gcggaaaccc tgggtggcaa atggctgctg aacgcgggtc agccgatcaa cgttctgctg   1080
ccggcgtgcc tgcgtgaccg tagcattttc ggtccgaacg cggatgagtt tagcccgggc   1140
cgtatgctgg cggaaaactt cagcaagctg ccgccgaaca ctggaaacc gtttggtaac   1200 ggcgagcgta gctgcatcgg tcgtgcgttc gcgtggcaag aagcgcagct ggttgtggcg   1260
atgattctgc agaactttga cctggttccg gacgatccga gctacaccct gcgtatcaag   1320
gagaccctga ccattaaacc ggatggtttc cgtgttcgtg cgaccctgcg tcaccgtcag   1380
accgcgaccg gtctgtttca acacaccctg agcgcgcgta acgacaccag cctggcgagc   1440
agcagcgcgc acttcatcaa gaaaagcgaa gatcaagcgc cggcgggtgg ccgtccgatt   1500
tgcttctttt acggtagcaa cagcggtacc tgcaaggcgc tggcgcaccg tctggcgagc   1560
gacctgatgc cgtatggttt caccgatcaa aaactggcgg tgctggacac cgcggttgat   1620
aacctgccgc gtgaccagcc ggttatcatt ctgaccacca cctacgatgg ccaaccgacc   1680
gacgatgcga gaaatttgt tgcgtggctg agagcggta aagtgccggc gctgcagggt   1740
atcagctacg cggtgttcgg ttgcggccac cacgactgga cccaaacctt ttatcgtatc   1800
ccgaccctga ttgatgagct gatgcacaaa gcgggtgcga cccgtctggc cgcgtggc   1860 accgcgaacg cggcggttag cgacctgttc agcgatctgg aagcgtggga ggaaaccagc   1920
ctgctgccgg cgctgcgtga gaccttcctg ctgagcagca gcagcgacct ggaaccgctg   1980
```

| | | | |
|---|---|---|---|
| aacctgcacc | aactgcagat | cagcctgagc aagccgcgtc | gtattgacct gcacaaagat | 2040 |
| ctgatggaag | cgcgtgtgac | caccgttcgt atcctgacca | acccggatac cccggagaag | 2100 |
| cgtcacattg | agttccgttt | tcagggtgac accaccctgc | gtccgggcga tcacgtgaac | 2160 |
| gttctgccgg | tgaacccgcc | gagcaccgtg ctgcgtgttc | tggcgcaatt caacctggcg | 2220 |
| ccggactaca | gcatcaccat | taacagcttt aacaccctgg | gtctgccgca ggcgaccccg | 2280 |
| gttagcgcga | gcgagctgtt | cagcgcgtat gtggaactga | ccaaccggc gacccgtaac | 2340 |
| aacctgcgta | tcctggcggc | gaccgcgcaa agcgatgagg | ataagcagga actgattcac | 2400 |
| ctgcaagaca | gctacgatag | cctggttcgt gacaaacgtg | tgagcgttct ggatctgctg | 2460 |
| gagcaatttc | cgagcgtgag | cctgccgatt gcggcgttta | ttagcatgct gccggcgctg | 2520 |
| cgtctgcgta | cctatagcct | gagcctggcg ccgagcttca | aaccgagcca cggtagcctg | 2580 |
| acctttagcg | tggttaacga | gccggcgcgt aacggcaacc | gtcgttacct gggtgttggc | 2640 |
| agcaactatc | tggcgagcct | gaccccgggt agcatcctgt | acctgagccc gcgtccggcg | 2700 |
| aaggaagcgt | tccacctgcc | ggtggaccag agccgtatcc | cgatcattat gatttgcgcg | 2760 |
| ggtagcggtc | tggcgccgtt | cctgagcttt atccaagacc | gtatgatttg cagcaacag | 2820 |
| gataaaccgc | tggcgcgtgc | gctgctgttc tttggttgcg | gtggccgttt cctggacgat | 2880 |
| ctgtatcacg | aggaactgag | cgagtttgaa gcggcgggtg | tggttgacgt tcgtcgtgcg | 2940 |
| tacagcaagg | tgctggacta | tgatatggcg cgtggctgca | aatacgtgca ggatcgtctg | 3000 |
| gttgcggagg | cgaacgcgat | ccgtcacctg tgggcgcaag | acgcgaccat ttatgtgtgc | 3060 |
| ggtagcgcgg | atatggcgaa | gggtgtggag ggcgttctgg | aaaaactgct gggcatgctg | 3120 |
| ccgcgtgagc | gttacgttac | cgaaatctat caaatgcaga | cccgtgacaa cgtgagcgaa | 3180 |
| tggctgattt | aa | | | 3192 |

<210> SEQ ID NO 16
<211> LENGTH: 3153
<212> TYPE: DNA
<213> ORGANISM: Artificial Sequence
<220> FEATURE:
<223> OTHER INFORMATION: codon optimized for expression in E. coli

<400> SEQUENCE: 16

| | | | |
|---|---|---|---|
| atgaaagacg | cggaacgtat | cccgggtccg aagccgctgc | cggtggttgg caacctgttc | 60 |
| gacatcgatc | cggagcacag | cctggaaagc attgttgcgt | ttgcggagaa attcggtccg | 120 |
| ctgtttcaga | tcaccattaa | cggcgaaaag cagatcttcg | cgaccagcca ggcgctggtt | 180 |
| gacgagctgt | gcgatgaact | gcgttttcac aaagcggtgg | ttaccggtct ggagattctg | 240 |
| cgtctgctgg | cgcacgacgg | tctgttcacc gcgtaccacg | gcgaacgtgg ttggggcatt | 300 |
| gcgcaccgta | tcctggttcc | ggcgtttggc ccgctgcgta | tccgtaacat gctggacgat | 360 |
| atgagcgatg | tggcgcagca | actgtgcctg aagtgggcgc | gtcagggtgg cagcaccagc | 420 |
| atcaacatta | ccgaggactt | cacccgtctg accctggata | ccattgcgct gtgcaccatg | 480 |
| ggtttccgtc | tgaacagctt | ttacaacaac gagaccatgc | acccgtttgt gcaaagcatg | 540 |
| ctgtatgttc | tgcgtgaagc | ggacatccag gcgaacctgc | cggtattgc gaacagcatc | 600 |
| cgtgttagcg | cgcaacgtcg | tatgcacaaa acattgaggc | gatgcgtac catggcgcgt | 660 |
| ggtatcattc | aggaacgtcg | taagaacaaa acccgtgg acgatatcct | gaacaccctg | 720 |
| ctgaacggcc | gtgacccggt | taccggcgag ggcatgagcg | acgatagcat cattgataac | 780 |

```
gtgattacct tcctgatcgc gggtcacgaa accaccagcg gcctgctgag cttcaccttt    840
tacttcctga tccaacaccc gcacattctg aagaaagcgc aggaagaggt ggacgagacc    900
gttggtctgg cgcagatcag cgcgcaacac ctggcggagc tgccgtatat tgatgcgatc    960
ctgaaggaaa gcctgcgtct gatgccgacc gcgccgggtt ttaccgtgac cccgaagaaa   1020
accgaagttc tgggtggccg ttggatgatc aacgcgggtc aaccggtgaa cgttctgctg   1080
ccggcgtgcc tgcgtgatca gagcgttttc ggcccggacg cggatgagtt tcgtccggaa   1140
cgtatgctgg cggagaactt cagcaaactg ccgccgaaca gctggaagcc gtttggtaac   1200
ggcgagcgtg gttgcattgg tcgtgcgttt cgtggcaggaagcgcaact ggtggttgcg   1260
```

<210> SEQ ID NO 17
<211> LENGTH: 3147
<212> TYPE: DNA
<213> ORGANISM: Artificial Sequence
<220> FEATURE:
<223> OTHER INFORMATION: codon optimized for expression in E. coli

<400> SEQUENCE: 17

```
atgaaggaca tggagagcat tccgggtccg aaaccgctgc cggtggttgg caacctgttc       60
gacattgatc tggagaacgg tctgcaaagc atcattaaga tggcgcacga gttcggtccg      120
ctgtttcaga ttaccatcaa cggccaaaaa cagatcttcg cgaccagcca agcgctggtt      180
gacgagctgt gcgatgaaac ccgttttcac aaggcggtga tgggtggcat tcagaagctg      240
cgtatgctgg cgaaagacgg tctgtttacc gcgtatcatg tgaacgtggt tggggtatt       300
gcgcaccgta ttctgatgcc ggcgtttggt ccgctgcgta tccgtgatat gtttgaagac      360
atgagcgatg ttgcgcagca actgtgcttc aaatgggcgc gtcagggtag cagcaccagc      420
attaacatct gcgacgattt tacccgtctg accctggaca ccatcgcgct gtgcaccatg      480
ggcttccgtc tgaacagcta ctataacagc aacgcgctgc accgtttat  gaaagcatg      540
ctgtacgttc tgaaagaggc ggaactgcag agcaccctgc cgggtgttgc gaactgcatg      600
cgtgtgaagg cgcaacgtcg tatgagcaaa cacatcgacg cgatgcgtag catggcgcgt      660
aacctgattg aggaacgtcg tgcgaaaccg gagccggtgg acgatctgct gaacaccctg      720
ctgaacggcc gtgatccgat caccggtgaa ggcatgagcg acgatctgat cattagcaac      780
atcattacct cctgattgc gggtcatgag accaccagcg gcctgctgag cttcaccttt       840
tactatctgc tgcaaaacca ggacgttctg aacgtgcgc  gtaacgaggt ggatgaagtt      900
accggtgtgg gcccgatcac cgtgcagcac ctggcgaagc tgccgtacat cgacgcgatt      960
atgaaagaga gcctgcgtct gatgccgacc gcgccggcgt tcaccgttac cccgcaaaag     1020
ccggaagtgc tgggtggcaa atggatgatt aacaccggtg atagcgttaa cctgctgctg     1080
ccggtgtgcc tgcgtgacga daccgttttc ggtccggatg cgggcgaatt tcgtccgaac     1140
cgtatgctgg aggaaaactt cagcaagctg ccgccgaaca gctggaaacc gtttggtaac     1200
ggcgagcgtg gttgcatcgg ccgtgcgttc gcgtggcaag aagcgcagct ggttgtggcg     1260
ctggtgctgc gtacctttga cctggcgcg  gaggatccgt actataagct gcgtatcaaa     1320
gaaaccctga ccattaagcc ggacggtttc cgtatccgtg cgaccctgcg tcatggtaaa     1380
agcgcgaccg cgctgagcca gaacaacatt agcgttggtg cggcggcgag cccggcgagc     1440
agcacctatc tggcgggtaa cgagaacggt cgtgatgcgg cgggtggcca accggtgagc     1500
ttcttttacg gtagcaacag cggtacctgc aaggcgctga cccaccgtct ggcgagcacc     1560
atgatgaccc gtggtttcac cgatcagaac atcgcgccgc tggacagcgc ggttgataac     1620
ctgccgcgtg accaaccgac catcattatc accaccacct atgatggcca gccgaccgac     1680
gatgcgaaga aatttgtggc gtggctggaa agcggtaaca gcccgagcct gcaaggcgtt     1740
agctacgcgg tgttcggttg cggccaccag gactggacca agaccttta  tcgtattccg     1800
atcctgattg atgcgctgat gtataagcg  ggtgcgaccc gtctggcgac ccgtggcgcg     1860
gcgaacgcgg cgatcagcga cctgttcagc gacctggaag tgtgggagga aaccaacctg     1920
ctgccgggtc tgcgtgagag cttcaacccg ccgaacaaca gcaactttgt gccgctggag     1980
ccgcaccaac tgcagatcag cattaacaag ccgacccgtg ttggtatgca ccgtgacctg     2040
```

```
atcgaagcga aagtgaccgc gattcgtacc ctgaccagcc cgggtgcgcc ggagaaacgt   2100
cacctggagt tctgcattcc gggcgagacc accctgcgtc cgggtgatca cctgaacatt   2160
ctgccggtta acccgccgag caccgtgagc cgtgcgctgg cgcgtttcaa cctggcgccg   2220
gaccacagca tcacctttga gagcagcaac gcgctggatc tgccgcaggc gaccccggtt   2280
agcgcggcgg agctgtttag cagctacctg gaactgagcc aaccggcgac ccgtaacaac   2340
ctgaaagaac tggcgagcac caccccgagc gatggcgaga acaggaact gctgcacctg     2400 tacgacagct atgatagcct gatccgtgcg aagcgtgcga gcgttctgga tctgctggag   2460
caattcacca gcgtgaccct gccgatcacc acctttatta gcatgctgcc ggcgctgcgt   2520
gtgcgtacct atagcctgag catggcgccg agcttcaaac cgctgcacta cagcctgacc   2580
tttagcgtta ttaacgaacc ggcgtggaac ggtaacggcc gttacctggg tgtggcgagc   2640
aactatctgg cgagcctgaa cctgggcagc atcctgtata ttagcccgcg tccggcgaag   2700
gatgcgttcc acctgccgac cgatcagagc agcaaaccga ttatcatgat ttgcgcgggt   2760
agcggtctgg cgccgttccg tagctttatt caagaccgta tgctgtggca gcaacaggat   2820
aagaccctgg cgaaagcgct gctgttcttt ggttgccgta gcccgcaact ggacgatctg   2880
taccacgacg agctgagcca gtttgaagcg gcgggtgtgg ttgaggttcg tcgtgcgtac   2940
agcaaggtgc cgaaccacta tctggcgaaa ggctgccgtt acgttcagca ccgtctgctg   3000
accgagaccg aaaccatcca agacatgtgg gcgcaggatg cgattatcta tgtgtgcggt   3060
agcggcaacc tggcgaaggg tgttaaagcg gtgctggaaa gcatgctggg caccctgagc   3120
gagcgttaca tcaccgaaat tttctaa                                        3147

<210> SEQ ID NO 18
<211> LENGTH: 3153
<212> TYPE: DNA
<213> ORGANISM: Artificial Sequence
<220> FEATURE:
<223> OTHER INFORMATION: Sequence of wild-type gene prepared for cloning
      in Pichia pastoris

<400> SEQUENCE: 18
atgaaagacg ccgagcgcat tcccggacct aaacccctgc cagttgtggg aaacctgttg     60
gacatcgacc ctgagcatgg tctgcaatcc attattgcat tcgcggataa atacggaccc    120
ctctttcaga tcactatcaa cggtgaaaag cagatcttcg cgactagcca ggccctggta    180
gatgagctct gcgacgaatc gcgcttccac aaggccgtag tgactggcct agaggtctta    240
cgattgctgg cccacgatgg cctcttcaca gcctaccacg gagagcgcgg ctgggggatc    300
gctcatcgga ttctggtgcc tgcctttggc cccctacgta tccggaacat gctcgacgat    360
atgagcgacg tagcgcaaca actgtgtttg aagtgggctc gccaaggagg ttcaaccagt    420
atcaatatca ccgaagactt cacacgcctc actttagaca ctattgccct ctgcacgatg    480
ggtttccggc tgaacagctt ctacaacaac gagaccatgc acccatttgt tcaatccatg    540
ctgtacgtcc tgaaggaagc cgatgtccag gctaatcttc ccgggattgc aaattcaatt    600
cgtgtctcgg cacagcggcg catgcataag aacatcgagg cgatgaggac tatggctcgc    660
ggcatcatcc aggagcgcag aaagaacaag atcccgttga tgacatcct gaacactctc     720 ttgaacggga gggacccagt cactggtgaa ggcatgagtg atgactcaat cattgacaat    780
gtcatcacat ttttgattgc tggccacgaa acaacttccg gtctgctctc gttcacgttc    840
tactttttga tccaacaccc ccacatcttg aagaaggccc aagaagaagt agacgagact    900
```

```
gtcggcctgg cccagatctc tgcgcagcac ctcgcagagc ttccgtatat tgatgccata    960
ttaaaagaga gtttgcgctt gatgcctact gccctggct tcgccgtcac tccaaagaag    1020
acggaggttc tgggcgggaa atggatgatc aatgccggtc aacccgtcaa tgtcctactg    1080
cctgcctgtc tacgagatca gagtgtcttc ggacccgacg cagacgagtt ccaccctgaa    1140
cgtatgttgg cagagaattt ctctaagctg cctcccaact cgtggaaacc gtttggtaat    1200
ggtgaacgag gctgcattgg cagggctttt gcttggcaag aagcccaact cgtggttgcc    1260
atgattctac aaacgtttga tttggtgcca gacgacccgt cctaccagct gcgcatcaaa    1320
gagactctca ccattaagcc agatggattt cggatccgtg ccctactgcg ccgcggtcag    1380
actgccactg ggctatctcg acgtagcatg ttagtggcga gggatgggag ctcaggggaa    1440
tcgtcaaatc atctcgctga ggcccgcgga gaccacgcac cagcaagagg gcagccggtt    1500
tccttcttct acggctctaa cagcggaaca tgcaaagccc tcgcccacca gttagcatcg    1560
aatatgatgt cccgcggata tactacccag aagctggctc cgctagataa tgccgtcggc    1620
aacctaccga gagatcagcc agtcatcatt ctaacaacca cgtacgatgg gcagcccaca    1680
gatgatgcga agaagtttgt ggcctggctc gaaactggca atgttccgtc tcttcagggc    1740
atatcctacg ctgtattcgg ctgcggccat catgactgga ctcaaacttt ctatcgcatc    1800
cccatcttga ttgatgacct gatgcacaag gccggcgcca cacgccttgc gccacgaggt    1860
gcagctaatg cggctgtcag tgatctcttc tcggatctgg aagcatggga agaaacaagt    1920
ctgctgcccg ctcttagaga gaacttcctc ccatccaaca gcaccgactt cgatccgctc    1980 aaccccacc agatacagct tagtctcagt aagcccagga gggtggacct gcacaagggt    2040
cttatagagg caaaagtgac tgctgtccgg gtcttaacta gccccgacac cccggagaag    2100
cgacatcttg aattttgctt ccagggcgac accagcttgc gaccaggtga tcatcttaat    2160
attctcccag ttaatccgcc cagcaccgtc tcgcgagtcc tggcgcagtt caacctcgca    2220
ccggattaca acatcacagt caattcattc aacacacttg gtctccccca agccacacct    2280
gtgtcggcat ccgagctatt tagctcgtac gtagagctat gccaaccagc gacacggaat    2340
aacctcaaag cactcatcgc agccacacaa tcagatccag acaaacaaga attgaaccgc    2400
ctgtacgatt catacgagtt catagttcgg gacaaacgcg tctcagtgtt ggatctcctt    2460
gagcagttcc cctctatctc ccttcctatc gccgctttta tctccatgct cccagctctc    2520
cgcgtccgga catattcctt atcaatggct ccctcgttca aaccatccca cagctcgctc    2580
accttctccg tgatcaacga gccagcatgg cgcggcagtg gacagcatct gggcgtcgca    2640
tcgaactacc tggcatcgct cacatcaggg tccattttct acttctctcc ccgaccagcc    2700
aaggagtctt tccatcttcc gaaggaccct tccaacacac ctatcatcat gatctgcgcg    2760
ggtagcggtc tagccccttt ccttagcttt atacaagacc gcatggtctt gaaacagcag    2820
tacaaaccac tcgcgaaggc atttctgttc tttggctgcc gtgggcgctc cttggatgac    2880
ctttaccatg aagaactatc tgagtttgaa gctgcgggtg tggttgagat tcggagagca    2940
tatagtaaaa ctccagattt cgacatagct aaaggatgtc gatatgtgca acatcgactg    3000
gtgacagaag gtcaagcgat cctgtctctt tggtcacaga atgctacaat ctatgtctgc    3060
ggctcgacga acatggccaa gggggtcgag gccgtgttac agaatatgtt gggccctttg    3120
ccaaaggagc gatatgttac ggagatcttt taa                                  3153

<210> SEQ ID NO 19
<211> LENGTH: 3150
```

```
<212> TYPE: DNA
<213> ORGANISM: Artificial Sequence
<220> FEATURE:
<223> OTHER INFORMATION: Sequence of wild-type gene prepared for cloning
      into Pichia pastoris

<400> SEQUENCE: 19
atgaaagata tggattgtat tcccggacca aaacccctgc cagtggtggg aaatctgttc      60
gacctcgacc tcgacaatgc cctacagtct atcatcagaa tggcggacga gttcggaccc     120
ctcttccaaa ttaccataaa cggccagaag cagatctttg ccactagcca ggctctggtc     180
gatgagcttt gtgacgaaac ccgcttccac aaggccgtca tgggcggagt tgaaaagtta     240
cgaatgctgg cccaggatgg tctcttcacg gcccatcatg gagagcgcgg ttgggggtatt     300 gctcatcgga ttctgatgcc tgcatttggc ccgctacgta tccgcgacat gttcgaggat     360
atgagcgatg ttgcgcacca gttgtgtttc aagtgggccc gccagggaag ttcggccagt     420
atcaatatcg ccgaggattt tacccgcctc acactagaca ccatcgccct ctgcacgatg     480
agtttccggt tgaatagcta ttacaacagt gagacaatgc acccatttgt acaatccatg     540
ctatacgtgt tgaaggaagc cgacctccag gcaacgcttc cggggtcgc aaactgcgtg      600 cgtgtcaagg cgcagcggcg catgtccaag cacatccagg caatgaggaa catagccggc     660
gacatcatca agggcgcag agacaaacca gaaccggtag acgacctctt aaacacacta      720
ctgaacgggc gtgacccagt caccggtgaa ggcatgagcg atgagttgat catcagcaac     780
attattacct tcttggtcgc gggccatgag actacctctg gtctattgtc tttcacattc     840
tattacctgc tacaacatcc acatgttttg gaacaggccc ggaacgaagt cgatgaggtg     900
gtcggtgtgg ggccaatcac agtgcagcat ctagcaaaac ttccttacat cgatgcagtc     960
atgaaggaga gtttgcgcct gatgcccacc gccccggcct ttacagtcac accgaagaag    1020
ccagaggtgg tgggtggcaa atggatggtc ataccgggc aatctgttca tgtactgctg     1080
cctgtatgtc tgcgagacga ggctgtattt gggcccgacg cggcgagtt tcgcccgacc     1140 cgtatgctgg aagagaactt ctccaagctc ccacctaact catggaaacc ctttggtaac    1200
ggcgaacgcg gctgcattgg tagggcattt gcctggcagg aagctcaact ggtggttgcc    1260
tcggtccttc aaacgtttga cttggtagca gaggacccctt actataaact gcgcatcaaa   1320
gagactctta caatcaagcc cgatggcttt cgggtccgag caaccctgcg tcgcggccag    1380
agtgccacgg cgctatccca acacaatatg tcggcgggcg ctactgccag cccggggtcc    1440
tccactcatc tagccgggga cgagaacggc caggatacag cgggaggtca acctatttcc    1500
ttcttctacg gttccaacag cggaacatgc aaggctctcg cccaccgcct ggcatcaacc    1560
atgatgactc gcggatttac cgaccagcat ctagcgcaac tcgatagcgc cgtagacaat    1620
ctgccgagag atcagccaac gattatcgta accactactt acgacgggca gcccacggac    1680
gacgcgaaga aatttctcgc ctggcttgaa agcggaaatg tcccatctct tcatggcgtt    1740
tcttacgcag tttttggctg tggtcatcaa gactggacca agacattcta tcgcattccg    1800
atcttgatcg atgacctaat gcataaggct ggagccacgc gtctcacaac cagagggaca    1860
gccaatgccg ctgtcagcga tctcttctcg gatctgaag tgtgggaaga gaccaaccta     1920
ctgcccgccc ttcgggagaa gttctacctc tgcaacagca gcgacttcga accactagat    1980
ccgcaccagc tccagatcag catcagcaaa cccgcaaggg tgggcatgca ccggacctc     2040 gtcgaaggta aggtgactgc catccggaca ctaacaagcc ccggggttcc ggagaagcga    2100
catgttgagt tccagatccc gagcgagatg gccctccgcc caggcgacca tgtcaatatc    2160
```

```
ctccccgtca atccaccctg ctcggtattg agagcactag ctcgattcag tctcgcgtcg    2220
gatcacagca tcacgttcga gtcttccaac gcactcgatc tgccccaggc cacaccagtg    2280
tcggcggccg aactttcag ctcgtatctg gagctatctc aaccggcaac gcggattaat    2340
ctcaaaagcc tcgcctctgc cactccgtca gatgatgaca aaaaggagct gctccatttc    2400
cacgattctt acgattcact tatccgagat aagcgtgtct cggtcttgga tctcctcgaa    2460
cacttcacct cgatcacact tcctatcgcc acatttatct ccatgctccc cgttttgcgc    2520
gttcgcactt actcccttc aatggccccc tccttcaagc ctttgcactg ttcgctcacc    2580
ttctccgtcg tcaacgagcc agcatggagc gggaatggtc gatatctagg cgtcggatcc    2640
aactatctcg cctcgctgac cccaggatcc attctatatg tatcccccgcg accagccaag    2700 gacgccttcc atctgccgac agaccagtcc agcaatccaa tcatcatgat ctgcgcaggg    2760
agtggccttg cccccttccg cagctttatc caagaccgca tggcatggct gcaacagggc    2820
aaaccactcg caaaggcgct gttgttcttc ggctgtcgcg gtccccacct cgatgatctc    2880
taccacgacg aattatccga gtttgaatct gcgggtgtgg tcgaggtccg gagggcgtac    2940
agtaaagttc cgaaccacta cctagccaag ggatgccggt atgcacagca ccggttgctt    3000
accgaaactg agaccatcca ggacatgtgg gctcacaatg ccacactcta tctctgcggt    3060
tcggccaacc tggccaaggg agtcaaggcc gtgttggaga atatgttggg cactttatct    3120
gaagagcgat atattacgga gatttttag                                      3150
```

PROCESS FOR THE MODIFICATION OF ALKANES, FATTY ACIDS AND FATTY ALCOHOLS

CROSS REFERENCE TO RELATED APPLICATIONS

This application is a National Stage Application of International Application Number PCT/IB2017/050732, filed Feb. 10, 2017; which claims priority to United Kingdom Application No. 1602574.4, filed Feb. 12, 2016; both of which are incorporated herein by reference in their entirety.

The Sequence Listing for this application is labeled "SeqList-03Mar18-ST25.txt", which was created on Mar. 3, 2018, and is 137 KB. The entire content is incorporated herein by reference in its entirety.

TECHNICAL FIELD

The present invention relates to a process for the microbial in-chain hydroxylation of fatty acids, alcohols and alkanes to produce bioflavour compounds. The invention further relates to the use of Cytochrome P450 monooxygenases to carry out the in-chain hydroxylation.

BACKGROUND ART

Since time immemorial, man has unwittingly used microorganisms to produce flavours, especially when preparing fermented foods and drinks, the original benefit being the increased shelf life of such products. It was only around the turn of the 20$^{th}$ century, that the relationship between the typical desirable flavour of fermented foods and beverages, and the microorganisms involved became recognized (Vandamme, 2003).

Further analysis and optimisation of food fermentations, led to the study of pure microbial strains as to their capacity to produce specific single flavour molecules either de novo or by converting an added substrate/precursor molecule. In only a few cases, detailed research has led to the identification of the biochemical pathways involved, but much work still lays ahead here; similarly several enzymes/enzyme systems have been characterised and are now being exploited for enzymatic flavour synthesis.

Flavours and fragrances nowadays have a wide application in the food, feed, cosmetic, chemical and pharmaceutical sector. Many flavour compounds on the market are still produced via chemical synthesis or via extraction from plant and animal sources; however, a rapid switch towards the bio-production and use of flavour compounds of (micro) biological origin—bioflavours—is observed. Reasons are among others, the fact that chemical synthesis results often in an environmentally unfriendly production process and in undesirable racemic mixture compounds. Furthermore, the consumer has developed a "chemophobia"-attitude towards chemical or synthetic (even nature-identical) compounds, especially when related to his food and home-care products (Vandamme, 2003).

Products that occur in nature but are now produced via a chemical (a non-natural) process are called "nature-identical"; this mode of production is no longer accepted as consumer friendly.

The word "natural" is defined legally by American and European regulations (CFR 1990 and the European regulation CE 1334/2008) and a substance can be considered as natural when it comes from a plant, animal or microbial origin with a physical, microbial or enzymatic process.

Up to now, certain plant and animal sources remain an important source of bioflavours, but these bio-active compounds are often present in minor quantities, making extraction, isolation and formulation very expensive, or they are found only in exotic (plant) species.

The other bio-route for flavour synthesis is based on de novo microbial processes (fermentation) or on bioconversions of natural precursors with microbial cells or enzymes (biocatalysis). Biotechnological processes usually require less damaging process conditions to the environment and yield the desirable enantiomeric flavour compound.

A bottleneck often still is a lack of Fungal Diversity knowledge about the biochemical pathways, the enzymes and the metabolic (de)regulation involved, to obtain high yields (Vandamme, 2003). Nevertheless, bioflavours/biofragrances appeal to many sectors and represent already a high market value.

Lactones represent an important class of substances with applications not only in polymer synthesis but also as environmentally benign solvents, fuels, flavours, fragrances and as building blocks for synthesis. Depending on the compounds, lactones exhibit fruity and oily properties with peach, apricot or coconut notes. Among them, the pathway to γ-decalactone was first discovered by Okui et al. in 1963 and the resulting lactone is now the compound which is the most produced through biotechnology. It is used in many aroma and cosmetic preparations. It can be easily obtained from hydroxy fatty acids by a yeast transformation.

Cytochrome P450 (CYP) belongs to the superfamily of proteins containing a heme prosthetic group and, therefore, is referred to as a hemoprotein. CYPs use a variety of small and large molecules as substrates in enzymatic reactions. CYP enzymes have been identified in all domains of life—animals, plants, fungi, protists, bacteria, archaea, and even in viruses. The most common reaction catalyzed by cytochromes P450 is a monooxygenase reaction, e.g., insertion of one atom of oxygen into a carbon-hydrogen bond of an organic substrate (RH) while the other oxygen atom is reduced to water:

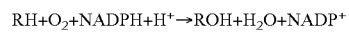

$$RH+O_2+NADPH+H^+ \rightarrow ROH+H_2O+NADP^+$$

Microbial monooxygenase/hydroxylase enzymes involved in the metabolism of endogenous and xenobiotic compounds have potential application in many areas including organic synthesis and production of pharmaceutically and other industrially useful compounds.

The filamentous fungi carry genes encoding an array of CYP450 enzymes essential in fungal pathogenesis, xenobiotic degradation and substrate utilization (Moktali et al., 2012).

The oxidation of substrates catalysed by CYP450s requires additional electron transfer proteins, also known as redox partner proteins, which transfer electrons from reduced cofactors to the heme. However, the discovery of a naturally fused self-sufficient system in Bacillus megaterium (CYP102A1) solved the fundamental need of a separate redox partner protein (Li et al., 2007).

The first identified fungal self-sufficient system was a sub-terminal fatty acid hydroxylase (CYP505A1) from Fusarium oxysporum which catalyses ω-1 to ω-3 hydroxylation of medium chain fatty acids (Crešnar & Petrič, 2011). The presence of members of the CYP505 family is fairly conserved within the filamentous fungi (Syed et al., 2014).

Vatsyayan and co-workers (2008) investigated the substrate specificity of the filamentous fungus Aspergillus terreus. CYP450s obtained from cells grown on glucose or n-hexadecane were studied. CYP450 distribution from the n-hexadecane grown cells was contained mainly in the cytosol while the CYP450s obtained from the glucose grown cells were obtained in the microsomes. The CYP450 containing microsomal fractions showed activity towards alkanes, alkane derivatives, alcohols, aromatic compounds, organic solvents, and steroids. Only two products were isolated and identified. The product from ethanol was identified as glycolic acid, and the product from hexadecane as 1-hexadecanal-8-one.

SDS-PAGE analysis of the microsomal protein fraction after heme staining indicated that there was only a single heme protein present. The molecular weight of the heme stained protein band was approximately 110 kDa when compared with standard protein markers. It was reported that the size of the single heme stained protein band corresponded to the self-sufficient *Fusarium oxysporum* CYP505A1 reported by Nakayama and co-workers (1996). Hence, the protein band was presumed to be a self-sufficient CYP450 in *A. terreus* and it was claimed that this self-sufficient CYP450 had both terminal and sub-terminal hydroxylase activity.

The genome of the filamentous fungus *A. terreus* comprises 10,406 open reading frames with 125 annotated as CYP450 genes (Park et al., 2008). Only two of these 125 CYP450 genes encode possible self-sufficient CYP450s. These two putative self-sufficient CYPs in the genome of *A. terreus* have been classified as CYP505A19 and CYP505E3.

One of the identified self-sufficient CYP450, CYP505A19 lacks a crucial segment of the heme domain, while there is also a large deletion in the reductase domain (Kuloyo, 2014). It was postulated that this protein will not fold properly and would be inactive or, alternatively, it would not accept small molecules such as alkanes as substrates. The second of these self-sufficient CYP450s, designated as CYP505E3, was heterologously expressed in *E. coli* but reported to display no detectable activity towards alkanes and alkylbenzens in whole cell biotransformations, while it hydroxylated hexylbenzoic acid to yield products hydroxylated at positions ω-1, ω-2 and ω-4. It was thus also assumed to be a sub-terminal fatty acid hydroxylase (Kuloyo, 2014).

Given the deficiencies of the prior art, there exists a present need for further investigation into the use of CYPs for the specific hydroxylation of organic substrates to produce bioflavour compounds, including lactones.

It is accordingly an object of the present invention to provide for the use of CYP505E3 and related fungal cytochrome P450 monooxygenases in the in-chain hydroxylation at position ω-7 of, inter alia, alkanes, fatty alcohols and fatty acid substrates (FIG. 1) as precursors for the synthesis of lactones, esters and, inter alia, polymers.

SUMMARY OF THE INVENTION

In accordance with the present specification, the terms "cytochrome P450 monooxygenase," "cytochrome P450," "P450", "CYP" and "CYP450" are used interchangeably herein. They comprise a large number of polypeptides that are grouped into families based on sequence homology.

According to a first aspect thereof, the present invention provides a process for the microbiological in-chain hydroxylation of C12 to C16 fatty acids, alcohols and/or alkanes at position ω-7 which process includes the steps of culturing a microorganism expressing a recombinant cytochrome P450 monooxygenase of amino acid sequences with at least 70% sequence identity to SEQ ID Nos: 1, 2, 3, 4, 5, 6 or 7 on a culture medium including an exogenous substrate, and isolating a hydroxylated product or secondary product formed thereof from the medium; wherein the exogenous substrate is selected from the group consisting of C12 to C16 fatty acids, alcohols or alkanes.

In a further embodiment, the invention includes the further step of creating a Cell-Free Extract (CFE) of the cultured microorganism and combining the CFE with a medium containing the exogenous substrate. In a yet further embodiment of the invention, the microorganism is a wild-type *Aspergillus terreus* strain or other wild-type fungal strain expressing CYP450s with at least 70% sequence identity to amino acid SEQ ID Nos: 1, 2, 3, 4, 5, 6 or 7.

In an embodiment of the invention, the cytochrome P450 monooxygenase may have at least 80% sequence identity to the amino acid sequences of SEQ ID Nos: 1, 2, 3, 4, 5, 6 or 7. In a further embodiment of the invention, the cytochrome P450 monooxygenase may have at least 90% sequence identity to the amino acid sequences of SEQ ID Nos: 1, 2, 3, 4, 5, 6 or 7.

In an embodiment of the invention, the C12 to C16 fatty acid described in any of the above may include any C12 to C16 saturated, unsaturated, straight or branched fatty acid. In one embodiment of the invention, the C12 to C16 fatty acid includes, but is not limited to, lauric acid (also known as dodecanoic acid), tridecylic acid, myristic acid (also known as tetradecanoic acid), pentadecylic acid and palmitic acid (also known as hexadecanoic acid).

In a further embodiment of the invention, the C12 to C16 alcohol described in any of the above may include any C12 to C16 saturated, unsaturated, straight or branched alcohol. In one embodiment of the invention, the C12 to C16 alcohol includes, but is not limited to, lauryl alcohol (also known as 1-dodecanol), tridecyl alcohol, myristyl alcohol (also known as 1-tetradecanol), pentadecyl alcohol, cetyl alcohol and palmitoleyl alcohol.

In another embodiment of the invention, the C12 to C16 alkane as described in any of the above may include any C12 to C16 saturated, unsaturated, branched or unbranched alkane. In one embodiment of the invention, the C12 to C16 alkane includes, but is not limited to, dodecane, tridecane, tetradecane, pentadecane and hexadecane.

The present invention also relates to a process for the microbiological production of lactones, esters and/or polymers, which process includes the steps described herein above.

In an embodiment of the invention, the lactone produced by the present invention as described herein above is delta dodecalactone (δ-dodecalactone).

In an embodiment of the invention, the esters produced by the present invention as described herein above include heptyl pentanoate, butyl octanoate, heptyl nonanoate, hexyl octanoate, and heptyl heptanoate.

In another embodiment of the invention, the polymers produced by the present invention as described herein above include poly(δ-dodecalactone).

The present invention also relates to the use of a cytochrome P450 monooxygenase having an amino acid sequence with at least 70% sequence identity to SEQ ID Nos: 1, 2, 3, 4, 5, 6 or 7 for the microbiological in-chain hydroxylation of C12 to C16 fatty acids, alcohols and/or alkanes at position ω-7 to precursors for the synthesis of lactones, esters and/or polymers.

The present invention also relates to a nucleic acid coding for a cytochrome P450 monooxygenase amino acid sequence with at least 70% sequence identity to SEQ ID Nos: 1, 2, 3, 4, 5, 6 or 7, which may comprise the nucleic acid sequence of SEQ ID Nos: 13, 14, 15, 16, 17, 18 or 19, or a nucleic acid sequence with at least 70% sequence identity to SEQ ID Nos: 13, 14, 15, 16, 17, 18 or 19.

The present invention also relates to the use of a vector comprising at least one expression construct comprising, under the genetic control of regulatory nucleic acid sequences, a coding sequence comprising a nucleic acid sequence coding for a cytochrome P450 monooxygenase as described above, or a recombinant microorganism comprising at least one such vector for the microbiological in-chain hydroxylation of C12 to C16 fatty acids, alcohols and/or alkanes at position ω-7 to precursors for the synthesis of lactones, esters and/or polymers.

The invention thus relates to expression constructs comprising a nucleic acid sequence coding a cytochrome P450 monooxygenase as described above under the genetic control of regulatory nucleic acid sequences; and vectors comprising at least one of these expression constructs.

The choice of recombinant expression construct is dependent upon the method that will be used to transform host cells. The skilled artisan is well aware of the genetic elements that must be present on the recombinant expression construct in order to successfully transform, select and propagate host cells. The skilled artisan will also recognize that different independent transformation events may be screened to obtain lines displaying the desired expression level and pattern. Such screening may be accomplished by, but is not limited to, Southern analysis of DNA, Northern analysis of mRNA expression, Western analysis of protein expression, or phenotypic analysis.

The term "alignment" refers to the process or result of matching up the nucleotide or amino acid residues of two or more biological sequences to achieve maximal levels of identity and, in the case of amino acid sequences, conservation, for the purpose of assessing the degree of similarity and the possibility of homology.

The term "coding sequence" refers to a DNA fragment that codes for a structural RNA, or for a polypeptide having a specific amino acid sequence. The boundaries of a protein coding sequence are generally determined by a ribosome binding site (prokaryotes) or by a start codon (eukaryotes) located at the 5' end of the mRNA and a transcription terminator sequence located just downstream of the open reading frame at the 3' end of the mRNA. A coding sequence can include, but is not limited to, DNA, cDNA, exons, and recombinant nucleic acid sequences.

"Homology" refers to similarity which can be attributed to descent from a common ancestor.

"Regulatory sequences" refer to nucleotides located upstream (5' non-coding sequences), within, or downstream (3' non-coding sequences) of a coding sequence, which may influence the transcription, RNA processing, stability, or translation of the associated coding sequence. Regulatory sequences may include, but are not limited to, promoters, translation leader sequences, introns, and polyadenylation recognition sequences.

"Promoter" refers to a region of DNA capable of controlling the expression of a coding sequence or functional RNA. The promoter may consist of proximal and more distal upstream elements. These upstream elements include, but are not limited to, enhancers, repressor binding motifs, tissue-specific motifs, developmental responsive motifs, and hormone responsive motifs.

A number of promoters can be used in the practice of the present invention. The promoters can be selected based on the desired outcome. Nucleic acids used to accomplish the invention can be combined in any host organism with a promoter or element that has constitutive, tissue-specific, inducible, or other gene regulatory activities.

Examples of suitable promoters for use in the present invention include cos, tac, trp, tet, trp-tet, lpp, lac, lpp-lac, laclq, T7, T5, T3, gal, trc, ara, SP6, I-PR or I-PL promoters, which are advantageously employed in Gram-negative bacteria.

For expression in a suitable host organism, the recombinant expression construct is inserted into a host-specific vector which allows optimal gene expression in the host. Vectors are well known to the skilled worker and can be found in many well known books, for example, in "Cloning Vectors" (Pouwels P. H. et al., Ed., Elsevier, Amsterdam-New York-Oxford, 1985).

Vectors are to be understood as meaning not only plasmids, but all other vectors known to the skilled worker such as, for example, phages, viruses, such as SV40, CMV, baculovirus and adenovirus, transposons, IS elements, phasmids, cosmids, and linear or circular DNA. These vectors can be replicated autonomously in the host organism or chromosomally.

The vectors according to the invention allow the generation of recombinant microorganisms which are transformed, for example, with at least one vector according to the invention. In an embodiment of the invention, the vector is pET28b vector.

The above-described recombinant constructs according to the invention are advantageously introduced into a suitable host system and expressed.

Suitable host organisms are, in principle, all organisms which allow expression of the nucleic acids according to the invention, their allelic variants, and their functional equivalents or derivatives. Host organisms are to be understood as meaning, for example, bacteria, fungi, yeasts or plant or animal cells.

In terms of the present invention, the preferred host organisms are *Escherichia coli*, particularly *Escherichia coli* BL21 (DE3) strains and yeasts such as *Pichia pastoris* and *Yarrowia lipolytica*.

The skilled artisan is well aware of the genetic elements that must be present on the vector in order to successfully transform, select and propagate host cells comprising any of the isolated nucleic acid fragments of the invention. Screening to obtain lines displaying the desired expression level and pattern may be accomplished by Southern analysis of DNA, Northern analysis of mRNA expression, RT-PCR, immunoblotting analysis of protein expression, or phenotypic analysis, among others.

The term "expression," as used herein refers to the transcription and stable accumulation of sense (mRNA) or antisense RNA derived from a polynucleotide of the invention. Expression may also refer to translation of mRNA into a polypeptide.

"Sequence identity" refers to the extent to which two (nucleotide or amino acid) sequences have the same residues at the same positions in an alignment, often expressed as a percentage.

The term "similarity" refers to the extent to which nucleotide or protein sequences are related. Similarity between two sequences are generally expressed in the art in terms of percent sequence identity or percent positive substitutions.

"Transformation" refers to the transfer of a nucleic acid fragment into the genome of a host organism, resulting in genetically stable inheritance. Host organisms containing the transformed nucleic acid fragments are referred to as "transgenic" organisms.

Standard recombinant DNA and molecular cloning techniques used herein are well known in the art and are described more fully in Sambrook et al. Molecular Cloning: A Laboratory Manual; Cold Spring Harbor Laboratory Press: Cold Spring Harbor, 1989 (hereinafter "Sambrook").

These and other aspects of the present invention will now be described in more detail herein and below.

BRIEF DESCRIPTION OF THE FIGURES

The invention will now be described in more detail, by way of example only, with reference to the accompanying figures in which.

Figure 24:
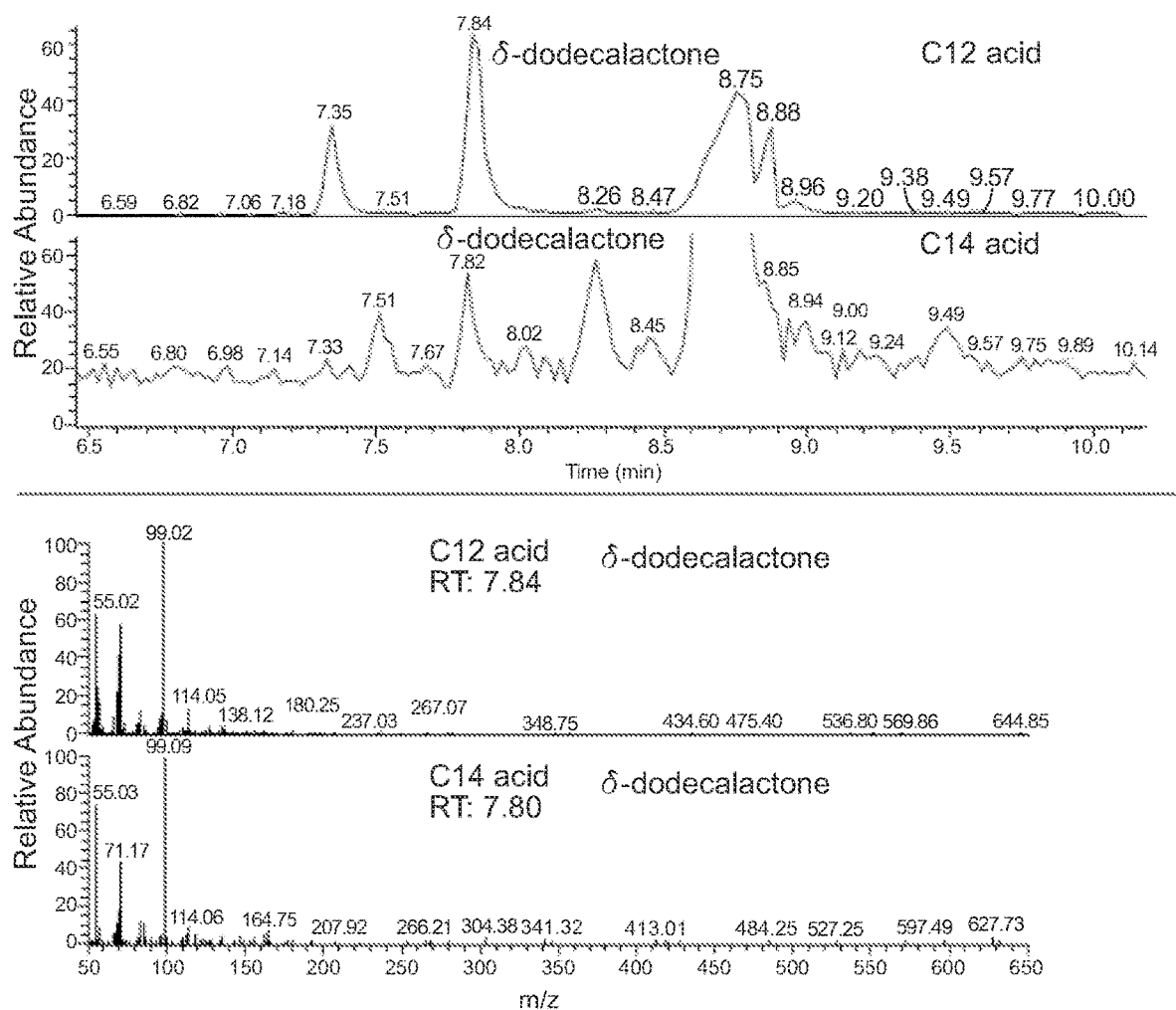

FIG. 23: Shows a table of amino acid identities of the 12 different CYP505s tested. These sequences (SEQ ID Nos 1 to 12) were aligned and identities calculated using the MUSCLE algorithm as applied in the Genious 6.0.6 software package; and FIG. 24: Depicts GC-MS analyses of samples from the whole cell biotransformations of dodecanoic acid and tetradecanoic acid by whole cells of *P. pastoris* expressing CYP505An (SEQ ID No 5) to produce δ-dodecalactone. When using tetradecanoic acid as substrate δ-dodecalactone was produced via one round of β-oxidation.

The foregoing and other objects and features and advantages of the present invention will become more apparent from the following description of certain embodiments of the present invention by way of the following non-limiting examples.

DESCRIPTION OF THE INVENTION

The invention will now be described with reference to the following non-limiting experimental examples.

Materials and Methods and General Experimental Procedures

Chemicals and Enzymes

Chemicals and reagents used in these experiments were analytical grade and were, unless otherwise stated, supplied by either Fluka, Sigma-Aldrich or Merck.

Cloning of Enzymes

The gene encoding CYP505E3 from *Aspergillus terreus* was codon optimized for expression in *E. coli* and synthesized by Genscript. The gene encoding CYP505A1 was synthesized by GeneArt without any codon optimization, but with common restriction enzyme recognition sites removed. The genes encoding CYP505E3 and CYP505A1 were cloned into the pET28b(+) plasmid. The gene encoding the glucose dehydrogenase (GDH) from *Bacillus megaterium* (GDH), was cloned into pETDuet (Novagen) multiple cloning site 2 (MC2). The gene encoding horse liver alcohol dehydrogenase (HLADH) was cloned into pET28b(+). For expression of the CYPs, GDH and HLADH, *E. coli* BL21-Gold(DE3) (Stratagene) was transformed with the relevant plasmids and transformants selected on LB-plates containing 30 μg·ml$^{-1}$ kanamycin or 100 μg·ml$^{-1}$ ampicillin.

The CYP505E3 gene optimized for expression in *Pichia pastoris* was synthesized and cloned into the pAO815 vector by GenScript. A combination of chemical and electroporation techniques were used to transform *P. pastoris* strain KM71 with the plasmid linearized with SalI to yield slow growing (His$^+$Mut$^s$) transformants on methanol. The genes encoding amino acid SEQ ID Nos: 2, 3 and 4 were codon optimized for expression in *E. coli* and synthesized by GenScript. These genes were cloned into the pET28b(+) as well as the pAO815 plasmid. The pET28b(+) plasmids with the genes were cloned into *E. coli*, but expression was not successful. The genes encoding amino acid SEQ ID Nos: 5 to 7 were synthesized by GenScript without any codon optimization, but with common restriction enzyme recognition sites removed, and also cloned into pAO815. The pAO815 plasmids with all these genes were cloned into *P. pastoris* KM71 to yield slow growing (His$^+$Mut$^s$) transformants on methanol.

Heterologous Expression of Enzymes in *E. coli* and Preparation of Cell Free Extracts (CFEs) and Whole Cell (WC) Suspensions Expression of genes in *E. coli* was performed by using ZYP-5052 auto-induction medium (Table 1) with in the case of the CYP 1 mM 5-aminolevulinic acid and 0.05 mM FeCl$_3$ added. The CYP505E3 culture was cultivated using baffled flasks and incubated at 20° C. and 180 rpm for 24 h, while the GDH, and HLADH expressing cultures were all cultivated at 25° C. and 200 rpm for 24 h. Cultures were harvested through centrifugation (6 000×g, 10 min) and 1 g (wet weight) resuspended in 2 ml, 5 ml or 10 ml Tris-HCl, Phosphate or MOPS buffer, as indicated, (pH 8, 200 mM) containing 100 mM of glucose and glycerol. CFEs were obtained by a single passage of the suspended cells through a One Shot Cell Disrupter (Constant Systems) at 207 MPa. The soluble fraction was separated from unbroken cells by centrifugation (20 000×g, 20 min).

TABLE 1

Composition of ZY auto-induction media (Studier, 2005)

| | Stock solutions | | ZY auto-induction media |
|---|---|---|---|
| ZY medium | 20x NPS | 50x 5052* | 50 ml 20x NPS |
| 10 g/l tryptone | 0.5M (NH$_4$)$_2$SO$_4$ | 250 g/l glycerol | 20 ml 50x 5052 |
| 5 g/l yeast extract | 1M KH$_2$PO$_4$ | 25 g/l glucose | 2 ml 1M MgSO$_4$ |
| | 1M Na$_2$HPO$_4$ | 100 g/l α-lactose | 928 ml ZY-medium |

*5052 final concentrations—0.5% glycerol, 0.05% glucose, 0.2% α-lactose

Heterologous Expression of Enzymes in *P. pastoris* and Preparation of Whole Cell (WC) Suspensions Precultures of *P. pastoris* transformants were prepared in buffered complex glycerol media (BMGY). BMGY contained: 10 g/l yeast extract, 20 g/l peptone, 3.4 g/l yeast nitrogen base, 10 g/l ammonium sulfate, 100 mM potassium phosphate (pH 6), 0.4 mg/l biotin and 1% (v/v) glycerol. Erlenmeyer flasks (500 ml) containing 50 ml BMGY media were inoculated with single colonies of 24 h old YPD-agar cultures of *P. pastoris* KM71 mut$^{s3}$/CYP505E3 and incubated at 30° C. and 225 rpm for 24 h. The cultures were harvested using pre-weighed centrifuge tubes at 3000 g for 5 min and stored on ice until further use.

The main cultures for expression were prepared in buffered complex methanol media (BMMY) containing 10 g/l yeast extract, 20 g/l peptone, 3.4 g/l yeast nitrogen base, 10 g/l ammonium sulfate, 100 mM potassium phosphate (pH 6), 0.4 mg/l biotin and 0.5 or 1% (v/v) methanol. Harvested cells from precultures were resuspended in BMMY media to final concentration of 1 g WC per 40 ml (appx. 25 g/l). The resuspended cultures (100 ml) were transferred to 500 ml Erlenmeyer flasks and incubated at 25° C. and 225 rpm for 24 h. The cultures were then harvested at 3000 g for 5 min using pre-weighed centrifuge tubes.

Analyses

All chemicals were from Sigma-Aldrich and were used without further purification. Methylation of fatty acids was done with trimethylsulfonium hydroxide (TMSH) (1:1 EtOAc extract/TMSH reagent) and fatty acid containing samples analysed on a Restek BPX17 column (60 m×0.25 mm ID×0.25 μm film thickness). Samples containing only unmethylated fatty acids, alkanes, alcohols or lactones were analyzed on Varian FactorFour VF-5 ms column with dimensions: 30 m×0.25 mm×0.25 μm (length×inner diameter×film thickness).

GC-MS analyses were carried out on a Thermo Trace GC ultra chromatograph with DSQ mass spectrometer and standard GC analysis on a Shimadzu GC2010.

CO Difference Spectra

The resuspended cells were further diluted with phosphate buffer in a 1:1 (v/v) ratio to record CO difference spectra. The assay was conducted as described by Choi et al., (2003) using 200 μl of the diluted cells transferred into microtiter strips (Thermo Scientific). Absorbance readings between 400 and 500 nm were measured with a SpectraMax® Microplate Reader (Molecular Devices). The CYP450 concentration was determined using an extinction coefficient of 0.091 $nM^{-1}$ $ml^{-1}$ (Omura & Sato, 1964) and a pathlength of 0.596 cm. Peak corrections were done and CYP450 concentrations calculated by using the equation $A_{450}$−$((0.375*A_{470})+(0.625*A_{438}))/(0.091*0.596)$ (Johnston et al., 2008).

EXPERIMENTS

Experiment 1—Biotransformation of C12, C14 and C16 Fatty Acids and C14 and C16 Fatty Alcohols Using CFE of *E. coli* Expressing CYP505E3

The biotransformation reaction mixture (BRM) consisted of CYP and GDH CFE suspensions prepared from cells in Tris-HCl buffers (1 g wet weight in 2 ml buffer) mixed in a 1:1 ratio with 0.1 mM NADPH added. Dodecanoic acid, tetradecanoic acid, hexadecanoic acid, 1-tetradecanol and 1-hexadecanol (20 μl of a 255 mM stock solution in DMSO) were added to 40 ml amber glass vials containing 1 ml BRM to give final substrate concentrations of 5 mmol·$L_{BRM}^{-1}$. These vials were placed on an orbital shaker at 20° C., 200 rpm, oscillation amplitude 26 mm. Vials were removed after 24 h for extraction. Biotransformations were stopped by adding 170 ul of 0.5M HCl, extracted with 2×500 μl EtOAc and subjected to GC-MS analysis. A sample of δ-dodecalactone in ethyl acetate (0.1 mM) was also methylated with TMSH and subjected to GC-MS analysis.

Figure 1:
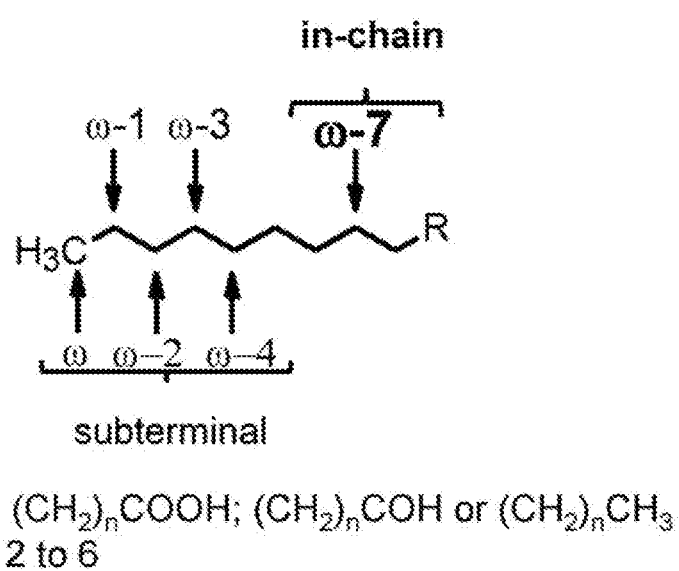
FIG. 1: Depicts the in-chain hydroxylation at position ω-7 of, alkanes, fatty alcohols and fatty acid substrates by a fungal cytochrome P450 monooxygenase.
Figure 2:
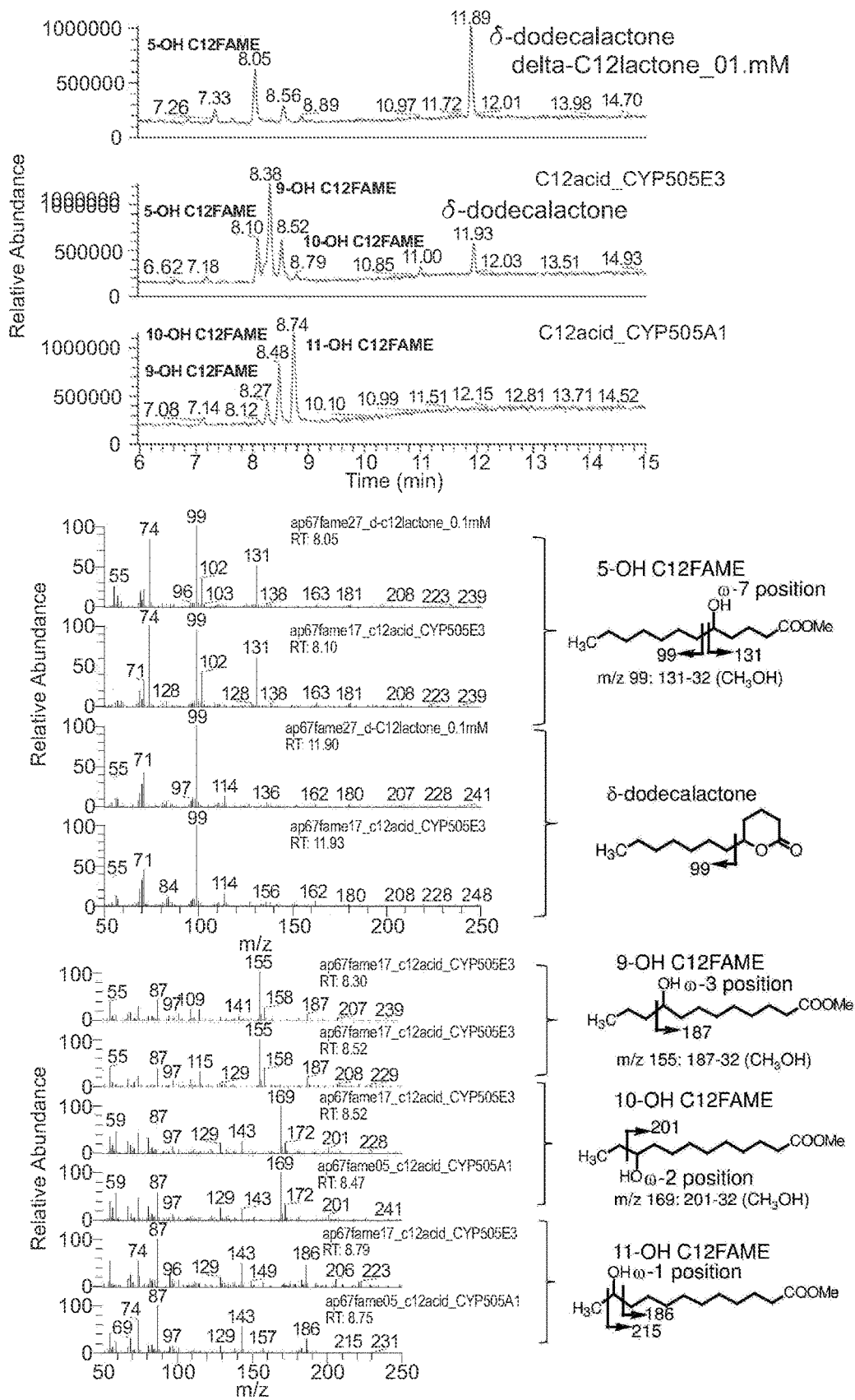
FIG. 2: Shows the GC-MS analyses results of the ethyl acetate extracts from biotransformations of dodecanoic acid carried out with CYP505E3 and CYP505A1 containing CFEs of *E. coli* in Tris_HCl buffer.

GC-MS chromatograms of the methylated samples from the dodecanoic acid biotransformations showed a complex mixture of products (FIG. 2). Two of these products in the extracts from the CYP505E3 reactions were identified as δ-dodecalactone and the methyl ester of 5-hydroxy dodecanoic acid (5OH 12FAME), by comparison of the GC chromatograms and mass spectra with those of methylated authentic δ-dodecalactone. The methyl ester of 5-hydroxy dodecanoic acid is formed when δ-dodecalactone is treated with TMSH. The other products formed by CYP505E3 were identified as the methyl esters of 9-, 10 and 11-hydroxydodecanoic acid (9OH 12FAME, 10OH 12FAME, 11OH 12FAME) by comparison with the products formed by CYP505A1 (Seq ID No 8), a known sub-terminal fatty acid hydroxylase of medium chain fatty acids (Nakayama et al., 1996).

Figure 3:
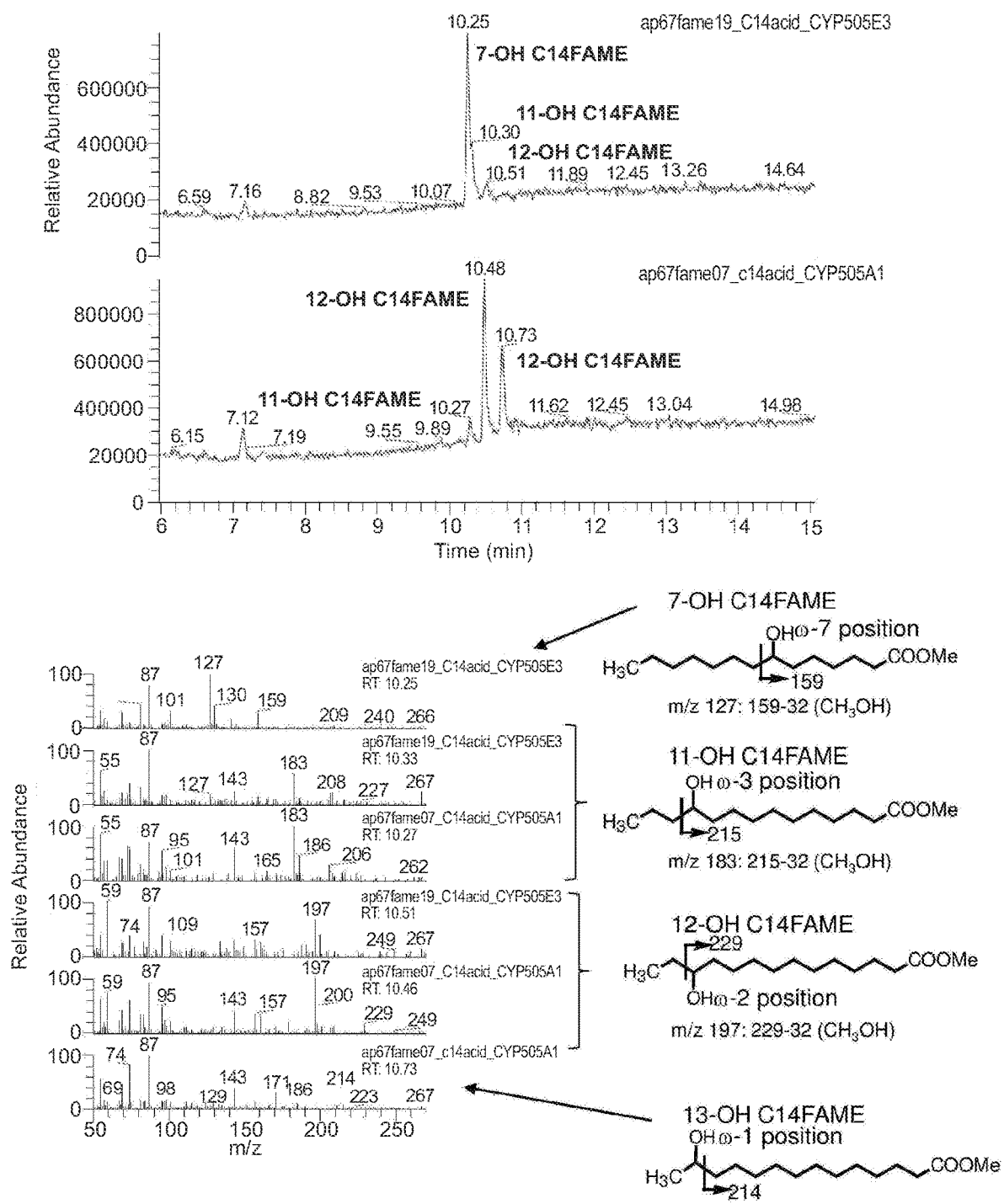
FIG. 3: Shows the GC-MS analyses results of the ethyl acetate extracts from biotransformations of tetradecanoic acid carried out with CYP505E3 and CYP505A1 containing CFEs of *E. coli* in Tris_HCl buffer.
Figure 4:
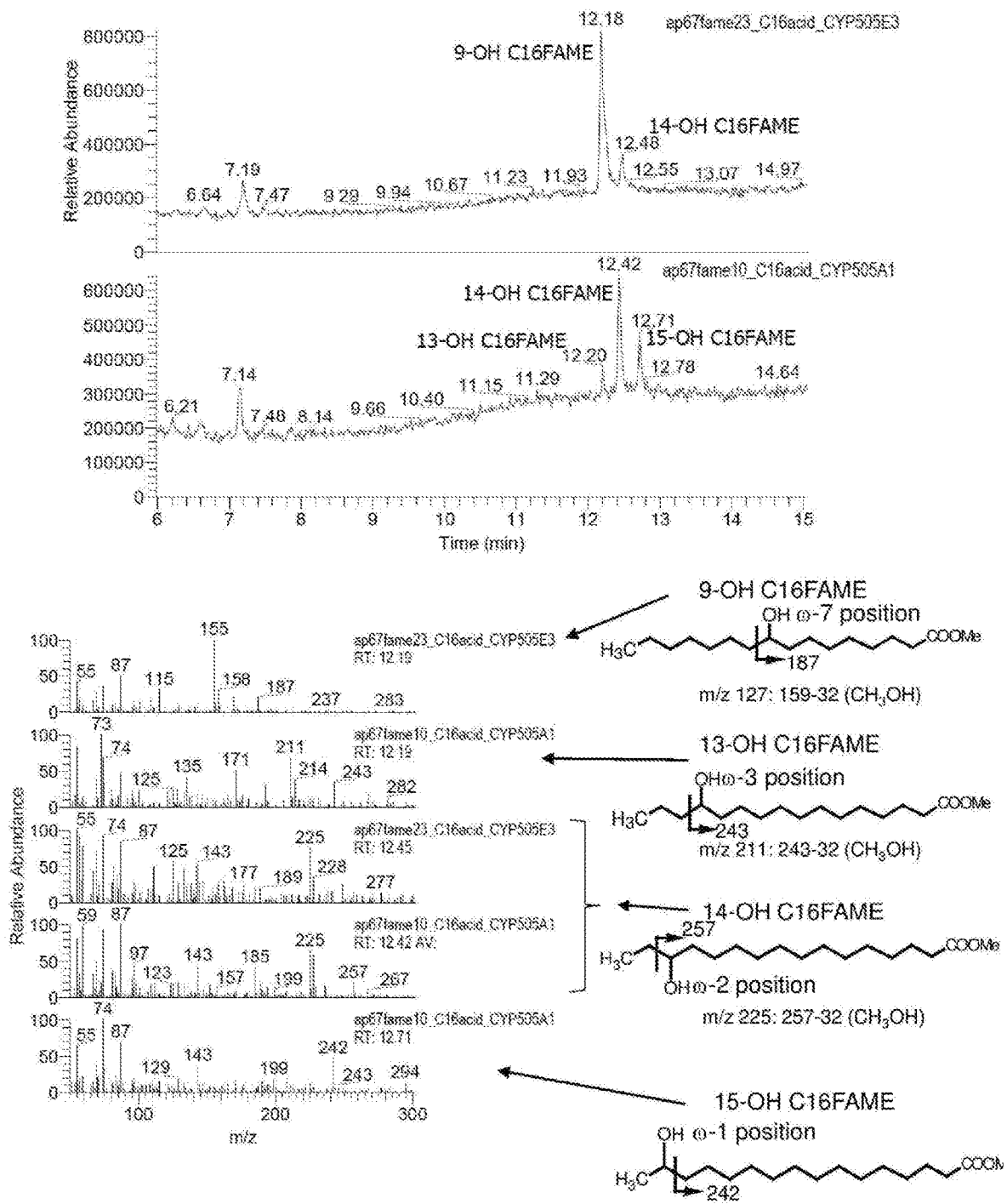
FIG. 4: Shows the GC-MS analyses results of the ethyl acetate extracts from biotransformations of hexadecanoic acid carried out with CYP505E3 and CYP505A1 containing CFEs of *E. coli* in Tris_HCl buffer.
Figure 5:
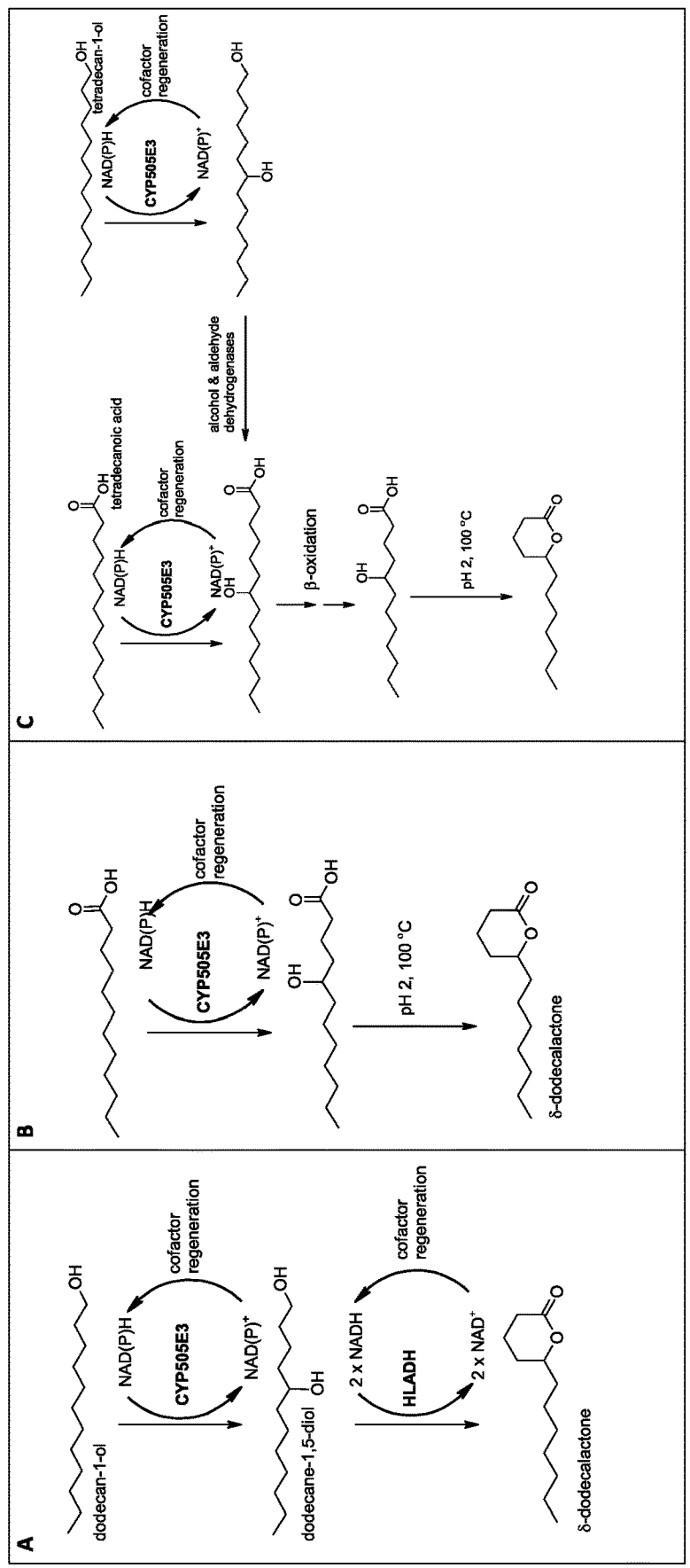
FIG. 5: Depicts the general scheme for the Production of δ-dodecalactone from 1-dodecanol (A); dodecanoic acid (B) and tetradecanoic acid or tetradecanol (C) via the in-chain hydroxylated products produced by CYP505E3. The route in C involves the use of viable yeast cells and can also be used for the products produced from hexadecanoic acid and hexadecanol.

GC-MS analysis of the methylated samples from the tretradecanoic acid and hexadecanoic acid biotransformations revealed in each case one major product which was different from the products produced by CYP505A1 and identified as the methyl esters of 7-hydroxy tetradecanoic acid (7-OH C14FAME) (FIG. 3) and 9-hydroxy hexadecanoic acid (9-OH C16FAME) (FIG. 4) by analysis of the mass spectra. One round of β-oxidation of 7-hydroxy tetradecanoic acid and two rounds of β-oxidation of 9-hydroxy hexadecanoic acid would in each case yield 5-hydroxy dodecanoic acid, which at low pH would cyclize to form δ-dodecalactone (FIG. 5). Thus CYP505E3 gives ω-7 hydroxylation of these fatty acids to yield precursors for the synthesis of δ-dodecalactone. CYP505A1 in comparison yielded from both substrates only sub-terminally hydroxylated products as described in the literature (Nakayama et al., 1996).

Figure 6:
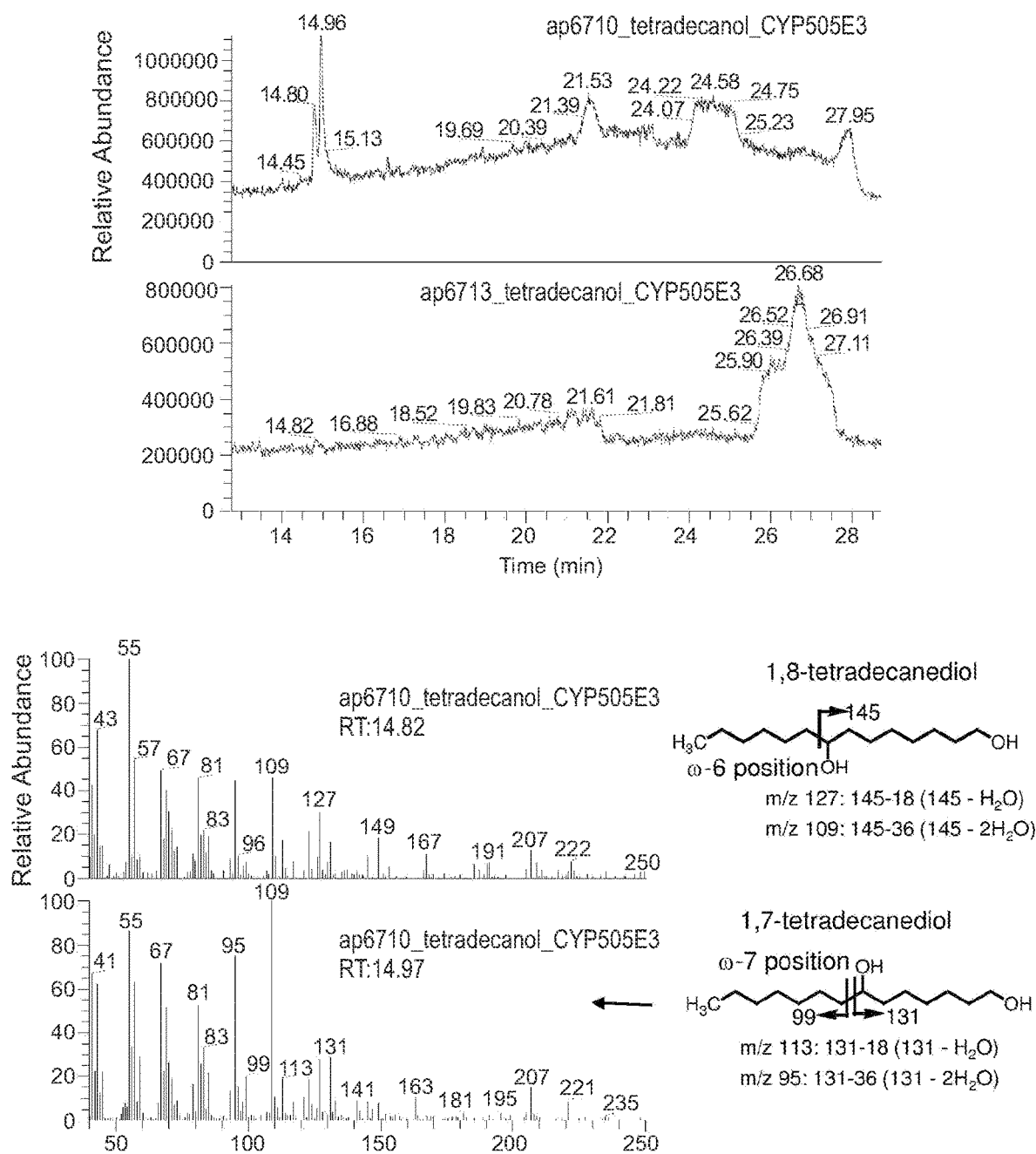
FIG. 6: Shows the GC-MS analyses results of the ethyl acetate extracts from biotransformations of tetradecanol carried out with CYP505E3 and CYP505A1 containing CFEs of *E. coli* in Tris_HCl buffer.

GC-MS analysis of the samples from the tetradecanol and hexadecanol biotransformations did not allow detection of any products formed from hexadecanol, while two products were detected in the samples from the tetradecanol biotransformations by CYP505E3 (FIG. 6). The mass spectra of these products were very similar. It was deduced that these products are 1,7-tetradecane diol and 1,8-tetradecane diol. 1,7-Tetradecane diol is also a ω-7 hydroxylation product and thus a precursor for the synthesis of δ-dodecalactone since oxidation would yield 7-hydroxy tetradecanoic acid which could then through one round of β-oxidation again give 5-hydroxy dodecanoic acid and ultimately δ-dodecalactone (FIG. 5).

Experiment 2—Biotransformation of C12 Fatty Acid Using CFE of *E. coli* Expressing CYP505E3 in Different Buffers The biotransformation reaction mixture (BRM) consisted of CYP and GDH CFE suspensions prepared from cells in Tris-HCl, phosphate and MOPS buffers (1 g wet weight in 5 ml buffer) mixed in a 1:1 ratio with 0.1 mM NADPH added. The final CYP concentrations were 1.1, 1.3 and 1.5 μM in respectively the Tris-HCl, phosphate and MOPS buffers. Dodecanoic acid (20 μl of 255 or 510 mM fatty acid stock solution in DMSO) was added to 40 ml amber glass vials containing 1 ml BRM to give final substrate concentrations of 5 and 10 mmol·$L_{BRM}^{-1}$. These vials were placed on an orbital shaker at 20° C., 200 rpm, oscillation amplitude 26 mm. Vials were removed at specific time intervals for extraction. Biotransformations were stopped by adding 170 ul of 0.5M HCl and extracted with 2×500 μl EtOAc containing 2 mM decanoic as internal standard.

Figure 7:
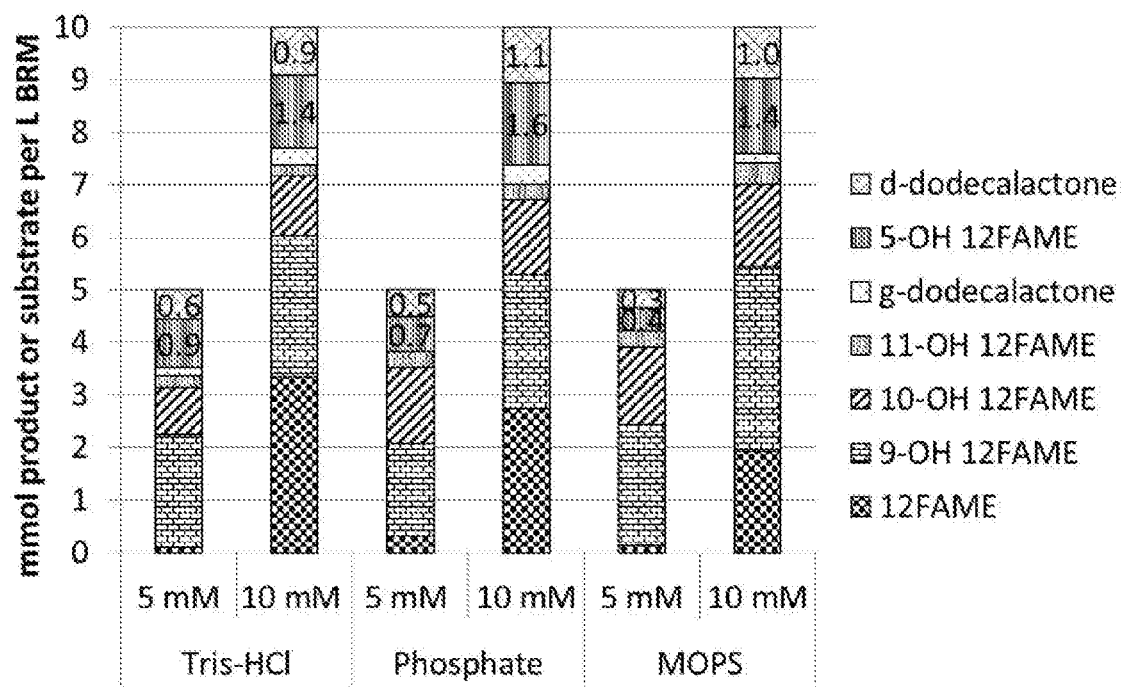
FIG. 7: Shows product distribution after 24 h conversions of dodecanoic acid by CFEs from CYP505E3 expressing *E. coli* cultures resuspended in different buffers at pH 8. The CYP concentrations in the Tris-HCl, Phosphate and MOPS buffers were respectively 1.1, 1.3 and 1.5 μM. Values are the averages for duplicate reactions.
Figure 8:
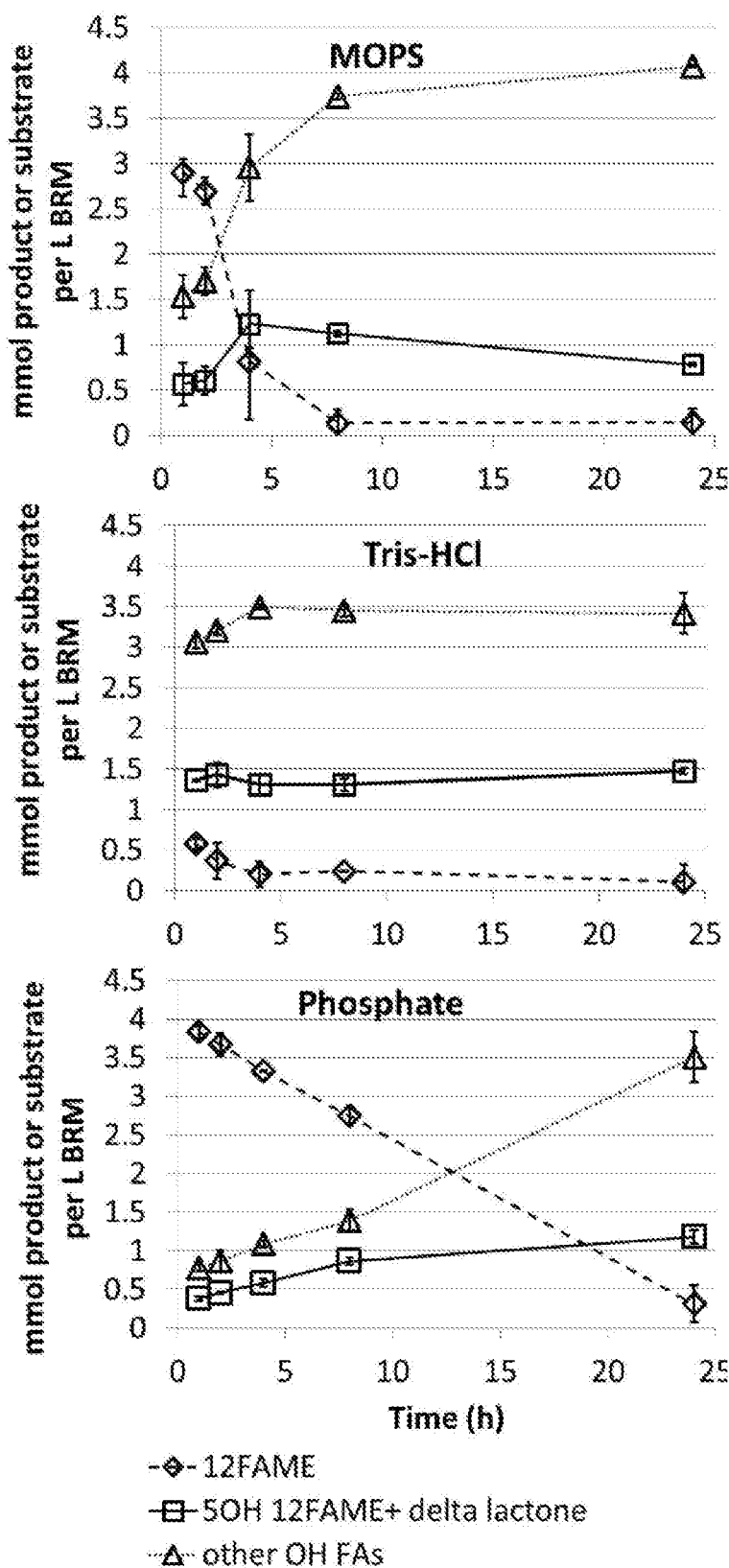
FIG. 8: Shows the conversion of dodecanoic acid by CFEs of CYP505E3 expressing *E. coli* cultures resuspended in different buffers at pH 8. The CYP concentrations in the Tris-HCl, Phosphate and MOPS buffers were respectively 1.1, 1.3 and 1.5 μM. Values are the averages and ranges for duplicate reactions.

GC-MS analyses of the methylated samples from the dodecanoic acid biotransformations revealed the formation of a complex mixture containing six different products (FIG. 7). Product concentrations were calculated from the percentage of the sum of the areas of substrate (12FAME) and products identified as γ-dodecalactone, δ-dodecalactone and dodecanoic acid hydroxylated at the 5, 9, 10 and 11 positions detected as the methyl esters designated 5-OH 12FAME, 9-OH 12FAME, 10-OH 12FAME and 11-OH 12FAME. The two products of particular interest, δ-dodecalactone and 5-OH 12FAME, comprised ca. 30-35% of the total products. 5-Hydroxy dodecanoic acid can be converted to the lactone by incubating the acidified reaction mixture at 100° C. prior to extraction. Some lactone is, however, converted to 5OH-FAME during methylation. The rate of product formation depended on the buffer used. 5 mM substrate was in all cases almost completely converted within 24 h (FIG. 8). When 10 mM substrate was added not all the substrate was converted, but more product was formed. When calculated from the percentage conversion, the amount of delta-dodecalactone and 5-hydroxy dodecanoic acid produced from 10 mM acid within 24 h varied between 2.3 and 2.6 mM depending on the buffer.

Experiment 3—Time Course of Biotransformation of 50 mM C12 Fatty Acid Using CFE of *E. coli* Expressing CYP505E3 in MOPS Buffer—Samples Analysed with and without Methylation CYP and GDH CFE suspensions prepared from cells in MOPS buffers (1 g wet weight in 5 ml buffer) were mixed in a 9:1 ratio and diluted with three parts MOPS buffer so that the final CYP concentration in the BRM was 0.2 µM. NADPH (0.1 mM) was added. Dodecanoic acid (20 µl of 2.5 M fatty acid stock solution in DMSO) was added to 1 mL BRM in 40 ml amber glass vials to give a final substrate concentration of 50 mmol·$L_{BRM}^{-1}$. These vials were placed on an orbital shaker at 20° C., 200 rpm, oscillation amplitude 26 mm. Vials were removed at specific time intervals for extraction. Biotransformation were stopped by adding 170 ul of 0.5M HCl and extracted with 2×500 µl EtOAc containing 2 mM decanoic and 2 mM tetradecanol as internal standards.

After extraction aliquots (50 µl) of ethyl acetate extracts containing both decanoic acid and tetradecanol as internal standards were methylated for GC-MS analysis while the rest of the extracts were washed with a $Na_2CO_3$ (5% w/v) solution to remove the fatty acids. The washed ethyl acetate extracts were also analysed by GC-MS and the δ-dodecalactone and γ-dodecalactone concentrations determined from a standard curve.

Figure 9:
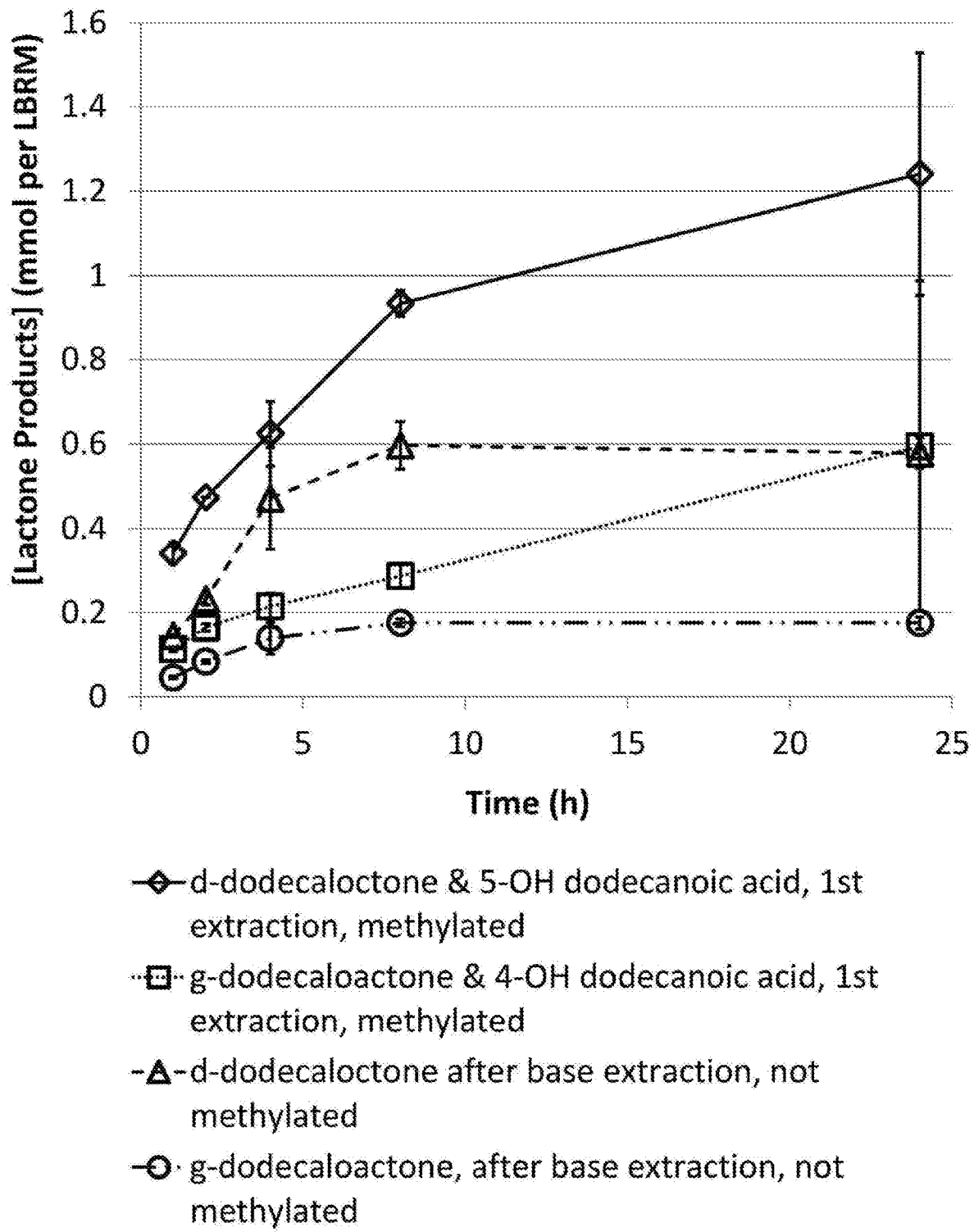
FIG. 9: Shows the conversion of dodecanoic acid by CFEs of CYP505E3 expressing *E. coli* cultures resuspended in 200 mM MOPS buffer pH 8. Final CYP concentration in the BRM was 0.2 μM. Aliquots of ethyl acetate extracts were methylated prior to GC analysis, while the rest was washed with $Na_2CO_3$ (5% w/v) and then analysed without methylation.

The lactone concentrations in the washed ethyl acetate samples were significantly lower (0.6 mmol·$L_{BRM}^{-1}$) than those in the unwashed samples (1.6 mmol·$L_{BRM}^{-1}$) indicating that a large percentage of the hydroxy fatty acids did not close to form the lactone (FIG. 9).

Experiment 4—Biotransformation of C12, C14 and C16 Alkanes Using CFE of *E. coli* Expressing CYP505E3

Biotransformations of dodecane, tetradecane and hexadecane were carried using only CYP505E3 containing CFE prepared from an *E. coli* cell suspension (1 g wet weight in 10 ml buffer) in MOPS buffer (200 mM, pH 8) containing glucose and glycerol (100 mM each) as well as 0.1 mM NADPH. Alkane substrates (250 µL) were added to 1 mL BRM in 40 ml amber glass vials. These vials were placed on an orbital shaker at 20° C., 200 rpm, oscillation amplitude 26 mm and incubated for 24 h.

Figure 10:
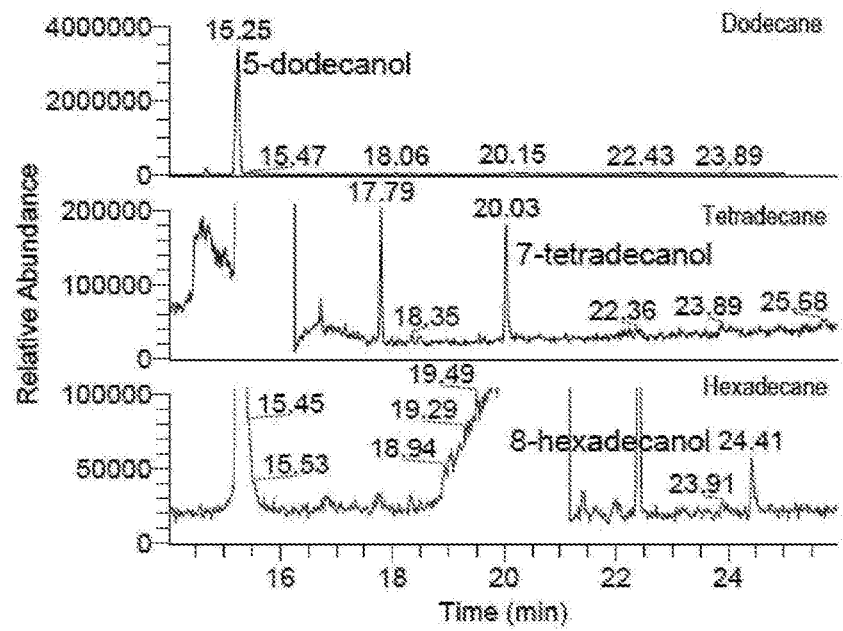
FIG. 10: Show the GC-MS analyses results of the ethyl acetate extracts from biotransformations of dodecane, tetradecane and hexadecane carried out with CYP505E3 containing CFEs of *E. coli* in MOPS buffer.
Figure 10:
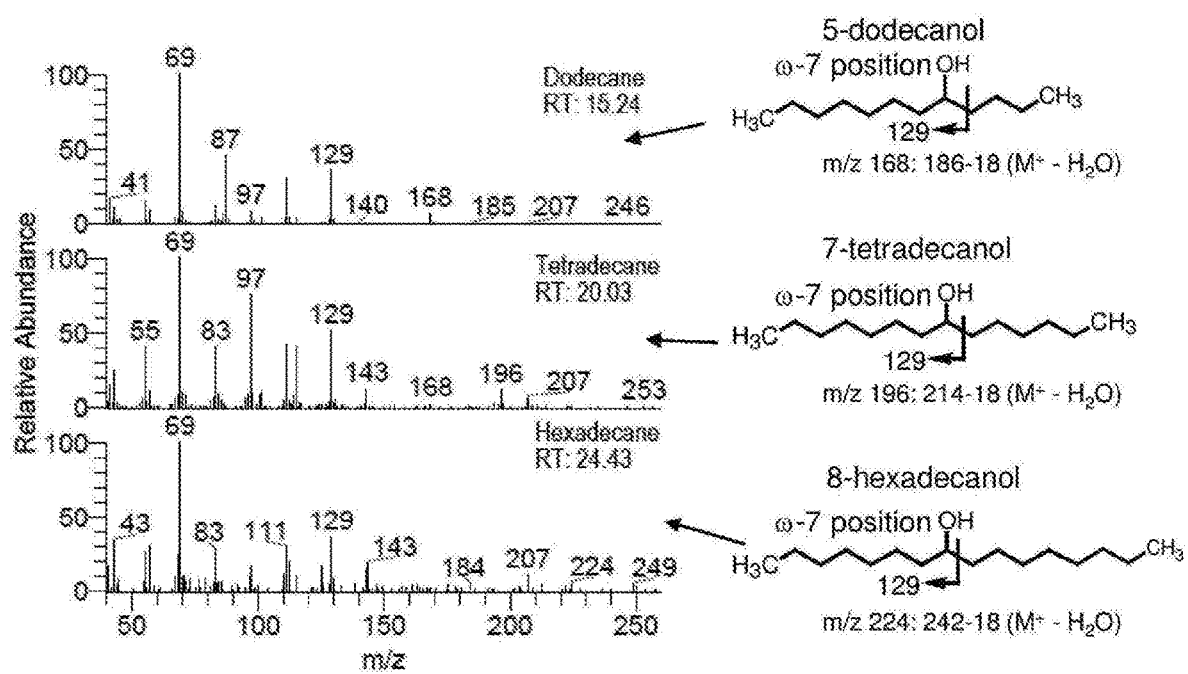

GC-MS analysis of the ethyl acetate extracts revealed that dodecane, tetradecane and hexadecane were transformed to give in each case a single product and that all three alkanes were hydroxylated at what can be described as position ω-7 to give respectively 5-dodecanol, 7-tetradecanol and 8-hexadecanol (FIG. 10). Terminal hydroxylation of these alcohol products at the suitable positions to form 1,5-dodecanediol, 1,7-tetradecane diol and 1,9-hexadecane diol can again eventually after further oxidation yield δ-dodecalactone (FIG. 5).

Experiment 5—Biotransformation of Dodecanol Using CFE of *E. coli* Expressing CYP505E3

Figure 11:
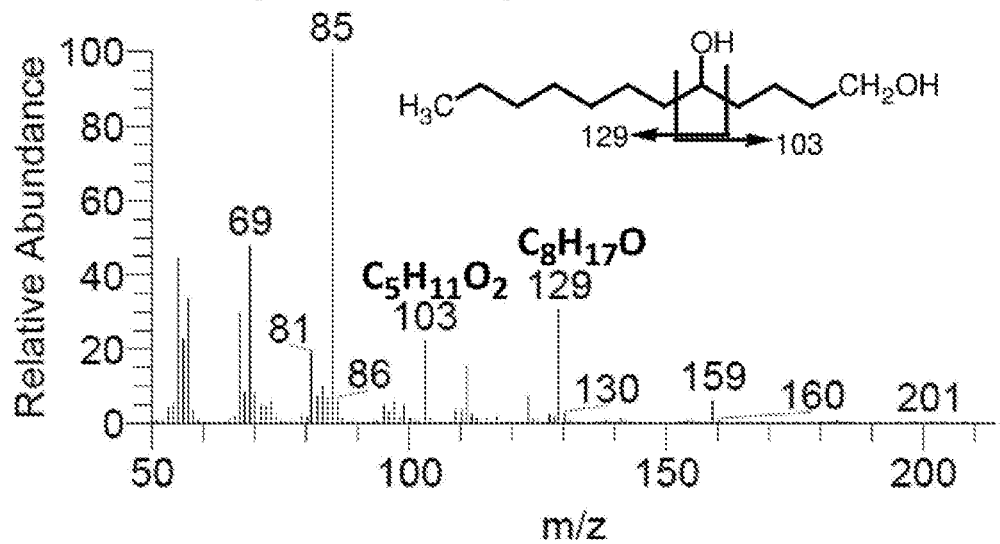
FIG. 11: Shows the conversion of dodecanol to 1,5-dodecanediol by CFE of CYP505E3 expressing *E. coli* cultures resuspended in 200 mM MOPS buffer pH 8. Final CYP concentration in the BRM was 0.2 μM. (A) Mass spectrum of 1,5-dodecanediol and (B) Time course of the conversion.
Figure 11:
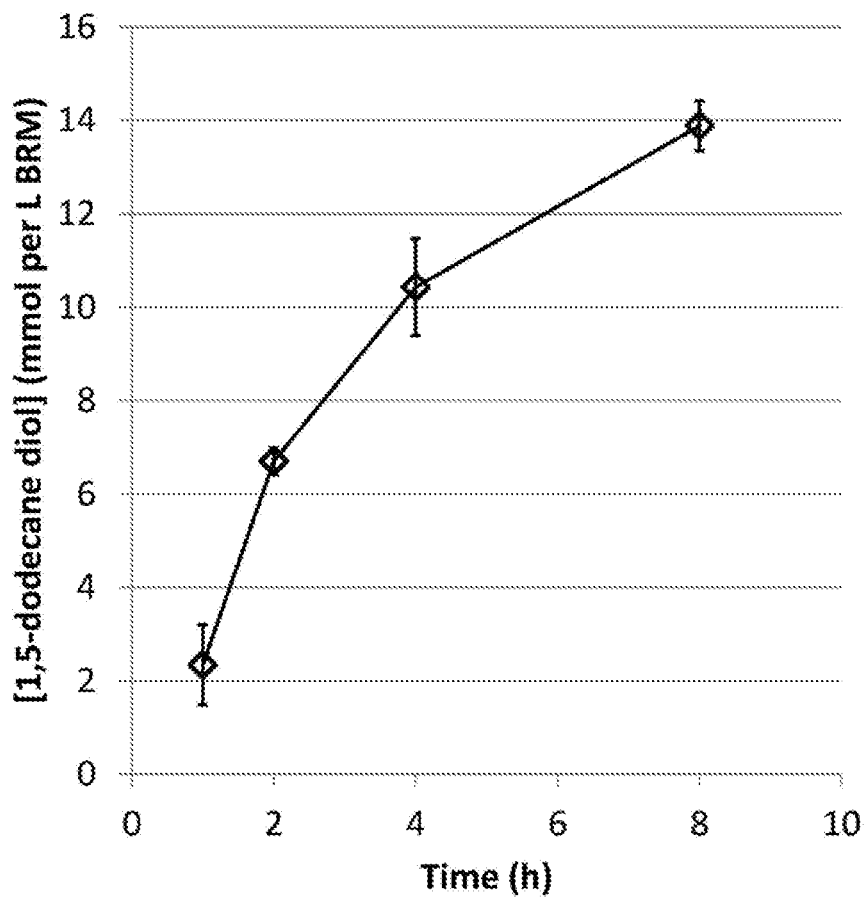

CYP and GDH CFE suspensions prepared from cells in MOPS buffers (1 g wet weight in 5 ml buffer) were mixed in a 9:1 ratio and diluted with three parts MOPS buffer so that the final CYP concentration in the BRM was 0.2 µM. Dodecanol (40 µL) was added to 1 mL BRM in 40 ml amber glass vials. These vials were placed on an orbital shaker at 25° C., 200 rpm, oscillation amplitude 26 mm. Vials were removed at specific time intervals for extraction. Biotransformation were stopped by adding 170 ul of 0.5M HCl and extracted with 2×500 µl EtOAc containing 2 mM tetradecanol as internal standards. GC-MS revealed the formation of up to 14 mmol·$L_{BRM}^{-1}$ 1,5-dodecanediol within 8 h (FIG. 11).

Experiment 6—Biotransformation of Dodecanol Using Permeabilized Whole Cells of *E. coli* Expressing CYP505E3—25 mL Scale An *E. coli* culture expressing CYP505E3 was harvested and the cell pellet resuspended in MOPS buffer (200 mM, pH 8) containing 25 mM glucose and 25 mM glycerol to give a final biomass concentration of 60 $g_{wcw}$/L. *E. coli* cells expressing GDH was also harvested and the cell pellet resuspended in MOPS buffer (200 mM, pH 8) to give a final biomass concentration of 30 $g_{wcw}$/L. These cell suspensions were treated with 1% wt/v Tween 80 for 10 min at 37° C. to permeabilize the cells. The GDH containing cells were recovered by centrifugation. The CYP containing cell suspension (25 mL) was transferred to a 250 mL Erlenmeyer shake flask and GDH containing cells added to give a final concentration of 1 $g_{wcw}$/L of GDH cells. After 10 min the biotransformation reaction was started by the addition of dodecanol (125 µL, 27 mM) and the reaction mixture incubated at 25° C. and 180 rpm. After 15 h GDH containing cells (1 $g_{wcw}$/L) as well as glucose (25 mM, 0.3 mL of 2 M solution) and glycerol (25 mM, 0.3 mL of 2 M solution) were added again. The reaction was stopped after 24 h with the addition of ethyl acetate and the total reaction mixture extracted with ethyl acetate (2×25 mL). The final extract (50 mL) contained 17.7 mM dodecanol and 4.5 mM 1,5 dodecanediol.

Figure 12:
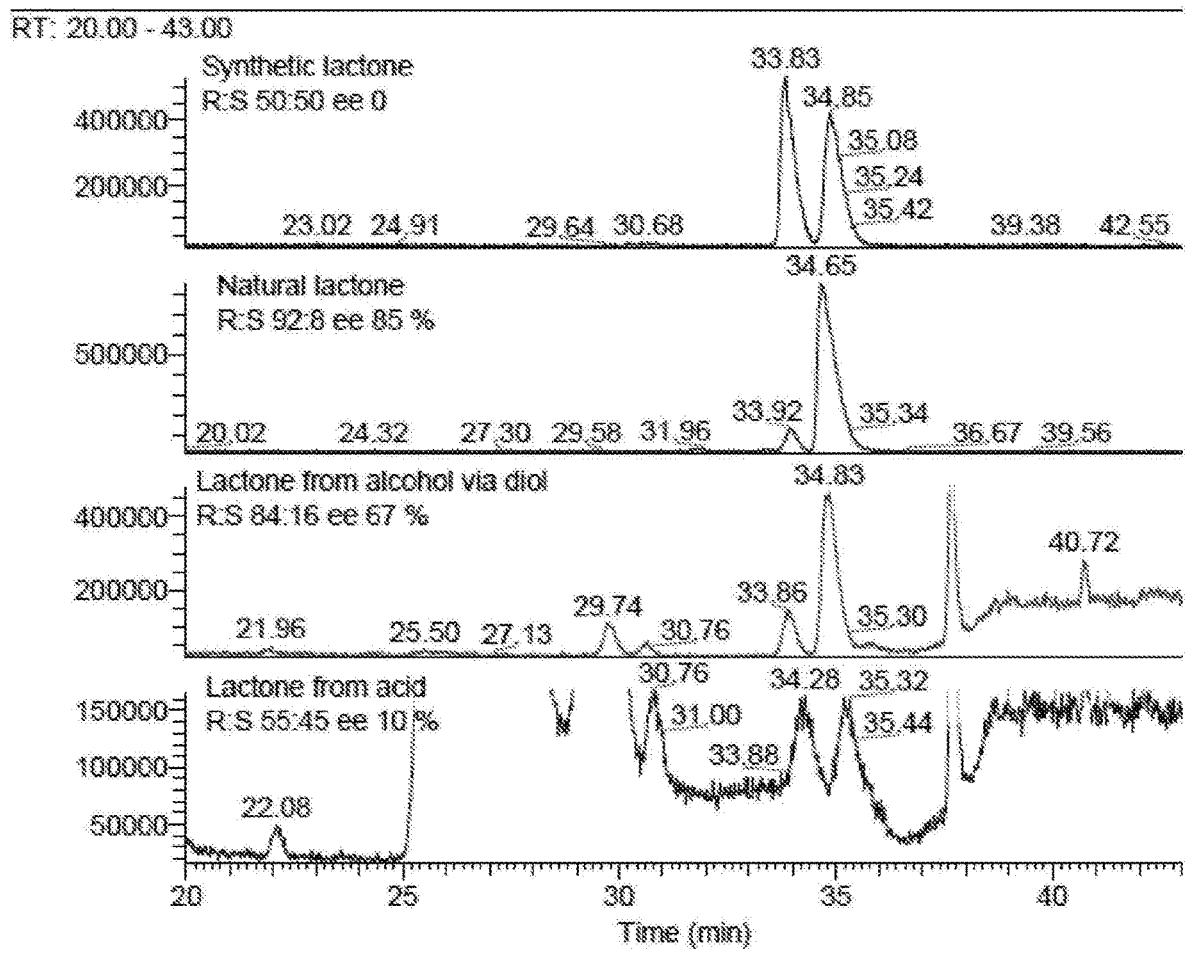
FIG. 12: Depicts the chiral analysis of δ-dodecalactone produced from 1,5-dodecanediol using HLADH and directly from dodecanoic acid using CYP505E3.

Experiment 7—Conversion of 1,5-dodecane Diol to δ-dodecalactone and Chiral Analysis of Lactones Produced from Dodecanol and C12 Fatty Acid To convert 1,5-dodecanediol to δ-dodecalactone 170 µL of an ethyl acetate extract containing 150 mM dodecanol and 5.5 mM 1,5-dodecanediol was placed in a 40 mL vial and the ethyl acetate evaporated by incubating the vial at 100° C. for 5 min. After evaporation of the ethyl acetate the dodecanol/dodecanediol mixture was resuspended in 1 mL of an HLADH expressing culture of *E. coli* permeabilized with Triton X100 (1% v/v was added and the cell suspension incubated at 37° C. for 10 min). This reaction mixture containing 1 mM of 1,5-dodecanediol and 25 mM of dodecanol was incubated at 30° C. and 180 rpm for 24 h. It was then extracted with ethyl acetate (2×0.5 mL) containing 2 mM undecanol as internal standard and analysed on a VF5 column using a GC with FID detector for quantification and a GC-MS with a Chiraldex G-TA column (30 m×0.25 mm ID) to determine enantioselectivity. The ethyl acetate extract contained 0.2 mM 1,5-dodecanediol and 0.65 mM δ-dodecalactone (R:S ratio 84:16, ee 67%) while the δ-dodecalactone produced from dodecanoic acid in previous experiments using CYP505E3 was an almost racemic mixture (R:S ratio 55:45, ee 10%) (FIG. 12).

Experiment 8—Biotransformation of Dodecanol to 1,5-dodecane Diol by a Culture of Wild-Type *Aspergillus terreus*

Spores of *Aspergillus terreus* MRC 11081 were inoculated into 100 mL of Potato Dextrose Broth (PDB, 24 g/L) in a 250 mL Erlenmeyer flask, and the flask was incubated for 5 days at 28° C. After this time, 1-dodecanol (1 mL) was added to the culture and incubation continued. Every 24 h triplicate samples (1 mL) of the culture was taken, extracted with ethyl acetate containing 2 mM 1-undecanol (2×0.5 mL) and analysed by Gas Chromatography. The biotransformation reaction was carried out as described above for 6 days.

Figure 13:
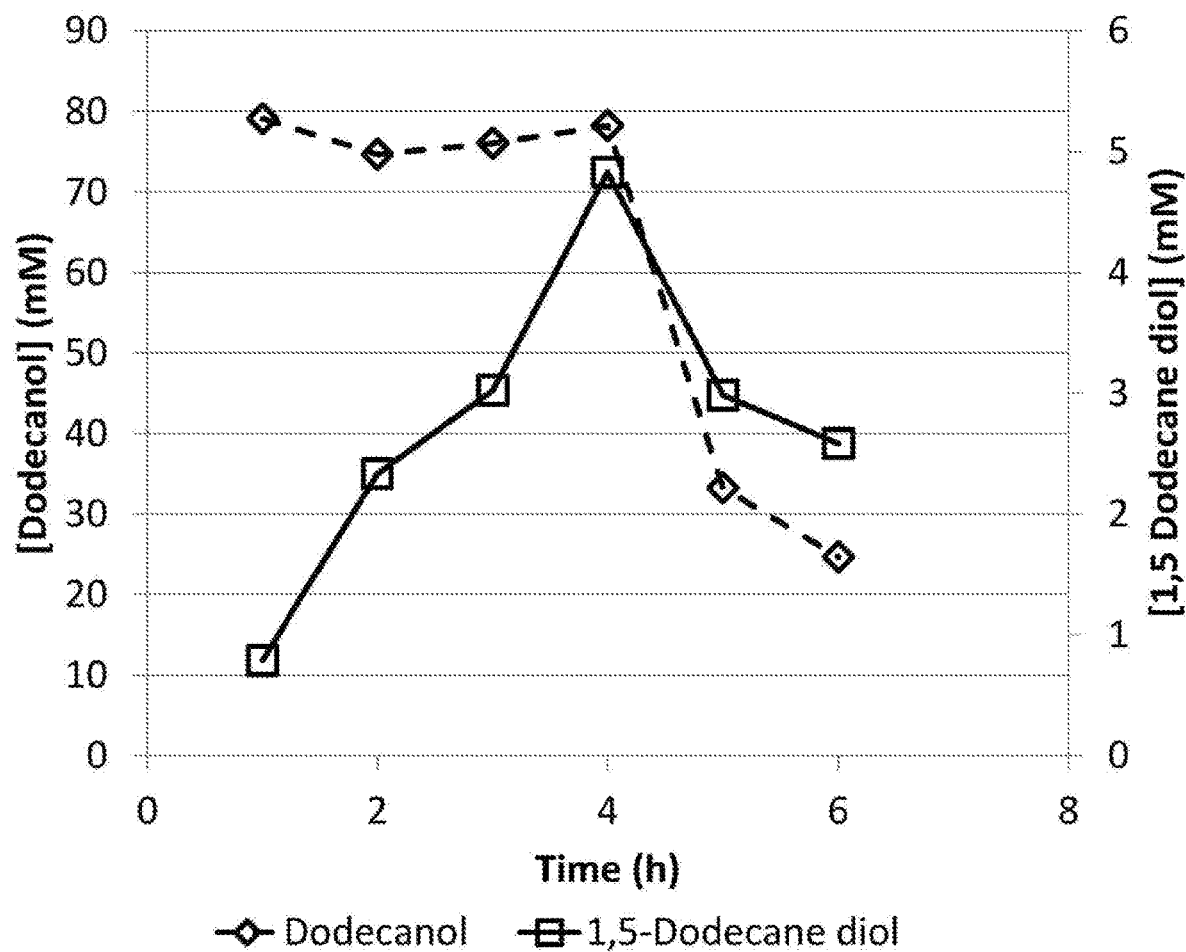
FIG. 13: Shows the conversion of dodecanol to 1,5-dodecanediol by a culture of *A. terreus* grown in potato dextrose broth.

The ethyl acetate extracts from cultures of the wild-type *A. terreus* contained a maximum of 4.8 mM 1,5-dodecane-diol after 4 days after which the fungus started to consume both the substrate and the product (FIG. 13).

Experiment 9—Biotransformation of C12 and C14 Fatty Acids and Fatty Alcohols and C12 Alkane by Different CYP505s Expressed in *Pichia pastoris*

Different transformants of *Pichia pastoris* KM71 harbouring the CYP505 genes for SEQ ID Nos 1 to 7 and 9 to 12 were grown and harvested as described above. The harvested cells were resuspended to give 1 g wet cell weight in 40 ml MOPS buffer (200 mM, 100 mM glucose, 100 mM glycerol, pH 8) and 1 ml aliquots of these cell suspensions were transferred to 40 ml amber vials. Dodecane, 1-dodecanol and 1-tetradecanol were added neat to these cell suspensions to give final concentrations of 200 mM in the case of the alcohols and 1 M in the case of dodecane while in the case of dodecanoic acid 20 µl of a 500 mM stock solution (in DMSO) was added to give a final concentration of 10 mM. Transformants harbouring the CYP505 genes for SEQ ID Nos 1 to 4 were tested for the biotransformation of 1-dodecanol, 1-tetradecanol, dodecanoic acid, tetradecanoic acid and dodecane, while those harbouring the CYP505 genes for SEQ ID Nos 5 to 7 and 9 to 12 were only tested for the biotransformation of 1-dodecanol and dodecanoic acid. The biotransformations were incubated at 25° C. and 225 rpm for 24 h. Extractions were performed using ethyl acetate (500 µl×2). The extracts were analyzed using GC/MS.

Figure 14:
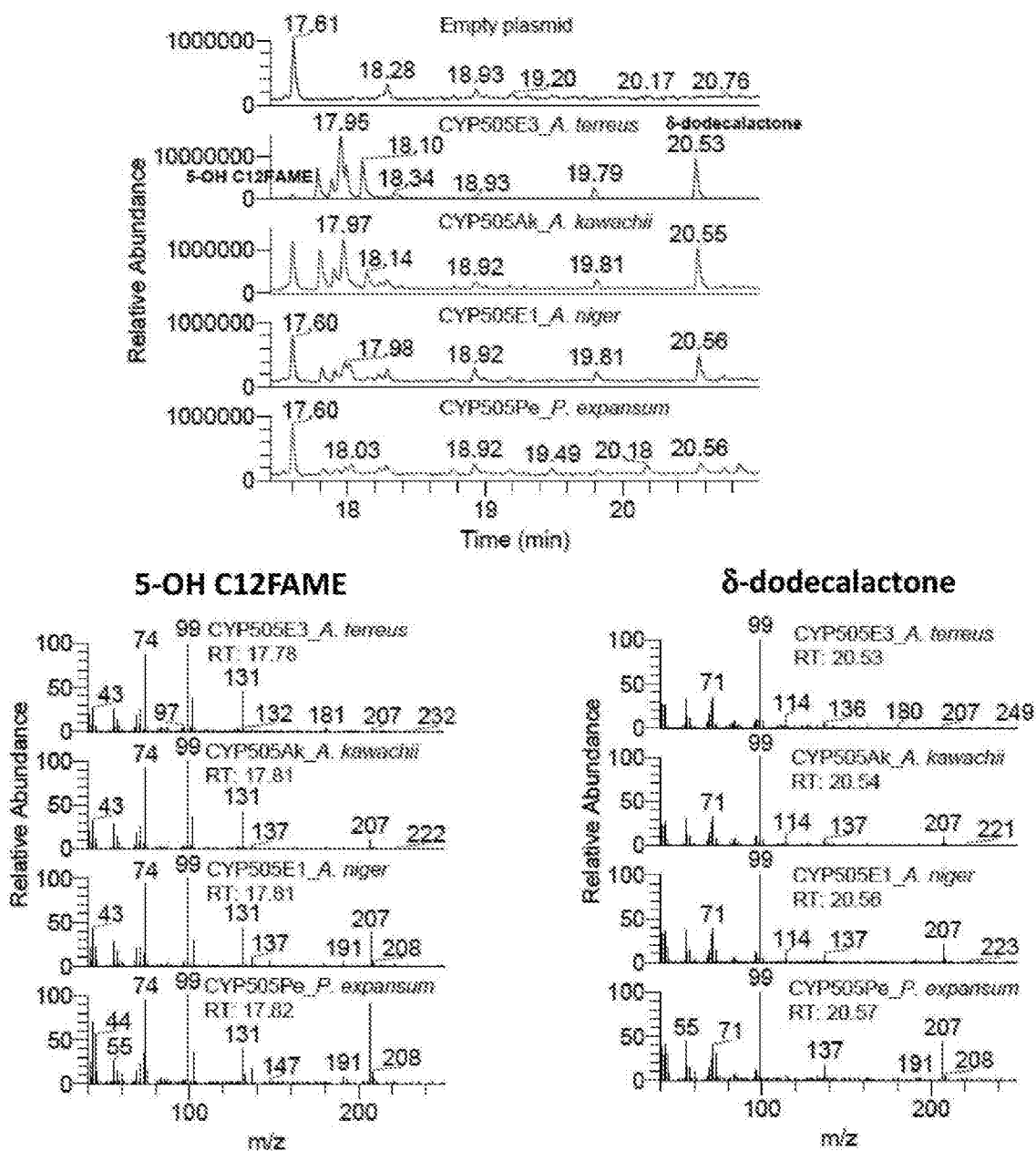
FIG. 14: Depicts GC-MS analyses of the methylated samples from the whole cell biotransformations of dodecanoic acid by the CYP505s from *Aspergillus terreus* (CYP505E3, SEQ ID No 1), *Aspergillus kawachii* (CYP505Ak, SEQ ID No 2), *Aspergillus niger* (CYP505E1, SEQ ID No 3) and *Penicillium expansum* (CYP505Pe, SEQ ID No 4) expressed in *P. pastoris*.

GC-MS analyses of the methylated samples from the biotransformations of dodecanoic acid by the CYP505s from *Aspergillus terreus* (CYP505E3, SEQ ID No 1), *Aspergillus kawachii* (CYP505Ak, SEQ ID No 2), *Aspergillus niger* (CYP505E1, SEQ ID No 3) and *Penicillium expansum* (CYP505Pe, SEQ ID No 4) showed that all four these enzymes expressed in *P. pastoris* produced δ-dodecalactone, 5-hydroxy dodecanoic acid as well as other hydroxylated C12 fatty acids (FIG. 14).

Figure 15:
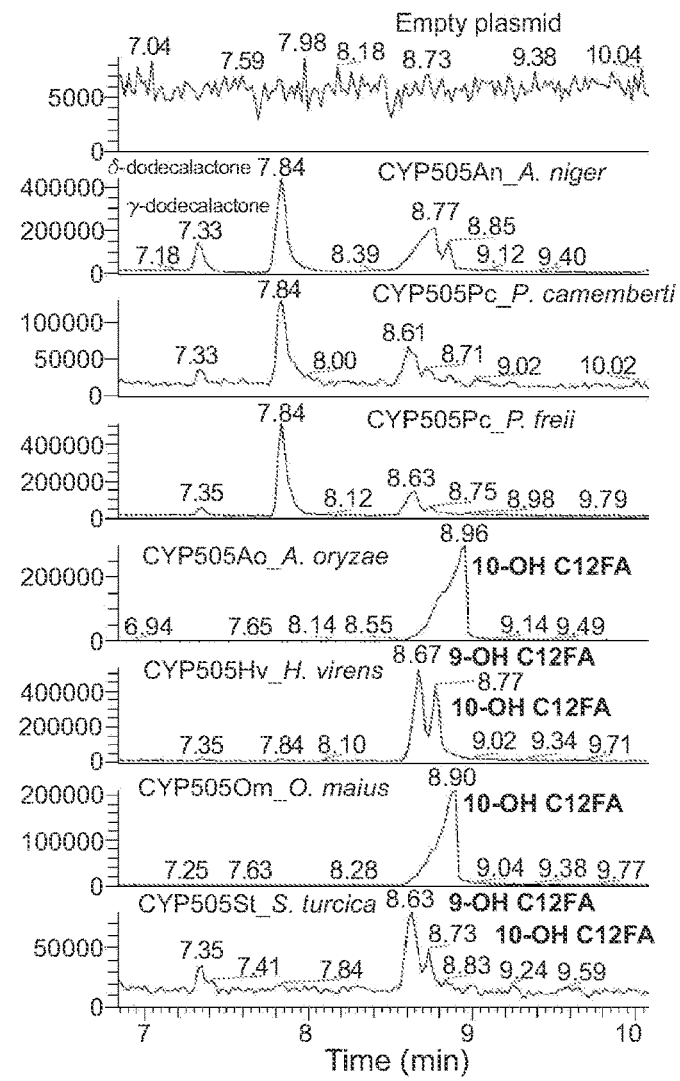
FIG. 15: Depicts GC-MS analyses of the unmethylated samples from the whole cell biotransformations of dodecanoic acid by the CYP505s from *Aspergillus niger* (CYP505An, SEQ ID No 5), *Penicillium camemberti* (CYP505Pc, SEQ ID No 6), *Penicillium freii* (CYP505Pf, SEQ ID No 7), *Aspergillus oryzae* (CYP505Ao, SEQ ID No 9), *Hypocrea virens* (CYP505Hv, SEQ ID No 10), *Oidiodendron maius* (CYP505Om, SEQ ID No 11) and *Setosphaeria turcica* (CYP505St, SEQ ID No 11) expressed in *P. pastoris*.
Figure 15:
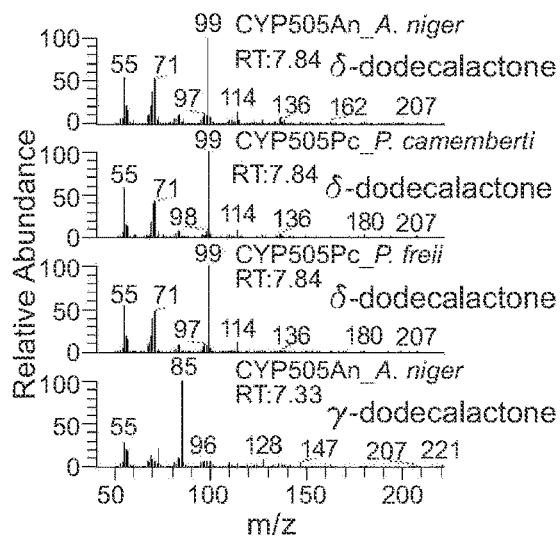
Figure 15:
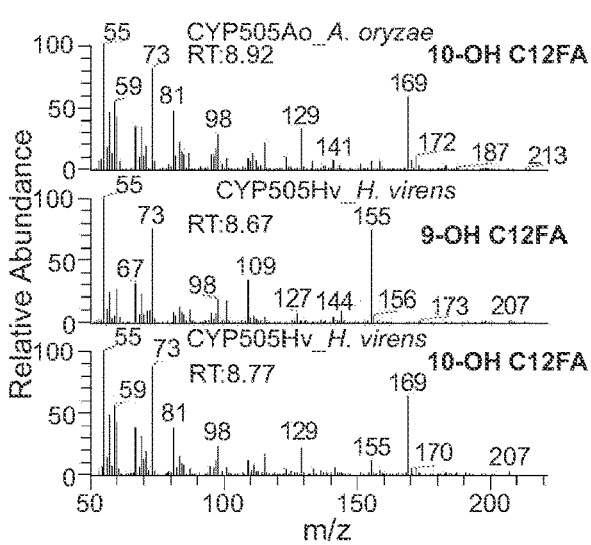

GC-MS analyses of unmethylated samples from the biotransformations of dodecanoic acid by the CYP505s from *Aspergillus niger* (CYP505An, SEQ ID No 5), *Penicillium camemberti* (CYP505Pc, SEQ ID No 6), *Penicillium freii* (CYP505Pf, SEQ ID No 7), *Aspergillus oryzae* (CYP505Ao, SEQ ID No 9), *Hypocrea virens* (CYP505Hv, SEQ ID No 10), *Oidiodendron maius* (CYP505Om, SEQ ID No 11) and *Setosphaeria turcica* (CYP505St, SEQ ID No 11) showed that the first three of these enzymes (SEQ ID Nos 5 to 7) expressed in *P. pastoris* produced δ-dodecalactone, 5-hydroxy dodecanoic acid as well as other hydroxylated C12 fatty acids while the last four (SEQ ID Nos 9 to 12) produced only sub-terminally hydroxylated C12 fatty acids (FIG. 15).

Figure 16:
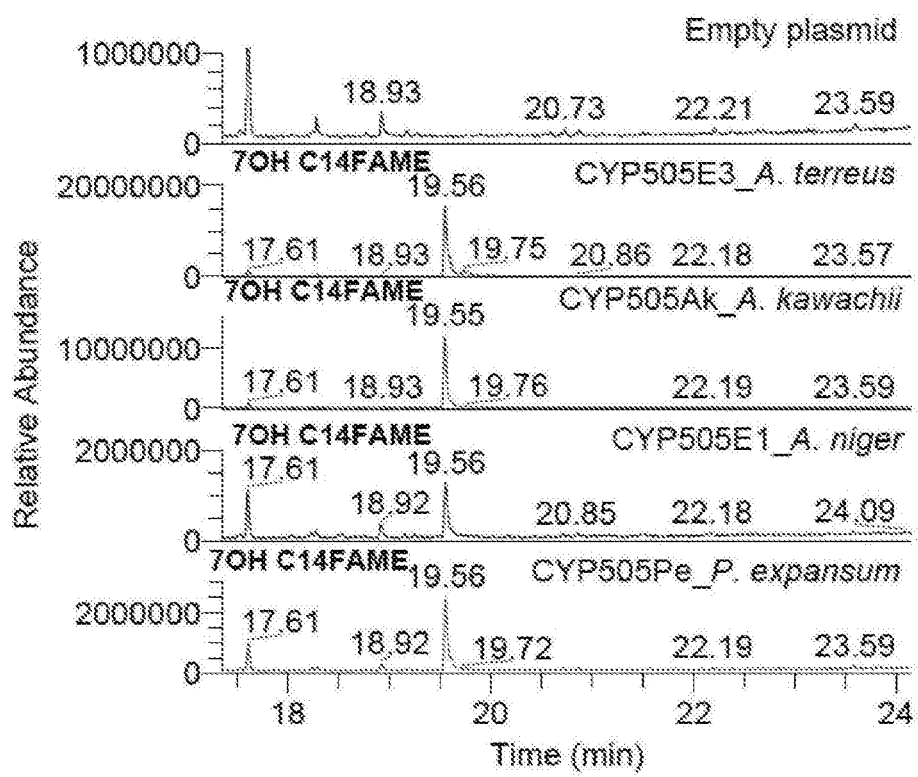
FIG. 16: Shows GC-MS analyses of the methylated samples from the whole cell biotransformations of tetradecanoic acid by the CYP505s from *Aspergillus terreus* (CYP505E3, SEQ ID No 1), *Aspergillus kawachii* (CYP505Ak, SEQ ID No 2), *Aspergillus niger* (CYP505E1, SEQ ID No 3) and *Penicillium expansum* (CYP505Pe, SEQ ID No 4) expressed in *P. pastoris*.
Figure 16:
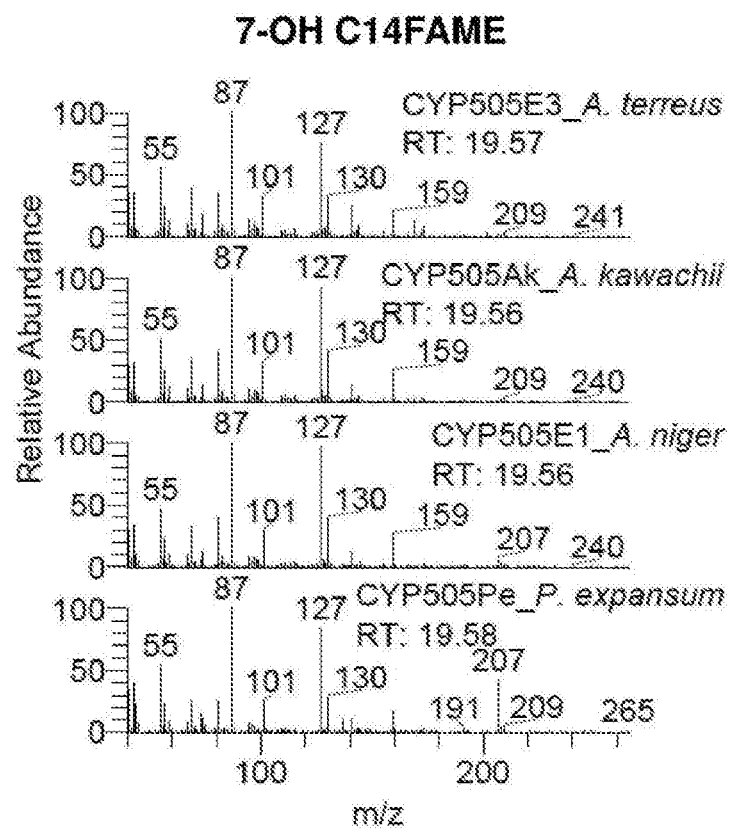

GC-MS analyses of the methylated samples from the biotransformations of tetradecanoic acid by CYP505E3 (SEQ ID No 1), CYP505Ak (SEQ ID No 2), CYP505E1 (SEQ ID No 3) and CYP505Pe (SEQ ID No 4) expressed in *P. pastoris* showed that all four these enzymes expressed in *P. pastoris* produced only 7-hydroxy tetradecanoic acid (FIG. 16).

Figure 17:
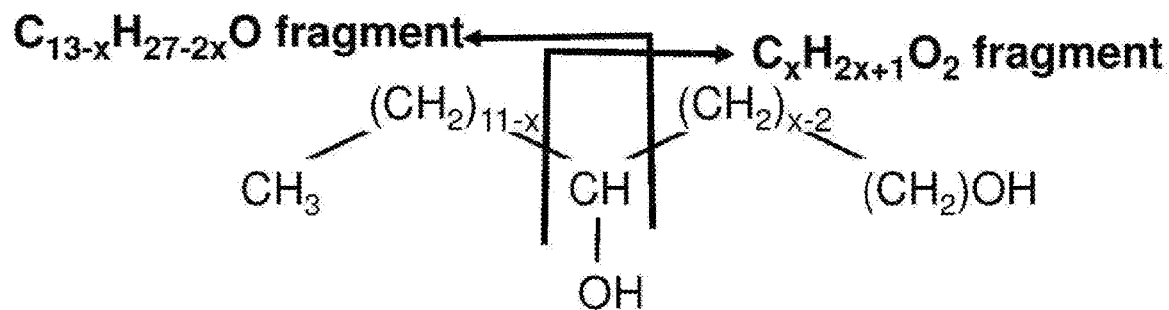
FIG. 17: Depicts expected fragments with masses used to identify the C12 diols produced by the different CYP505s expressed in *P. pastoris*.
Figure 18:
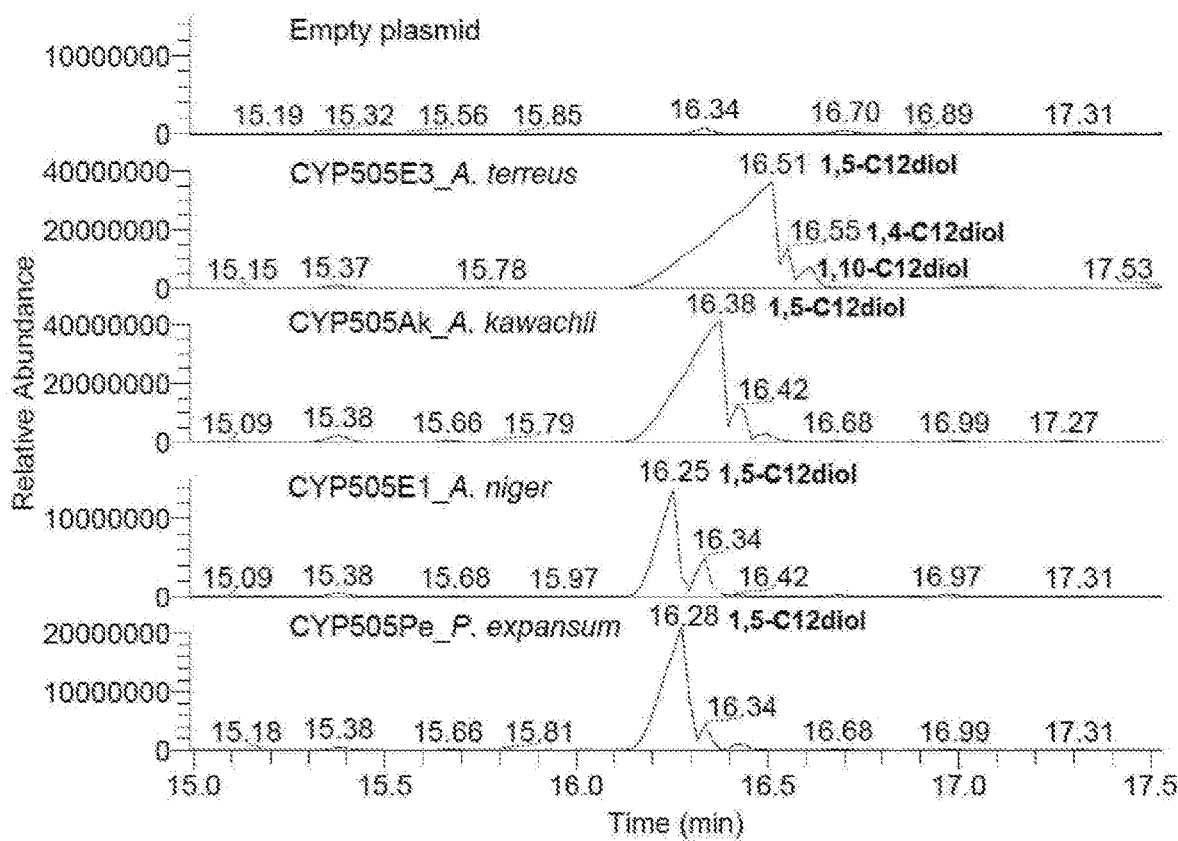
FIG. 18: Shows GC-MS analyses of samples from the whole cell biotransformations of 1-dodecanol by the CYP505s from *Aspergillus terreus* (CYP505E3, SEQ ID No 1), *Aspergillus kawachii* (CYP505Ak, SEQ ID No 2), *Aspergillus niger* (CYP505E1, SEQ ID No 3) and *Penicillium expansum* (CYP505Pe, SEQ ID No 4) expressed in *P. pastoris*.
Figure 18:
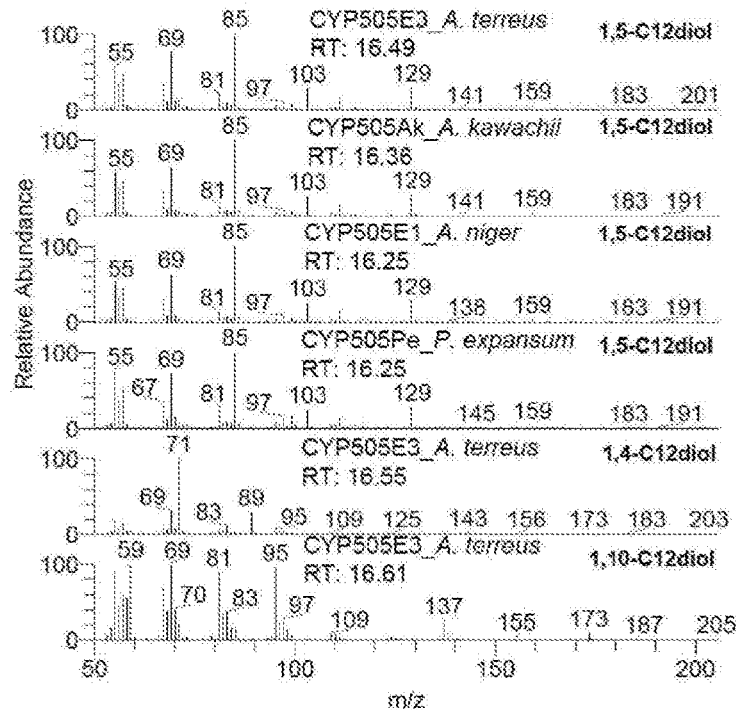
Figure 19:
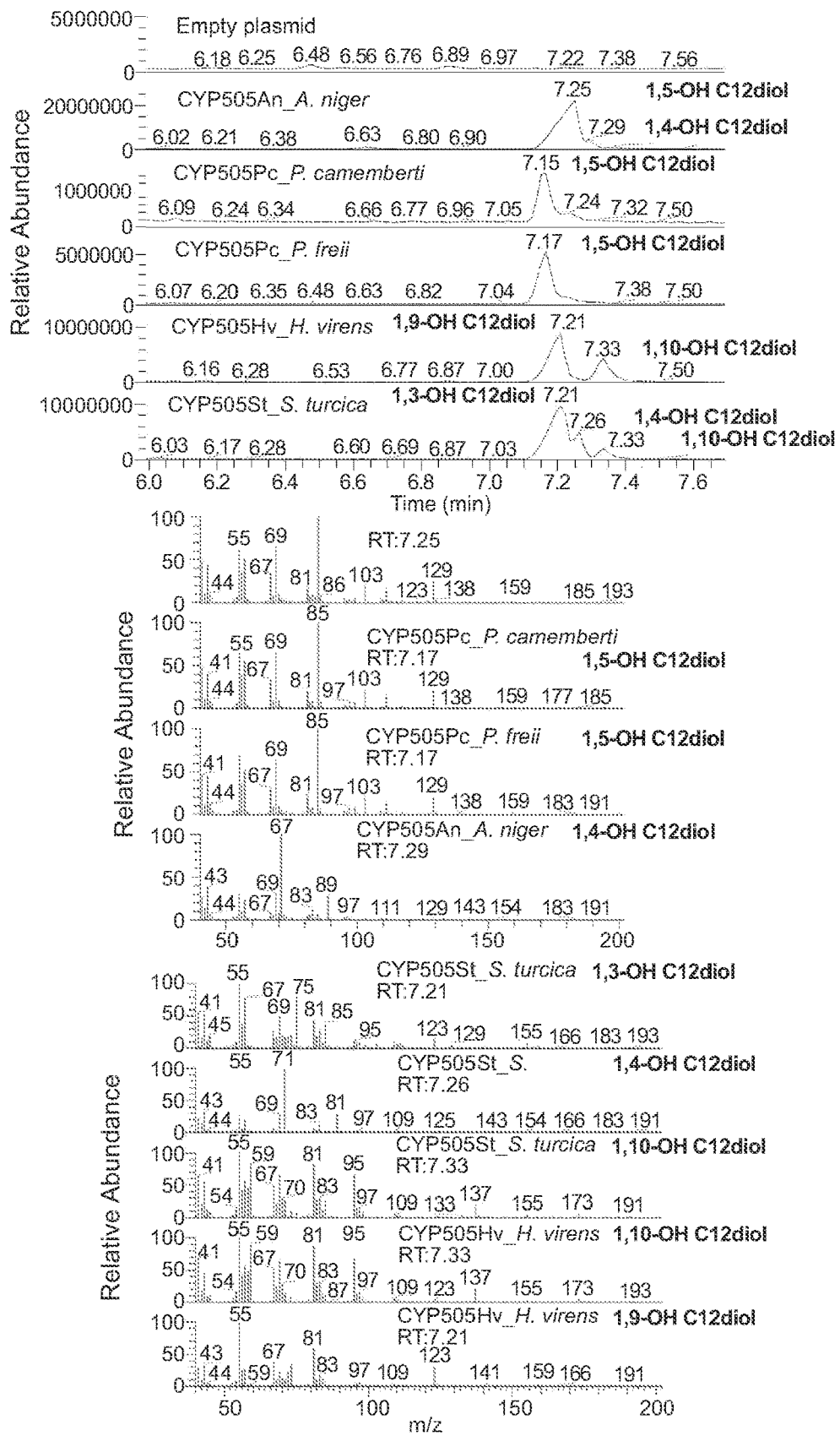
FIG. 19: Depicts GC-MS analyses of samples from the whole cell biotransformations of 1-dodecanol by the CYP505s from *Aspergillus niger* (CYP505An, SEQ ID No 5), *Penicillium camemberti* (CYP505Pc, SEQ ID No 6), *Penicillium freii* (CYP505Pf, SEQ ID No 7), *Hypocrea virens* (CYP505Hv, SEQ ID No 10), and *Setosphaeria turcica* (CYP505St, SEQ ID No 11) expressed in *P. pastoris*.
Figure 20:
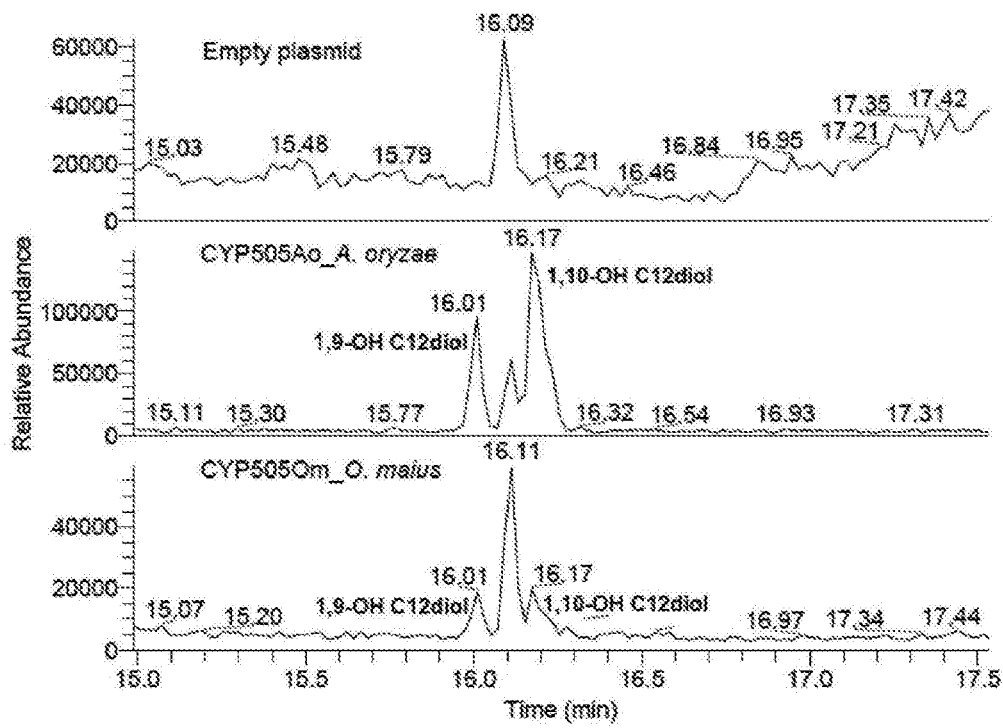
FIG. 20: Shows GC-MS analyses of samples from the whole cell biotransformations of 1-dodecanol by the CYP505s from *Aspergillus oryzae* (CYP505Ao, SEQ ID No 9) and *Oidiodendron maius* (CYP505Om, SEQ ID No 11) expressed in *P. pastoris*.
Figure 20:
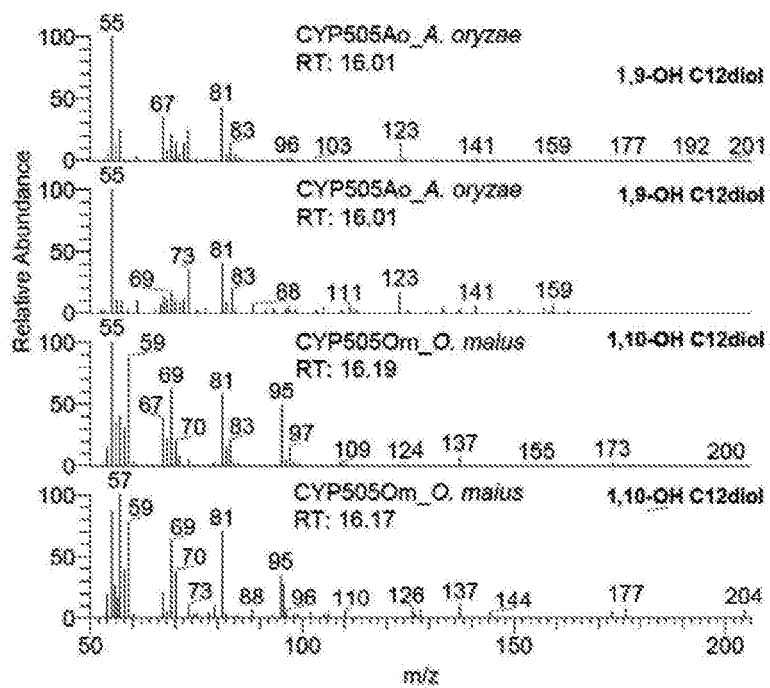

No standards were available for the diols that could be produced from 1-dodecanol and diol products had to be identified by comparing the expected fragments (FIG. 17) with mass spectra obtained. CYP505E3 (SEQ ID No 1), CYP505Ak (SEQ ID No 2), CYP505E1 (SEQ ID No 3), CYP505Pe (SEQ ID No 4), CYP505An (SEQ ID No 5), CYP505Pc (SEQ ID No 6) and CYP505Pf (SEQ ID No 7) all produced 1,5 dodecanediol (FIGS. 18 and 19), while CYP505Hv (SEQ ID No 10), CYP505St (SEQ ID No 11), CYP505Ao (SEQ ID No 9) and CYP505Om (SEQ ID No 11) produced other hydroxylated products as indicated in FIGS. 19 and 20.

Figure 21:
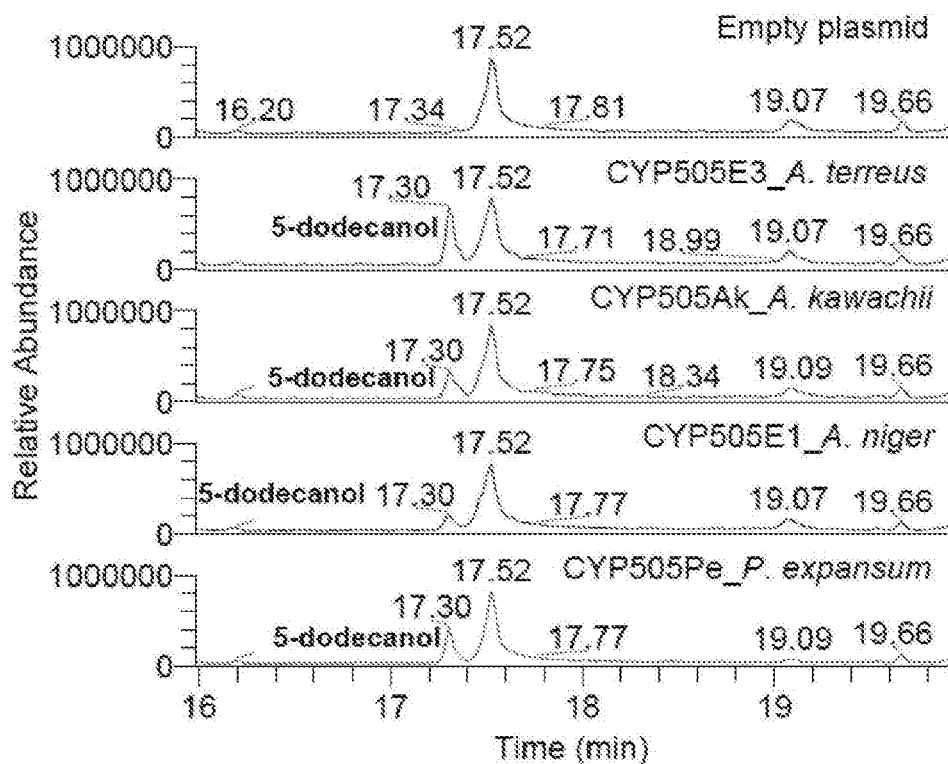
FIG. 21: Shows GC-MS analyses of samples from the whole cell biotransformations of 1-tetradecanol by the CYP505s from *Aspergillus terreus* (CYP505E3, SEQ ID No 1), *Aspergillus kawachii* (CYP505Ak, SEQ ID No 2), *Aspergillus niger* (CYP505E1, SEQ ID No 3) and *Penicillium expansum* (CYP505Pe, SEQ ID No 4) expressed in *P. pastoris*.
Figure 21:
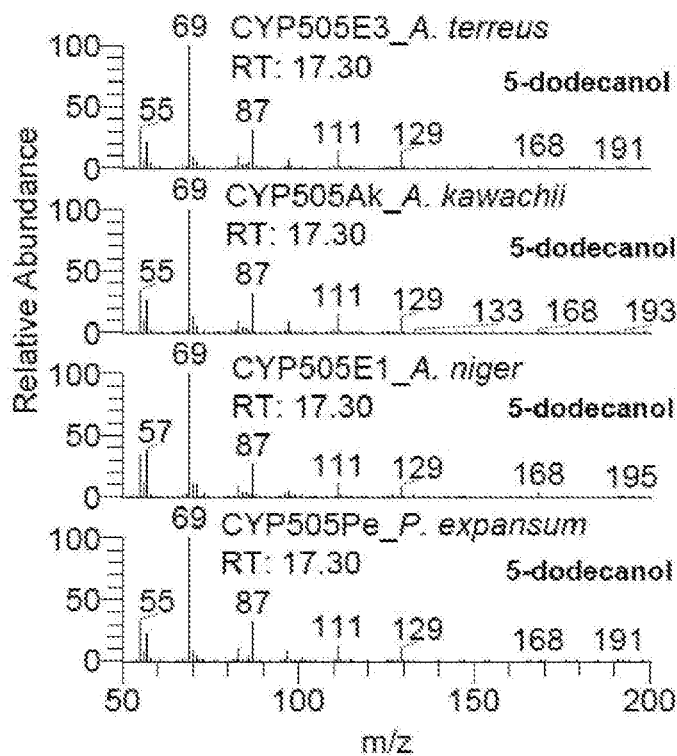

Only CYP505E3 (SEQ ID No 1), CYP505Ak (SEQ ID No 2), CYP505E1 (SEQ ID No 3) and CYP505Pe (SEQ ID No 4) were tested for the biotransformation of 1-tetradecanol and only CYP505E3 and CYP505Ak gave products which were identified as 1,7- and 1,8-tetradecane diol (FIG. 21).

Figure 22:
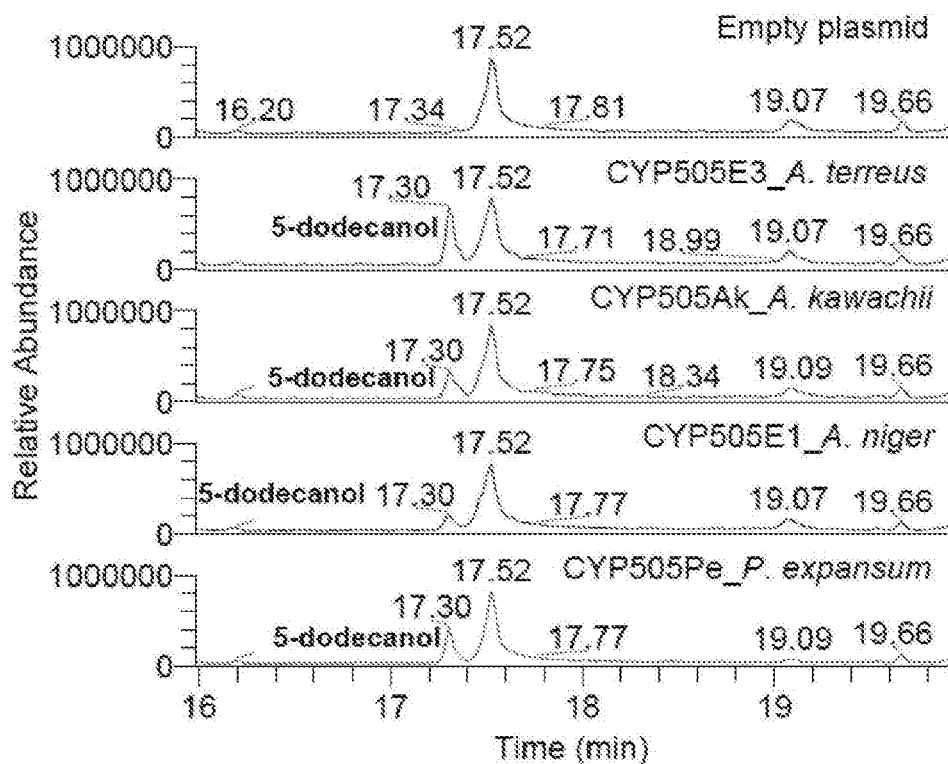
FIG. 22: Depicts GC-MS analyses of samples from the whole cell biotransformations of dodecane by the CYP505s from *Aspergillus terreus* (CYP505E3, SEQ ID No 1), *Aspergillus* niger (CYP505E1, SEQ ID No 3) and *Penicillium expansum* (CYP505Pe, SEQ ID No 4) expressed in *P. pastoris*.
Figure 22:
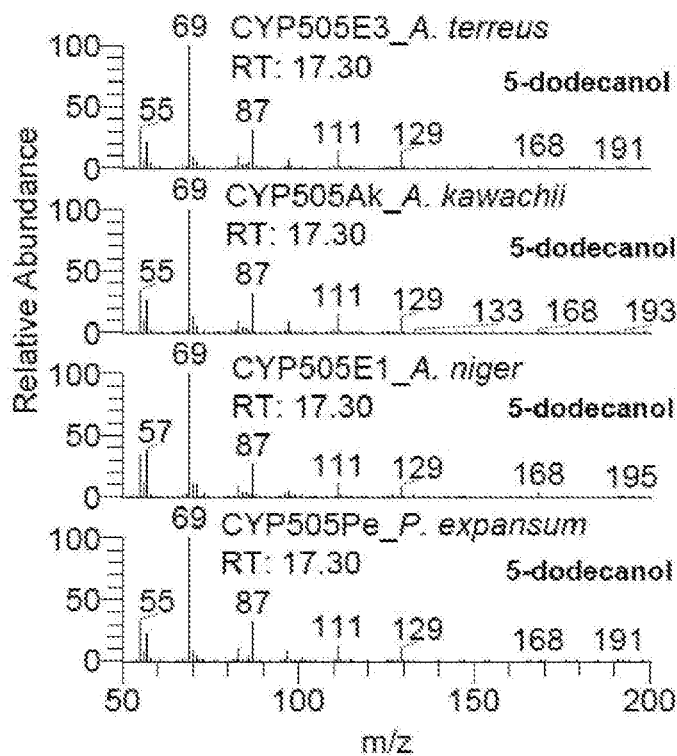

Again only CYP505E3 (SEQ ID No 1), CYP505Ak (SEQ ID No 2), CYP505E1 (SEQ ID No 3) and CYP505Pe (SEQ ID No 4) were tested for the biotransformation of dodecane and all four produced 5-dodecanol (FIG. 22)

Experiment 10—Determining the Amino Acid Identity Between CYP505s with ω-7 Hydroxylase Activity The results obtained with the different CYP505s tested for the hydroxylation of C12, C14 and C16 fatty acids, fatty alcohol and alkanes are summarized in Table 2. The amino acid sequences of the 12 different CYP505s were aligned using the MUSCLE algorithm as applied in the Genious 6.0.6 software package and the calculated amino acid identities are displayed in FIG. 23. Comparison of Table 4 and FIG. 22 shows that the CYP505s with ω-7 hydroxylase activity which can be used for the synthesis of δ-dodecalactone are CYP505E3 (SEQ ID No 1), CYP505Ak (SEQ ID No 2), CYP505E1 (SEQ ID No 3), CYP505Pe (SEQ ID No 4), CYP505An (SEQ ID No 5), CYP505Pc (SEQ ID No 6) and CYP505Pf (SEQ ID No 7) which all share at least 72.8% amino acid identity. The remaining five CYP505s tested share less than 50.7% amino acid identity with these CYP505s (ω-7 hydroxylases) and did not display detectable ω-7 hydroxylase activity towards the substrates tested. BLAST searches of the UNIPROT databases (http://www.uniprot.org/blast/) performed on 25 Sep. 2016 did not provide any CYP505s with amino acid identities between 51 and 72% to the CYP505s with ω-7 hydroxylase activity.

TABLE 2

Summary of ω-7 hydroxylase activity in twelve CYP505s tested

| Seq ID | CYP name | Organism | ω-7 hydroxylase activity[a] (in brackets other hydroxylase activities) | | | | | | | |
|---|---|---|---|---|---|---|---|---|---|---|
| | | | C12FA[b] | C14FA[b] | C16FA[c] | C12ol[c] | C14o[b] | C12alk[b] | C14alk[c] | C16alk[c] |
| 1 | CYP505E3 | *A. terreus* | +++ (++++) | ++++ | ++ | ++++ (++) | ++ (++) | +++ | ++ | + |
| 2 | CYP505Ak | *A. kawachii* | +++ (+++) | ++++ | nd | ++++ (++) | ++ (++) | ++ | nd | nd |

TABLE 2-continued

Summary of ω-7 hydroxylase activity in twelve CYP505s tested

| Seq ID | CYP name | Organism | C12FA[b] | C14FA[b] | C16FA[c] | C12ol[c] | C14o[b] | C12alk[b] | C14alk[c] | C16alk[c] |
|---|---|---|---|---|---|---|---|---|---|---|
| 3 | CYP505E1 | A. niger | ++ (++) | +++ | nd | ++++ (++) | – | + | nd | nd |
| 4 | CYP505Pe | P. expansum | + (+) | +++ | nd | ++++ (+) | – | ++ | nd | nd |
| 5 | CYP505An | A. niger | +++ (+++) | nd | nd | ++++ (+) | nd | nd | nd | nd |
| 6 | CYP505Pc | P. camemberti | ++ (++) | nd | nd | ++ | nd | nd | nd | nd |
| 7 | CYP505Pf | P. freii | ++ (+) | nd | nd | +++ | nd | nd | nd | nd |
| 8 | CYP505A1 | F. oxysporum | – (+++) | – (++) | – (++) | nd | – | nd | nd | nd |
| 9 | CYP505Ao | A. oryzae | – (+++) | nd | nd | – (++) | nd | nd | nd | nd |
| 10 | CYP505Hv | H. virens | – (++) | nd | nd | – (+++) | nd | nd | nd | nd |
| 11 | CYP505Om | O. maius | – (+++) | nd | nd | – (++) | nd | nd | nd | nd |
| 12 | CYP505St | S. turcica | – (+) | nd | nd | – (++) | nd | nd | nd | nd |

[a]Activity levels estimated from peak heights of relative abundance (RA) on GC-MS chromatograms
++++ RA > 10 million;
+++ 1 million < RA < 10 million;
++ 0.1 million < RA < 1 million;
+ – 0.01 million < RA < 0.1 million;
– no significant activity detected;
nd not tested
[b]All enzymes except CYP505A1 tested with whole cells of P. pastoris, which was only tested in CFEs of E. coli
[c]Only tested with CFE of E. coli Experiment 11—Biotransformation of C12 and C14 Fatty Acids to δ-dodecalactone by CYP505An Expressed in Pichia pastoris A transformant of Pichia pastoris KM71 harbouring the gene encoding CYP505An (SEQ ID No 5) was grown and harvested as described above. The harvested cells were resuspended 1 g in 40 ml of MOPS (200 mM, 100 mM glucose, 100 mM glycerol, pH 8) buffer and 12.5 ml was transferred to each of two 500 ml Erlenmeyer flask. One flask was supplemented with 250 µl of a 500 mM dodecanoic acid stock solution (in DMSO) and the other flask with 250 µl of a 500 mM tetradecanoic acid stock solution (in DMSO) to give in each case a final concentration of 10 mM of the fatty acid. The flasks were incubated at 25° C. and 180 rpm for 12 h. Samples (800 µl) were withdrawn after 12 h and 136 µl of 5 M HCl added. These samples were stored for 5-6 h at room temperature to convert hydroxy fatty acids to the lactone. These were then extracted with ethyl acetate (2×800 µl). GC-MS analyses of these extracts showed that δ-dodecalactone was produced from both dodecanoic acid and tetradecanoic acid (FIG. 24), confirming δ-dodecalactone production from tetradecanoic acid via β-oxidation by viable yeast cells (in this case P. pastoris) expressing a CYP505 with ω-7 hydroxylase activity (in this case CYP505An, SEQ ID No 5) (FIG. 5C).

REFERENCES

Choi, S., Kim, M., Kim, S. & Jeon, J. (2003). Microplate assay measurement of cytochrome P450-carbon monoxide complexes. J Biochem Mol Biol 36, 332-335.

Crešnar, B. & Petrič, S. (2011). Cytochrome P450 enzymes in the fungal kingdom. Biochim Biophys Acta 1814, 29-35.

Fairbanks, G., Steck, T. L. & Wallachl, D. F. H. (1968). Electrophoretic analysis. Biochemistry 10, 2606-2617.

Gillam, E. M. J. (2008). Engineering cytochrome P450 enzymes. Chem Res Toxicol 21, 220-231.

Gudiminchi, R. K. & Smit, M. S. (2011). Identification and characterization of 4-hexylbenzoic acid and 4-nonyloxy-benzoic acid as substrates of CYP102A1. Appl Microbiol Biotechnol 90, 117-126.

Inoue, H., Nojima, H. & Okayma, H. (1990). High efficiency transformation of Escherichia coli with plasmids. Gene 96, 23-28.

Johnston, W. A, Huang, W., De Voss, J. J., Hayes, M. A. & Gillam, E. M. J. (2008). Quantitative whole-cell cytochrome P450 measurement suitable for high-throughput application. J Biomol Screen 13, 135-141.

Kara, S., Spickermann, D., Schrittwieser, J. H., Weckbecker, A., Leggewie, C., Arends, I. W. C. E., and Hollmann, F. (2013) Access to Lactone Building Blocks via Horse Liver Alcohol Dehydrogenase-Catalyzed Oxidative Lactonization. ACS Catal. 3: 2436-2439.

Khow, O. & Suntrarachun, S. (2012). Strategies for production of active eukaryotic proteins in bacterial expression system. Asian Pacific J Trop Biomed 159-162.

Kitazume, T., Takaya, N., Nakayama, N. & Shoun, H. (2000). Fusarium oxysporum fatty-acid subterminal hydroxylase (CYP505) is a membrane-bound eukaryotic counterpart of Bacillus megaterium cytochrome P450BM3. J Biol Chem 275, 39734-39740.

Kitazume, T., Tanaka, A., Takaya, N., Nakamura, A., Matsuyama, S., Suzuki, T. & Shoun, H. (2002). Kinetic analysis of hydroxylation of saturated fatty acids by recombinant P450foxy produced by an Escherichia coli expression system. Eur J Biochem 269, 2075-2082.

Kuloyo, 0.0., (2014) Heterologous expression of cytochrome P450 monooxygenases from *Aspergillus terreus* and *Cryptococcus neoformans*. M.Sc. thesis University of the Free State Laemmli, U. K. (1970). Cleavage of structural proteins during the assembly of the head of bacteriophage T4. *Nature* 227, 680-685.

Li, S., Podust, L. M. & Sherman, D. H. (2007). Engineering and analysis of a self-sufficient biosynthetic cytochrome P450 PikC fused to the RhFRED reductase domain. *J Am Chem Soc* 129, 12940-12941.

Moktali, V., Park, J., Fedorova-Abrams, N. D., Park, B., Choi, J., Lee, Y.-H. & Kang, S. (2012). Systematic and searchable classification of cytochrome P450 proteins encoded by fungal and oomycete genomes. *BMC Genomics* 13, 1-13.

Nakayama, N., Takemae, A. & Shoun, H. (1996). Cytochrome P450foxy, a catalytically self-sufficient fatty acid hydroxylase of the fungus *Fusarium oxysporum*. *J Biochem* 119, 435-440.

Omura, T. & Sato, R. (1964). The carbon monoxide-binding pigment of liver microsomes: I. evidence for its hemoprotein nature. *J Biol Chem* 239, 2370-2378.

Park, J., Lee, S., Choi, J., Ahn, K., Park, B., Park, J., Kang, S. & Lee, Y.-H. (2008). Fungal cytochrome P450 database. *BMC Genomics* 9, 1-11.

Plackett, R. L. & Burman, J. P. (1946). Design of optimum multifactorial experiments. *Biometrika* 33, 305-325.

Sambrook, J., Fritsch, E. F. & Maniatis, T. (1989). *Molecular cloning: a Laboratory Manual*. 2nd edn. Cold Spring Harbor, N.Y.: Cold Spring Harbor Laboratory.

Santillán, M. & Mackey, M. C. (2008). Quantitative approaches to the study of bistability in the lac operon of *Escherichia coll*. *J R Soc interface* 5, 29-39.

Studier, F. W. (2005). Protein production by auto-induction in high-density shaking cultures. *Protein Expr Purif* 41, 207-234.

Syed, K., Shale, K., Pagadala, N. S. & Tuszynski, J. (2014). Systematic identification and evolutionary analysis of catalytically versatile cytochrome P450 monooxygenase families enriched in model basidiomycete fungi. *PLoS One* 9, 1-18.

Tamura, K., Stecher, G., Peterson, D., Filipski, A. & Kumar, S. (2013). MEGA6: Molecular evolutionary genetics analysis version 6.0. *Mol Biol Evol* 30, 2725-2729.

Terpe, K. (2006). Overview of bacterial expression systems for heterologous protein production: from molecular and biochemical fundamentals to commercial systems. *Appl Microbiol Biotechnol* 72, 211-222.

Theron, C. W., Labuschagné, M., Gudiminchi, R., Albertyn, J. & Smit, M. S. (2014). A broad-range yeast expression system reveals *Arxula adeninivorans* expressing a fungal self-sufficient cytochrome P450 monooxygenase as an excellent whole-cell biocatalyst. *FEMS Yeast Res* 1-11.

Vandamme, E. J (2003). Bioflavours and fragrances via fungi and their enzymes. *Fungal Diversity* 13, 153-166.

Vatsyayan, P., Kumar, A. K., Goswami, P. & Goswami, P. (2008). Broad substrate cytochrome P450 monooxygenase activity in the cells of *Aspergillus terreus* MTCC 6324. *Bioresour Technol* 99, 68-75.

---

The invention claimed is:

1. A process for the microbial in-chain hydroxylation of C12 to C16 fatty acids, alcohols and alkanes at position ω-7, including culturing a microorganism expressing a recombinant cytrochrome P450 (CYP450) monooxygenase that has the amino acid sequence of SEQ ID NO: 1; on a culture medium including an exogenous substrate; and isolating a hydroxylated product or secondary product formed thereof from the medium, wherein the exogenous substrate is selected from the group consisting of C12 to C16 fatty acids, alcohols and alkanes, and wherein the hydroxylated product or secondary product comprises one or more of lactones, esters and polymers.

2. The process of claim 1, wherein the microorganism is a wild-type *Aspergillus terreus* strain or other wild-type fungal strain expressing a CYP450 monooxygenase having the amino acid sequence of SEQ ID NO: 1.

3. The process of claim 1, wherein the process includes the further step of creating a Cell-Free Extract (CFE) of the cultured microorganism and combining the CFE with a medium containing the exogenous substrate.

4. The process of claim 1, wherein the C12 to C16 fatty acid comprises any one or more of C12 to C16 saturated, unsaturated, straight and branched fatty acids.

5. The process of claim 4, wherein the C12 to C16 fatty acid comprises any one or more of lauric acid, tridecylic acid, myristic acid, pentadecylic acid and palmitic acid.

6. The process of claim 1, wherein the C12 to C16 alcohol comprises any one or more of C12 to C16 saturated, unsaturated, straight and branched alcohols.

7. The process of claim 6, wherein the C12 to C16 alcohol comprises any one or more of lauryl alcohol, tridecyl alcohol, myristyl alcohol, pentadecyl alcohol, cetyl alcohol and palmitoleyl alcohol.

8. The process of claim 1, wherein the C12 to C16 alkane comprises any one or more of C12 to C16 saturated, unsaturated, branched and unbranched alkanes.

9. The process of claim 8, wherein the C12 to C16 alkane comprises any one or more of dodecane, tridecane, tetradecane, pentadecane and hexadecane.

10. The process of claim 1, wherein the lactone is delta dodecalactone.

11. The process of claim 1, wherein the esters comprise any one or more of heptyl pentanoate, butyl octanoate, heptyl nonanoate, octyl octanoate, hexyl octanoate, and heptyl heptanoate.

12. The process of claim 1, wherein the polymer comprises poly(δ-dodecalactone).

13. The process of claim 1, further comprising using the hydroxylated product, or the secondary product, in the synthesis of a lactone, ester or polymer.

* * * * *